US010376465B2

(12) United States Patent
Lipp et al.

(10) Patent No.: US 10,376,465 B2
(45) **Date of Patent: *Aug. 13, 2019**

(54) MONOVALENT METAL CATION DRY POWDERS FOR INHALATION

(71) Applicant: Pulmatrix Operating Company, Inc., Lexington, MA (US)

(72) Inventors: Michael M. Lipp, Framingham, MA (US); Jean C. Sung, Cambridge, MA (US)

(73) Assignee: Pulmatrix Operating Company, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/277,062

(22) Filed: Sep. 27, 2016

(65) Prior Publication Data

US 2017/0143624 A1 May 25, 2017

Related U.S. Application Data

(63) Continuation of application No. 13/876,312, filed as application No. PCT/US2011/053829 on Sep. 29, 2011, now Pat. No. 9,642,798.

(60) Provisional application No. 61/387,883, filed on Sep. 29, 2010, provisional application No. 61/481,879, filed on May 3, 2011.

(51) Int. Cl.

| | |
|---|---|
| ***A61K 9/00*** | (2006.01) |
| ***A61K 31/137*** | (2006.01) |
| ***A61K 31/407*** | (2006.01) |
| ***A61K 31/4745*** | (2006.01) |
| ***A61K 31/5383*** | (2006.01) |
| ***A61K 31/56*** | (2006.01) |
| ***A61K 38/00*** | (2006.01) |
| ***A61K 38/28*** | (2006.01) |
| ***A61K 39/00*** | (2006.01) |
| ***A61K 31/439*** | (2006.01) |
| ***A61K 31/496*** | (2006.01) |
| ***A61K 31/58*** | (2006.01) |
| ***A61K 31/7036*** | (2006.01) |
| ***A61K 39/395*** | (2006.01) |
| ***A61K 47/02*** | (2006.01) |
| ***A61K 47/18*** | (2017.01) |
| ***C07K 16/00*** | (2006.01) |

(52) U.S. Cl.

CPC .......... *A61K 9/0073* (2013.01); *A61K 9/0075* (2013.01); *A61K 31/137* (2013.01); *A61K 31/407* (2013.01); *A61K 31/439* (2013.01); *A61K 31/4745* (2013.01); *A61K 31/496* (2013.01); *A61K 31/5383* (2013.01); *A61K 31/56* (2013.01); *A61K 31/58* (2013.01); *A61K 31/7036* (2013.01); *A61K 38/00* (2013.01); *A61K 38/28* (2013.01); *A61K 39/00* (2013.01); *A61K 39/395* (2013.01); *A61K 47/02* (2013.01); *A61K 47/183* (2013.01); *C07K 16/00* (2013.01)

(58) Field of Classification Search

None

See application file for complete search history.

(56) References Cited

U.S. PATENT DOCUMENTS

| | | | |
|---|---|---|---|
| 3,861,386 | A | 1/1975 | Harris et al. |
| 4,085,893 | A | 4/1978 | Durley |
| 4,193,009 | A | 3/1980 | Durley |
| 4,233,405 | A | 11/1980 | Neubeck |
| 4,238,425 | A | 12/1980 | Matsuoka et al. |
| 4,637,815 | A | 1/1987 | Lemole |
| 4,643,351 | A | 2/1987 | Fukamachi et al. |
| 4,828,844 | A | 5/1989 | Rontgen-Odenthal et al. |
| 4,881,541 | A | 11/1989 | Eger, II et al. |
| 4,921,639 | A | 5/1990 | Chiu |
| 5,063,922 | A | 11/1991 | Hakkinen |
| 5,175,152 | A | 12/1992 | Singh |
| 5,230,884 | A | 7/1993 | Evans et al. |
| 5,466,680 | A | 11/1995 | Rudy |
| 5,514,665 | A | 5/1996 | Speert et al. |
| 5,551,416 | A | 9/1996 | Stimpson et al. |
| 5,571,535 | A | 11/1996 | Flowers et al. |
| 5,612,053 | A | 3/1997 | Baichwal et al. |
| 5,633,003 | A | 5/1997 | Cantor |
| 5,654,007 | A | 8/1997 | Johnson et al. |
| 5,709,202 | A | 1/1998 | Lloyd et al. |
| 5,785,049 | A | 7/1998 | Smith et al. |
| 5,817,028 | A | 10/1998 | Anderson |
| 5,855,913 | A | 1/1999 | Hanes et al. |
| 5,883,084 | A | 3/1999 | Peterson et al. |
| 5,898,037 | A | 4/1999 | Marx |
| 5,981,559 | A | 11/1999 | Nagaoka et al. |
| 5,985,309 | A | 11/1999 | Edwards et al. |
| 6,083,922 | A | 7/2000 | Montgomery |
| 6,165,463 | A | 12/2000 | Platz et al. |
| RE37,053 | E | 2/2001 | Hanes et al. |
| 6,214,536 | B1 | 4/2001 | Boucher |
| 6,254,854 | B1 | 7/2001 | Edwards et al. |

(Continued)

FOREIGN PATENT DOCUMENTS

| | | |
|---|---|---|
| CN | 1240349 | 1/2000 |
| CN | 1446877 | 10/2003 |

(Continued)

OTHER PUBLICATIONS

Adi, et al., "Agglomerate strength and dispersion of pharmaceutical powders," Journal of Aerosol Science, 42:285-294, 2011.

(Continued)

*Primary Examiner* — Dennis J Parad

(74) *Attorney, Agent, or Firm* — McDermott Will & Emery LLP

(57) ABSTRACT

The present invention is directed toward respirable dry powders and particles for systemic delivery of pharmaceutically active agents or delivery to the respiratory tract. The dry powders contain one or more monovalent metal cations (such as $Na^+$), are small and dispersible.

7 Claims, 10 Drawing Sheets

(56) References Cited

U.S. PATENT DOCUMENTS

| | | | |
|---|---|---|---|
| 6,339,075 B1 | 1/2002 | King et al. | |
| 6,447,752 B2 | 9/2002 | Edwards et al. | |
| 6,451,352 B1 | 9/2002 | Yvin et al. | |
| 6,475,523 B1 | 11/2002 | Staniforth | |
| 6,511,050 B2 | 1/2003 | Chu | |
| 6,546,927 B2 | 4/2003 | Litherland et al. | |
| 6,572,849 B2 | 6/2003 | Shahinian, Jr. | |
| 6,582,728 B1 | 6/2003 | Platz et al. | |
| 6,613,308 B2 | 9/2003 | Bartus et al. | |
| 6,635,283 B2 | 10/2003 | Edwards et al. | |
| 6,669,959 B1 | 12/2003 | Adjei et al. | |
| 6,732,732 B2 | 5/2004 | Edwards et al. | |
| 6,749,835 B1 | 6/2004 | Lipp et al. | |
| 6,793,205 B2 | 9/2004 | Eom | |
| 6,830,764 B2 | 12/2004 | Inui et al. | |
| 6,851,626 B2 | 2/2005 | Patel et al. | |
| 6,962,151 B1 | 11/2005 | Knoch et al. | |
| 6,989,155 B1 | 1/2006 | Ganderton et al. | |
| 7,008,644 B2 | 3/2006 | Batycky et al. | |
| 7,112,572 B2 | 9/2006 | Deadman et al. | |
| 7,182,961 B2 | 2/2007 | Batycky et al. | |
| 7,192,919 B2 | 3/2007 | Tzannis et al. | |
| 7,195,179 B2 | 3/2007 | Miller et al. | |
| 7,306,787 B2 | 12/2007 | Tarara et al. | |
| 7,384,649 B2 | 6/2008 | Batycky et al. | |
| 7,556,798 B2 | 7/2009 | Edwards et al. | |
| 7,575,761 B2 | 8/2009 | Bennett et al. | |
| 7,838,532 B2 | 11/2010 | Surber et al. | |
| 7,879,358 B2 | 2/2011 | Jackson et al. | |
| 8,187,637 B2 | 5/2012 | Edwards et al. | |
| 8,591,866 B2 | 11/2013 | Edwards et al. | |
| 8,758,824 B2 | 6/2014 | Lipp | |
| 8,992,983 B2 | 3/2015 | Lipp | |
| 9,061,352 B2 | 6/2015 | Lipp | |
| 9,119,778 B2 | 9/2015 | Sung | |
| 9,233,158 B2 | 1/2016 | Lipp | |
| 9,238,005 B2 | 1/2016 | Sung | |
| 2001/0008632 A1 | 7/2001 | Freund et al. | |
| 2001/0038858 A1 | 11/2001 | Roser et al. | |
| 2002/0034477 A1 | 3/2002 | Edwards et al. | |
| 2002/0056449 A1 | 5/2002 | Wakefield et al. | |
| 2002/0129812 A1 | 9/2002 | Litherland et al. | |
| 2002/0177562 A1* | 11/2002 | Weickert .............. | A61K 9/0075 514/27 |
| 2003/0055034 A1 | 3/2003 | Montgomery | |
| 2003/0068280 A1 | 4/2003 | Bannister et al. | |
| 2003/0129139 A1 | 7/2003 | Batycky et al. | |
| 2003/0129141 A1 | 7/2003 | Platz et al. | |
| 2003/0138403 A1 | 7/2003 | Drustrup | |
| 2003/0146300 A1 | 8/2003 | Denyer et al. | |
| 2003/0186894 A1 | 10/2003 | Kuo et al. | |
| 2003/0203930 A1 | 10/2003 | Chaudry et al. | |
| 2003/0232019 A1 | 12/2003 | Basu et al. | |
| 2004/0009128 A1 | 1/2004 | Rabinowitz et al. | |
| 2004/0047810 A1 | 3/2004 | Staniforth et al. | |
| 2004/0076588 A1* | 4/2004 | Batycky ............... | A61K 9/0075 424/46 |
| 2004/0076589 A1 | 4/2004 | Edwards et al. | |
| 2004/0081627 A1 | 4/2004 | Jinks et al. | |
| 2004/0105821 A1 | 6/2004 | Bernstein et al. | |
| 2004/0256487 A1 | 12/2004 | Collins et al. | |
| 2005/0004020 A1 | 1/2005 | Yu et al. | |
| 2005/0054682 A1 | 3/2005 | Phillips | |
| 2005/0123509 A1 | 6/2005 | Lehman et al. | |
| 2005/0211244 A1 | 9/2005 | Nilsson et al. | |
| 2005/0220720 A1 | 10/2005 | Edwards et al. | |
| 2005/0247306 A1 | 11/2005 | Harvey et al. | |
| 2005/0247312 A1 | 11/2005 | Davies | |
| 2005/0255049 A1 | 11/2005 | Slowey et al. | |
| 2005/0271660 A1 | 12/2005 | Wang | |
| 2005/0274378 A1 | 12/2005 | Bonney et al. | |
| 2005/0279349 A1 | 12/2005 | Patton et al. | |
| 2005/0281740 A1 | 12/2005 | Gong et al. | |
| 2006/0073173 A1 | 4/2006 | Banach et al. | |
| 2006/0142208 A1 | 6/2006 | Boucher | |
| 2006/0147520 A1 | 7/2006 | Ruegg | |
| 2006/0276483 A1 | 12/2006 | Surber et al. | |
| 2007/0092535 A1 | 4/2007 | Watts | |
| 2007/0104657 A1 | 5/2007 | Batycky et al. | |
| 2007/0105086 A1 | 5/2007 | Qin et al. | |
| 2007/0202051 A1 | 8/2007 | Schuschnig | |
| 2007/0270502 A1 | 11/2007 | Edwards et al. | |
| 2007/0275091 A1 | 11/2007 | King et al. | |
| 2007/0292454 A1 | 12/2007 | Bell et al. | |
| 2008/0038207 A1 | 2/2008 | Edwards et al. | |
| 2008/0063722 A1 | 3/2008 | Ward et al. | |
| 2008/0127972 A1 | 6/2008 | Morton | |
| 2008/0152764 A1 | 6/2008 | Kremer et al. | |
| 2008/0190424 A1 | 8/2008 | Lucking et al. | |
| 2008/0226736 A1 | 9/2008 | Caponetti et al. | |
| 2009/0192187 A1 | 7/2009 | Brambilla et al. | |
| 2009/0208999 A1 | 8/2009 | Groenendaal et al. | |
| 2009/0232744 A1 | 9/2009 | Keller et al. | |
| 2009/0285905 A1 | 11/2009 | Gordon et al. | |
| 2010/0159007 A1 | 6/2010 | Staniforth | |
| 2010/0285142 A1 | 11/2010 | Staniforth et al. | |
| 2011/0192397 A1 | 8/2011 | Saskar et al. | |
| 2011/0236492 A1 | 9/2011 | Morton | |
| 2012/0070417 A1 | 3/2012 | Batycky et al. | |
| 2012/0107414 A1 | 5/2012 | Lipp | |
| 2013/0004542 A1 | 1/2013 | Martyn | |

FOREIGN PATENT DOCUMENTS

| | | |
|---|---|---|
| CN | 1694689 A | 11/2005 |
| CN | 101106975 | 1/2008 |
| EP | 0367723 | 5/1990 |
| EP | 0652011 | 5/1995 |
| EP | 0681833 | 11/1995 |
| EP | 1142600 | 10/2001 |
| EP | 1466610 | 10/2004 |
| EP | 1709961 | 10/2006 |
| EP | 2050437 | 4/2009 |
| JP | 05123398 | 5/1993 |
| JP | 2004-503482 | 2/2004 |
| JP | 2004-532217 | 10/2004 |
| KR | 1020050056622 | 6/2005 |
| KR | 1020070104657 | 10/2007 |
| NZ | 328476 | 5/1999 |
| NZ | 305168 | 8/1999 |
| NZ | 530123 | 1/2007 |
| RU | 2140273 C1 | 10/1999 |
| WO | 1992/06695 | 4/1992 |
| WO | 1996/12470 | 5/1996 |
| WO | 1996/31221 | 10/1996 |
| WO | 1997/36574 | 10/1997 |
| WO | 1997/44013 | 11/1997 |
| WO | 1998/16205 | 4/1998 |
| WO | 1998/48875 | 11/1998 |
| WO | 1999/51096 | 10/1999 |
| WO | 1999/64014 | 12/1999 |
| WO | 2000/13677 | 3/2000 |
| WO | 2000/66206 | 11/2000 |
| WO | 2001/13892 | 3/2001 |
| WO | 2001/076610 | 3/2001 |
| WO | 2001/85136 | 11/2001 |
| WO | 2001/85137 | 11/2001 |
| WO | 2001/95874 | 12/2001 |
| WO | 2002/005730 | 1/2002 |
| WO | 2002/09574 | 2/2002 |
| WO | 2002/060468 | 8/2002 |
| WO | 2002/83079 | 10/2002 |
| WO | 2003/035028 | 1/2003 |
| WO | 2003/035028 | 5/2003 |
| WO | 2003/043585 | 5/2003 |
| WO | 2003/103632 | 12/2003 |
| WO | 2004/002551 | 1/2004 |
| WO | 2004/030659 | 4/2004 |
| WO | 2004/096204 | 11/2004 |
| WO | 2005/004852 | 1/2005 |
| WO | 2005/041921 | 5/2005 |
| WO | 2005/41922 | 5/2005 |
| WO | 2005/079755 | 9/2005 |
| WO | 2005/092289 | 10/2005 |

(56) References Cited

FOREIGN PATENT DOCUMENTS

| | | |
|---|---|---|
| WO | 2006/029209 | 3/2006 |
| WO | 2006/038070 | 4/2006 |
| WO | 2006/084131 | 8/2006 |
| WO | 2006/102438 | 9/2006 |
| WO | 2006/125153 | 11/2006 |
| WO | 2007/057714 | 5/2007 |
| WO | 2008/025560 | 6/2008 |
| WO | 2008/065666 | 6/2008 |
| WO | 2009/037503 | 3/2009 |
| WO | 2009/044141 | 4/2009 |
| WO | 2009/130560 | 10/2009 |
| WO | 2009/140587 | 11/2009 |
| WO | 2010/111640 | 9/2010 |
| WO | 2010/111641 | 9/2010 |
| WO | 2010/111644 | 9/2010 |
| WO | 2010/111650 | 9/2010 |
| WO | 2010/111680 | 9/2010 |
| WO | 2011/006073 | 1/2011 |
| WO | 2011/048379 | 4/2011 |
| WO | 2012/030645 | 3/2012 |
| WO | 2012/030647 | 3/2012 |
| WO | 2012/030664 | 3/2012 |
| WO | 2013/104892 | 7/2013 |

OTHER PUBLICATIONS

ADJEi and Garren, "Pulmonary delivery of peptide drugs: effect of partical size on bioavailability of leuprolide acetate in healthy male volunteers", J.Pharm. Res., 7:565-569 (1990).

Aldrich Catalog pp. 1502, 1998-1999.

Anderson, et al., "Effect of cystic fibrosis on inhaled aerosol boluses" Am. Rev. Respir. Dis., 140: 1317-1324 (1989).

Bergeron, et al., "Controlling droplet deposition with polymer additives" Nature. 405:772-775 (2000).

Boren, "The development of a molecular model of lung" Arch Intern Med 126(3):491-495 (1970).

Broadhead, et al., The Spray Drying of Pharmaceuticals, Drug Development and Industrial Pharmacy, 18 (11&12):1169-1206, 1992.

Bromberg and Klibanov, "Transport of proteins dissolved in organic solvents across biomimetic membranes", Proc. Natl. Acad. Sci. USA, 92(5):1262-6 (1995).

Bucca, C. and G. Rolla, "Nebulised magnesium in asthma: the right solution for an old remedy?" The Lancet, 361:2095-2096 (2003).

Burg, et al., "Cellular Response to Hyperosmotic Stresses," Am. Physiological Soc., 87:1441-1474 (2007).

Cataldo, et al., "Induced sputum: comparison between isotonic and hypertonic saline solution inhalation in patients with asthma" Chest, 120(6):1815-21 (2001).

Chan, H., "Spray Dried Powders and Powder Blends of Recombinant Human Deoxyribonuclease (rhDNase) for Aerosol Delivery," Pharmaceutical Research, 14(4): 431-437, 1997.

Jaffari, et al., "Rapid characterisation of the inherent dispersibility of respirable powders using dry dispersion laser diffraction," International Journal of Pharmaceuticals, 447:124-131, 2013.

Chiou, et al., "A novel production method for inhalable cyclosporine A powders by confined liquid impinging jet precipitation," Journal of Aerosol Science, 39:500-509, 2008.

Choi, et al., "Inhalation delivery of proteins from ethanol suspensions" Proc. Natl. Acad. Sci. 98:11103-11107 (2001).

Clarke, et al., "Resistance to two-phase-gas-liquid flow in airways" J. Appl. Physiol.29(4):464-471 (1970).

Copp, et al., "Hypertonic Shock Inhibits Growth Factor Receptor Signaling, Induces Caspase-3 Activation, and Causes Reversible Fragmentation of the Mitocholdrial Network," Am. J. Physiol, 288:C403-C415 (2005).

Costello, B., et al., "Use of the Du Nouy Ring with a Rotational Rheometer to Measure Interfacial Rheology Properties", Annual Transactions of the Nordic Rheology Society. 2006, 14.

Crowder, et al., "2001: An Odyssey in Inhaler Formulation and Design," Pharmaceutical Technology, 99-113, Jul. 2001.

Davis, et al., "Charged Polymers Modulate Retrovirus Transduction via Membrane Charge Neutralization and Virus Aggregation", Biophys J,86:1234-1242 (2004).

Dawson, et al., "Enhanced viscoelasticity of human cystic fibrotic sputum correlates with increasing microheterogeneity in particle transport", J. of Biol. Chem., 278(50):50393-50401 (2003).

Denn, M.M., "Viscoelasticity", In Process Fluid Mechanics, Prentice-Hall, Englewood Cliffs, New Jersey, pp. 358-373 (1980).

Edwards, et al., "Inhaling to mitigate exhaled bioaerosols," PNAS (2004), vol. 101, pp. 17383-17388.

Edwards, "The macrotransport of aerosol particles in the lung: aerosol deposition phenomena" J. Aerosol Sci., 26:293-317 (1995).

Edwards, et al., "Novel Inhalents for Control and Protection Against Airborne Infections," Respiratory Drug Delivery, 2006, pp. 41-48.

Eng Pa, et al., "Short-term efficacy of ultrasonically nebulized hypertonic saline in cystic fibrosis," Pediatr. Pulmonol., 21:77-83 (1996).

"European Search Report from corresponding EP Appl. No. 11177874 dated Nov. 21, 2011; PUL 103EP-DIV2".

Evrensel, et al., "Viscous airflow through a rigid tube with compliant lining: A simple model for the air-mucus interaction in pulmonary pathways", J.Biomech. Eng., 115:262-267 (1993).

Feng, et al., "Improved clearability of cystic fibrosis sputum with dextran treatment in vitro," Am. J. Respir. Crit. Care Med., 157(3):710-714 (1998).

Ferguson, et al., "Transmission intensity and impact of control policies on the foot and mouth epidemic in Great Britain", Nature, 414(6861):329 (2001).

Fiegel et al., "Airborne Infectious Disease and the Suppression of Pulmonary Bioaerolsols," DDT, Jan. 2006, 11 (1/2), pp. 51-57.

French, et al., "The influence of formulation on emission, deaggregation and deposition of dry powders for inhalation", J. Aerosol Sci., 27:769-783 (1996).

Friedmen, et al. "A Randomized, Prospective, Double-Blind Study on the Efficacy of Dead Sea Salt Nasal Irrigations," The Laryngoscope, 2006, pp. 878-882, 116.

Fuge, et al., "The geochemistry of iodine—a review", Environmental Geochemistry and Health, 8(2):31-54 (1986).

Gad-El-Hak, et al., "On the interaction of compliant coatings with boundary layer flows", J. Fluid Mech., 140:257-280 (1984).

Ganderton, "The generation of respirable clouds from coarse powder aggregates", Biopharmaceutical Sciences,3:101-105 (1992).

Geller, et al., "Development of a DPI Tobramycin Formulation using Pulmosphere Technology," J. of Aerosol Medicine and Pulmonary Drug Delivery, 24:175-182, 2011.

Ghoroi, et al., "Dispersion of fine and ultrafine powders through surface modification and rapid expansion," 85:11-24, 2013.

Goldberg, et al., "Mechanism of enhancement of microbial cell hydrophobicity by cationic polymers", J. Bacteriology, 172:5650-5654 (1990).

Gonda, "Aerosols for delivery of therapeutic and diagnostic agents to the respiratory tract", Critical Reviews in Therapeutic Drug Carrier Systems, 6:273-313 (1990).

Guo-Zhong Tao, et al., "Hyposmotic Stress Induces Cell Growth Arrest Via Proteasome Activation and Cyclin/Cyclin-Dependent Kinase Degradation," J. Biological Chemistry, 277(22): 19295-19303 (2002).

Hardy, et al. "Sensitivity of aerosol bolus behavior to methacholine-induced bronchoconstriction", Chest, 114(2):404-10 (1998).

Hatch, G.E., "Comparative Biochemistry of Airway Lining Fluid," In: Parent, R.A., Ed., Treatise on Pulmonary Toxicology, vol. 1: Comparative Biology of the Normal Lung, CRC Press, Boca Raton, Florida (1992).

Hawley's Condensed Chemical Dictionary, 14th edition John Wiley & Sons, 2001, pp. 161 and 977.

Heyder J., et al., "Deposition of particles in the human respiratory tract in the size range 0.005-15 μm" J. Aerosol Sci., 17:811-825 (1986).

Hirschman, et al., "Inhibition of human immunodeficiency virus type 1 replication by nonionic block polymer surfactants" J. Med. Virol. 42(3):249-54 (1994).

(56) References Cited

OTHER PUBLICATIONS

Hsu, et al., "Role of Viscoelasticity in Tube Model of Airway Reopening. I. Nonnewtonian Sols.", J. Appl Physiol. 7(6):2481-2489 (1994).
Im, et al., "In vivo determination of surface tension in the horse trachea and in vitro model studies", Respir. Physiol., 109:81-93 (1997).
Iwasaki, et al., "Exacerbation of influenzavirus pneumonia by intranasal administration of surfactant in a mouse model" Arch. Virol., 144:675-685 (1999).
Kaye, et al., "Simultaneously Manufactured Nano-In-Micro(SIMANIM) Particles for Dry-Powder Modified-ReleaseDelivery of Antibodies," Pharmaceutics, Preformulations and Drug Delivery, 98:11:4055-4068, 2009.
Kilpatrick, et al., "Calcium Chloride and Adrenaline as Bronchial Dilators Compared by Sequential Analysis," British Medical Journal (1954), pp. 1388-1391.
King, "Rheology of cystic fibrosis sputum after in vitro treatment with hypertonic saline alone and in combination with recombinant human deoxyribonuclease I" Am. J. Respir. Crit. Care Med., 156(1):173-7 (1997).
King and Tarsitamo, "The effect of structured and unstructured pre-operative teaching: a replication", Nurs. Res., 31(6):324-9 (1982).
King, et al., "The role of mucus gel viscosity, spinnability, and adhesive properties in clearance by simulated cough", Biorheology, 26:737-745 (1989).
King, M., et al., "Mucomodulator Therapy in Cystic Fibrosis: Balancing Mucus Clearability Against the Spread of Airborne Pathogens," Pediatric Pulmonolgy, 2004, pp. 77-79, Supp. 26.
Kirkness, et al., "Decreased surface tension of upper airway mucosal lining liquid increases upper airway patency in anaesthetised rabbits", J. Physiol., 547(Pt 2):603-11(2003).
Kurashima, et al., "A pilot study of surfactant inhalation for the treatment of asthmatic attack" Arerugi, 40(2):160-3 (1991).
Lipp, et al., "Solving medical problems with chemical engineering", Chemtech, 42-57 (Mar. 1997).
Macosko, C.W., "Linear Viscoelasticity", in Rheology. Principles, Measurements, and Applications, Wiley-VCH, New York, pp. 109-133 (1994).
Mai, X.-M, et al., "Hypertonic saline challenge tests in the diagnosis of bronchial hyperresponsiveness and asthma in children," Pediatric Allergy & Immunology, Oct. 2002, 13(5), pp. 361-267.
Makker, et al., "Relation of hypertonic saline responsiveness of the airways to exercise induced asthma symptom severity and to histamine or methacholine reactivity," Thorax, 1993, 48, pp. 142-147.
Marriott, et al., "Changes in the Gel Properties of Tracheal Mucus Induced bu Divalent Cations," Biorheology, 1979, pp. 331-337, vol. 16.
The Merck Index, 12th edition, Merck &Co., Inc., Whitehouse Station, NJ, p. 1089. 1996, pp. 177 & 1614-1615.
Merck Manual Home Edition, "Asthma: Lung and Airway Disorders," accessed at www.merck.com/mmhe/print/sec04/ch044a/html accessed on May 5, 2010.
Merck Manual Home Edition, "Chronic Obstructive Pulmonary Disease," accessed at www.merck.com/mmhe/print/sec04/ch045a/html accessed on Mar. 21, 2010.
Merck Manual Home Edition, "Acute Respiratory Distress Syndrome (ARDS)," accessed on Nov. 17, 2011 at www.merckmanuals.com/home/lung_and_airway_disorders/respiratory_filure_and_acute_respiratory_distress_syndrome/acute_respiratory_distress_syndrome_ards.html#v727948.
The Online Merck Manual Medical Second Home Edition article, entitled, "Influenza"—accessed on Feb. 22, 2010 at www.merck.com/mmhe/print/sec17/ch198/ch198d.html.
Miller, M.J., "Assessing the use of Pharmacokinetic Models in Risk Assessments on Inhaled Toxicants", School of Public Health Sciences, Environmental Health, and Toxicology (1992).
Modler, "Calcium as an Adjuvant for Spray-Drying Acid Whey," Journal of Dairy Science, 61:294-299, 1978.
Morrison, F.A., "Introduction, How Much Do I Need to Learn about Rheology?" In Understanding Rheology, Oxford University Press, New York, pp. 1-11 (2001).
Mouro, D., et al. "Enhancement of Xcelodose Capsule-Filling Capabilities Using Roller Compaction," Pharmaceutical Technology, Feb. 2006.
Nanaumi, et al., "Properties of mixed monolayers of DPCC and viscoelasticity-giving substances", Colloids & Surfaces B: Bioinformatics, 17:167-174 (2000).
Nannini, L.J., et al., "Magnesium Sulfate as a Vehicle for Nebulized Salbutamol in Acute Asthma", Am. J. Med., 108:193-197 (2000).
Oneda, et al., "The Effect of Formulation Variables on the Dissolution and Physical Properties of Spray-Dried Microspheres Containing Organic Salts," Powder Technology, 130:377-384, 2003.
Otrisal Dosierspray Losung in Novaris Consumer health, Germany.
Papineni and Rosenthal, "The size distribution of droplets in the exhaled breath of healthy human subjects", J. Aerosol Med., 10(2):105-116 (1997).
Patton and Platz, "Pulmonary delivery of peptides and proteins for systemic action", Adv. Drug Del. Rev., 8:179-196 (1992).
Paul, Fundamental Immunology, Raven Press, New York, pp. 699-716, 1984.
Perry's Chemical Engineers' Handbook, 7th ed., 1997, pp. 2-10, 2-11, 2-120, 2-121.
Piret, et al., "Sodium lauryl sulfate, a microbicide effective against enveloped and nonenveloped viruses" Curr. Drug Targets. 3(1):17-30 (2002).
Rabbini, et al., "The Influence of formulation components on the aerosolisation properties of spray dried powders," J. of Controlled Release, 110:130-140, 2005.
Raynal, et al., "Calcium-dependent Protein Interactions in MUC5B Provide Reversible Cross-links in Salivary Mucus," The Journal of Biological Chemistry, Aug. 2003, pp. 28703-28710, vol. 278 (31).
Riedler, J., et al. "Inhaled hypertonic saline increases sputum expectoration in cystic fibrosis," J. Pediatr Child Health, 32:48-50 (1996).
Robinson, M., et al., "Effect of hypertonic saline amiloride, and cough on mucociliary clearance in patients with cystic fibrosis," Am J. Respir. Crit. Care Med., 153:1503-1509 (1996).
Robinson, M., et al., "Effect of increasing doses of hypertonic saline on mucociliary clearance in patients with cystic fibrosis," Thorax, 52:900-903 (1997).
Robinson, M., et al., The effect of inhaled mannitol on bronchial mucus clearance in cystic fibrosis patients: a pilot study, Eur. Respir. J., 14:678-685 (1999).
Rosenblum, E. E. ("fish." Grolier Multimedia Encyclopedia, 2006, Grolier Online, accessed Nov. 21, 2006 (gme.grolier.com/cgi-bin/article?assetid=0106750-0).
Rote Liste Service, "Rote Liste 2002" (2002), Editor Cantor Verlag, Frankfurt/Main, XP002416908, par. [72087], par. [28005].
Rudt and Muller, "In vitro Phagocytosis Assay of Nano- and Microparticles by chemiluminescence. I. Effect of Analytical Parameters, Particle Size and Particle Concentration", J. Controlled Release, 22:263-272 (1992).
Sanders, et al., "Cystic fibrosis sputum: a barrier to the transport of nanospheres", Am J Respir Crit Care Med., 162:1905-1911 (2000).
Sarrell, et al., "Nebulized 3% Hypertonic Saline Solution Treatment in Ambulatory Children with Viral Bronchiolitis Decreases Symptoms," Chest, 2002, 122, pp. 2015-2020.
Schelling G., et al., Biophyiscal Journal, 66:134-140 (1994).
Schurch, et al., "Surfactant displaces particles toward the epithelium in airways and alveoli", Respir Physiol., 80:17-32 (1990).
Serrano, P., et al., "New Data on Pharmacological Properties and Indications of Magnesium," In New Perspectives in Magnesium Research, Springher-Verglag, London, pp. 127-139 (2007).
Seville, et al., "Spray-Dried Powders for Pulmonary Drug Delivery," Crit. Rev. in Therapeutic Drug Carrier Systems, 24(4), 307-360, 2007.
Shigeta, et al. "Synergistic Anti-Influenza Virua A (H1N1) Activities of PM-523 (Polyoxometalate) and Ribavarin In Vitro and In Vivo," Antimicrobial Agents & Chemotherapy, 1997, 41, pp. 1423-1427.

(56) References Cited

OTHER PUBLICATIONS

Suara, et al., "Effect of Zinc Salts on Respiratory Syncytial Virus Replication," Antimicrobial Agents and Chemotherapy, Mar. 2004, pp. 783-790, vol. 48 (3).
Tabata and Ikada, "Macrophage phagocytosis of biodegradable microspheres composed of L-lactic acid/glycolic acid homo- and copolymers", J. Biomed. Mater. Res., 22:837-858 (1988).
Takebayashi, et al., "Role of tachykinins in airway responses to ozone in rats" J Appl Physiol 85:442-450 (1998).
Tansey, "The challenges in the development of metered dose inhalation aerosols using ozone-friendly propellants" Spray Technol. Market. 4:26-29 (1994).
Tibby, et al., "Exogenous surfactant supplementation in infants with respiratory syncytial virus bronciolitis" Am J Respir Crit Care Med., 162(4 Pt 1):1251 (2000).
Timsina, et al., Drug Delivery to the respiratory tract using dry powder inhalers Int. J. Pharm., 101:1-13 (1995).
Tsurumi et al., "Effect of high salt treatment on influenza B viral protein synthesis in MDCK cells," Microbiology and immunology, 1983, 27(6), pp. 519-529 (Full document).
Ulcerative Colitis: Inflammatory bowel Disease (n.d.) retrieved from http://adam.about.com/reports/000069_1.htm.
Vehring, "Pharmaceutical Particle Engineering via Spray Drying" Pharma. Res., vol. 25, No. 5, May 2008.
Vinnikov, et al., "Aerosol Inhalations of Calcium Chloride in Combination Therapy of Pulmonary Tuberculosis," Kazanskii Meditsinskii Zhurnal (1962), vol. 4, pp. 7-9 (translation included).
Visser, "Van der Waals and other cohesive forces affecting powder fluidization", Powder Technology, 58:1-10 (1989).
Vollenbroich, et al., "Mechanism of inactivation of enveloped viruses by the biosurfactin from Bacillus subtilis" Biologicals, 25(3):289-97 (1997).
Wade, C.E., "Hypertonic saline resuscitation in sepsis," Critical Care, Oct. 2002, 6(5), 397-398.
Wark, Rab, McDonald V. Nebulized hypertonic saline for cystic fibrosis (Cochrane Review). In: The Cochrane Library. Oxford, UK: Update Software, 2005.
Watanabe et al., "Why Inhaling Salt Water Changes What We Exhale," Journal of Colloid and Interface Science, 307, pp. 71-78 (2007).
Watanabe, et al., "Immunogenicity and protective efficacy of replication-incompetent influenza virus-like particles" Journal of Virology 76(2):767-773 (2002).
Wikipedia, "Hypertonic" Wikipedia, 2006, accessed Nov. 21, 2006 (en.wikipedia.org/wiki/Hypertonic).
Williams, "Portal to the interior: viral pathogenesis and natural compounds that restore mucosal immunity and modulate inflammation", Alternative Medicine Review, 8(4):395-409 (2003).
Zanen and Lamm, "The optimal particle size for parasymathicolytic aerosols in mild asthmatics", J. Int. J. Pharm., 114:111-115 (1995).
Zasadzinski, et al., "The physics and physiology of lung surfactants", Current Opinion in Colloid & Interface Science, 6:506-513 (2001).
Zayas, et al., "A new paradigm in respiratory hygiene: modulating respiratory secretions to contain cough bioaerosol without affecting mucus clearance," BMC Pulm. Med., 11 (2007).
Shur, Jagdeep, et al., "Cospray-Dried Unfractionated Heparin With L-Leucine as a Dry Powder Inhaler Mucolytic for Cystic Fibrosis Therapy," J. Pharm Sci., 97:4857-4868 (2008).
Arold, et al., "Efficacy of Fluticasone and Salmeterol in a Novel Dry Powder Delivery Platform," ATS 2011 Meeting, Abstract #C22 (May 15, 2011).
Arold, et al., "A Novel Inhaled Dry Powder Delivery Platform; Efficacy of Fluticasone and Salmeterol during Allergic Asthma," ISAM 2011 Meeting, Poster (Apr. 6, 2011).
Arold, et al., "A Novel Inhaled Dry Powder Delivery Platform; Efficacy of Fluticasone and Salmeterol during Allergic Asthma," ISAM 2011 Meeting, Abstract (Apr. 6, 2011).
Sung, "A Novel Platform for DP Inhalation Drugs," 2011 Manufacturing Chemist J article Nov. 7, 2011, accessed online on Jan. 11, 2013.
Arold, et al., "iSPERSE: A Novel Inhaled Dry Powder Delivery Platform for the Delivery of Large Molecule Drugs to the Lung for Local and Systemic Treatments," ATS 2012 Meeting, Abstract (May 18, 2012).
Sung, et al., "Pulmonary Delivery of Combination Drug Products via a Novel Dry Powder Delivery Technology," US-Japan Drug Delivery Symposium 2011, Abstract (Dec. 16, 2011).
Sung, et al., "Pulmonary Delivery of Combination Drug Products via a Novel Dry Powder Delivery Technology," US-Japan Drug Delivery Symposium 2011, Poster (Dec. 16, 2011).
Manzanedo, et al., "Formulation Characterization of a Novel Levofloxacin Pulmonary Dry Powder Drug Delivery Technology," RDD 2012 Meeting, Abstract (May 13, 2012).
Manzanedo, et al., "Formulation Characterization of a Novel Levofloxacin Pulmonary Dry Powder Drug Delivery Technology," RDD 2012 Meeting, Poster (May 13, 2012).
Lawlor, et al., "Development of iSPERSE™ Based Platform for the Delivery of Macromolecules via Dry Powder Formulations," RDD 2012 Meeting, Abstract (May 13, 2012).
Lawlor, et al., "Development of iSPERSE™ Based Platform for the Delivery of Macromolecules via Dry Powder Formulations," RDD 2012 Meeting, Poster (May 13, 2012).
Manzanedo, et al., "Novel Respiratory Dry Powder Drug Delivery Technology for High Drug Load LABA/LAMA," AAPS 2012 Meeting, Abstract (May 21, 2012).
Sung, "A Next-Generation Inhaled Dry Powder Delivery Platform," Drug Development & Delivery, Jul./Aug. 2012, journal article.
"Sung, ""New Formulation Expands Potential for Pulmonary and Systemic Therapies,"" Pharmaceutical Formulation & Quality (PFQ), Dec. 2011/Jan. 2012, Journal Article, accessed online Jan. 11, 2013."
Lawlor, "A High Load Macromolecule Delivery Platform for Pulmonary Dry Powder Drug Delivery," AAPS 2012 Meeting, Poster (May 21, 2012).
Edwards, et al., "Novel Inhalants for Control and Protection Against Airborne Infections," RDD 2006 Meeting, Abstract, (Apr. 23, 2006).
Sung, et al., "iSPERSE™: Formulation and In Vitro Characterization of a Novel Dry Powder Drug Delivery Technology," RDD Europe 2011 Meeting, Poster, (May 3, 2011).
Sung, et al., "iSPERSE™: Formulation and In Vitro Characterization of a Novel Dry Powder Drug Delivery Technology," RDD Europe 2011 Meeting, Abstract, (May 3, 2011).
Problemy Tuberkuleza, 58(1):40-41 (1980).
Communication Pursuant to Article 94(3) EPC, Jul. 4, 2008, EP06759085, 5 pgs.
Communication Pursuant to Article 94(3) EPC, Dec. 2, 2009 EP06759085, 3 pgs.
First Office Action issued by Chinese Patent Office, Application No. 200680019893.8 (with English translation), 9 pgs.
A.D.A.M Healthcare Center, Ulcerative Colitis: Inflammatory Bowel Disease (n.d.) Retrieved from the Internet: http://adam.about.com/reports/000069_1htm (2006).
Buck, "Defensis' Offensive Play: Exploiting a Viral Achilles' Heel," Cell Host & Microbe, vol. 3, No. 1, pp. 3-4, Jan. 17, 2008.
Everaerts, et al., "The Vanilloid Transient Receptor Potential Channel TRPV4: From Structure to Disease," Progress in Biophysics and Molecular Biology, 103:2-17, (2010).
Finlay, The Mechanics of Inhaled Pharmaceutical Aerosols, Academic Press, 143-149 (2001).
Gu, et al., "2-Aminoethoxydiphenyl Borate Stimulates Pulmonary C Neurons Via the Activation of TRPV Channels," American J. of Physiology—Lung Cellular and Molecular Physiology, 288:L932-L941 (2005).
European Search Report from corres. Euro. Appl. No. EP10014830, dated Feb. 11, 2011.
European Search Report from corres. Euro. Appl. No. 11177874, dated Nov. 21, 2011.
Intl Prelim. Report on Patentability, dated Nov. 6, 2007, Intl Application No. PCT/US2006/017248.
International Preliminary Report on Patentability, dated Nov. 18, 2007, from corres. PCT Appl. No. PCT/US2006/019443.

(56) References Cited

OTHER PUBLICATIONS

International Search Report, dated Sep. 29, 2010, from corres. PCT Appl. No. PCT/US2010/028900.
International Search Report, dated Sep. 24, 2010, from corres. PCT Appl. No. PCT/US2010/028901.
International Search Report, dated Sep. 6, 2010, from corres. PCT Appl. No. PCT/US2010/028906.
International Search Report, dated Sep. 15, 2010, from corres. PCT Appl. No. PCT/OS2010/028914.
Intl Search Report, dated Dec. 17, 2010, from corres. PCT Application No. PCT/US2010/028961.
Intl Search Report, dated Dec. 1, 2011, from corres. PCT Application No. PCT/US2011/049342.
Intl Search Report, dated Apr. 17, 2012, from corres. PCT Application No. PCT/US2011/044628.
Intl Search Report, dated Nov. 22, 2011, from corres. PCT Application No. PCT/US2011/049333.
Intl Search Report, dated Mar. 8, 2012, from corres. PCT Application No. PCT/US2011/049435.
Intl Search Report, dated Feb. 9, 2012, from corres. PCT Application No. PCT/US2011/053833.
Intl Search Report, dated May 18, 2012, from corres. PCT Application No. PCT/US2011/059330.
Intl Search Report, dated Mar. 12, 2013, from corres. PCT Application No. PCT/US2012/059022.
Intl Search Report dated Sep. 6, 2013 from corres. PCT Application No. PCT/US2013/028261.
Kulkarni, et al., "Formulation and Characterization of Nasal Sprays," Inhalation Magazine, 6(3):10-15 (2012).
Liedtke, et al., "A Possible Role for TRP4 Receptors in Asthma," American J. of Physiolog—Lung Cellular and Molecular Physiology,287:L269-L271 (2004).
Link, et al., "TRPV2 Has a Pivotal Role in Macrophage Particle Binding and phagocytosis," Nature Immunology, 11:232-239 (2010).
Lorenzo, et al., "TRPV4 Channel participates in Receptor-Operated Calcium Entry and Ciliary Beat Frequency Rgulation in Mouse Airway Epithelial Cells, Proceedings of the Natl Academy of Sciences of the United States of America," 12611 (2008).
Nilius, et al., "Transient Receptor Potential Cation Channels in Disease," Physiological Reviews, 87:165-217 (2007).
Rodwell, et al., "The effect of inhaled frusemide on airway sensitivity to inhaled 4.5% sodium chloride aerosol in asthmatic subject," Thorax (1993) 48:208-213.
Smith, et al., "Mechanism of Adenovirus neutralization by Human Alpha-defensins," Cell Host & Microbe, vol. 3., No. 1, pp. 11-19, Jan. 17, 2008.
Vincent, et al., Identification and Characterization of Novel TRPV4 Mudulators, Biochemical and Biophysical Research Communicaton, 389:490-494 (2009).
Yanire, Andrade, et al., "TRPV4 Channel is Involved in the Coupling of Fluid Viscosity Changes to Epithelial Ciliary Activity," J. Cell Biology, 168:869-874 (2005).
Ghoroi et al., "Dispersion of fine and ultrfine powder through surface modification and rapid expansion," Chemical Engineering Science, vol. 85, pp. 11-24, Jan. 14, 2013.
International Search Report dated Dec. 14, 2011 from corresponding PCT Application No. PCT/US2011/053829.

* cited by examiner

MONOVALENT METAL CATION DRY POWDERS FOR INHALATION

RELATED APPLICATIONS

This application is a continuation of Ser. No. 13/876,312, filed on Jun. 4, 2013, which is a National Stage Entry of PCT/US2011/053829, filed Sep. 29, 2011, which claims the benefit of U.S. Provisional Application No. 61/387,883, filed on Sep. 29, 2010 and the benefit of U.S. Provisional Application No. 61/481,879, filed on May 3, 2011, the entire teachings of these applications are incorporated herein by reference.

BACKGROUND OF THE INVENTION

Pulmonary delivery of therapeutic agents can offer several advantages over other modes of delivery. These advantages include rapid onset of drug action, the convenience of patient self-administration, the potential for reduced drug side-effects, ease of delivery, the elimination of needles, and the like. With these advantages, inhalation therapy is capable of providing a drug delivery system that is easy to use in an inpatient or outpatient setting.

Metered dose inhalers (MDIs) are used to deliver therapeutic agents to the respiratory tract. MDIs are generally suitable for administering therapeutic agents that can be formulated as solid respirable dry particles in a volatile liquid under pressure. Opening of a valve releases the suspension at relatively high velocity. The liquid then volatilizes, leaving behind a fast-moving aerosol of dry particles that contain the therapeutic agent. MDIs are reliable for drug delivery to the upper and middle airways but are limited because they typically deliver only low doses per actuation. However, it is the bronchioles and alveoli that are often the site of manifestation of pulmonary diseases such as asthma and respiratory infections.

Liquid aerosol delivery is one of the oldest forms of pulmonary drug delivery. Typically, liquid aerosols are created by an air jet nebulizer, which releases compressed air from a small orifice at high velocity, resulting in low pressure at the exit region due to the Bernoulli effect. See, e.g., U.S. Pat. No. 5,511,726. The low pressure is used to draw the fluid to be aerosolized out of a second tube. This fluid breaks into small droplets as it accelerates in the air stream. Disadvantages of this standard nebulizer design include relatively large primary liquid aerosol droplet size often requiring impaction of the primary droplet onto a baffle to generate secondary splash droplets of respirable sizes, lack of liquid aerosol droplet size uniformity, significant recirculation of the bulk drug solution, and low densities of small respirable liquid aerosol droplets in the inhaled air.

Ultrasonic nebulizers use flat or concave piezoelectric disks submerged below a liquid reservoir to resonate the surface of the liquid reservoir, forming a liquid cone which sheds aerosol particles from its surface (U.S. 2006/0249144 and U.S. Pat. No. 5,551,416). Since no airflow is required in the aerosolization process, high aerosol concentrations can be achieved, however the piezoelectric components are relatively expensive to produce and are inefficient at aerosolizing suspensions, requiring active drug to be dissolved at low concentrations in water or saline solutions. Newer liquid aerosol technologies involve generating smaller and more uniform liquid respirable dry particles by passing the liquid to be aerosolized through micron-sized holes. See, e.g., U.S. Pat. Nos. 6,131,570; 5,724,957; and 6,098,620. Disadvantages of this technique include relatively expensive piezoelectric and fine mesh components as well as fouling of the holes from residual salts and from solid suspensions.

Dry powder inhalation has historically relied on lactose blending to allow for the dosing of particles that are small enough to be inhaled, but aren't dispersible enough on their own. This process is known to be inefficient and to not work for some drugs. For example, the drug loading in the overall dry powder is low due to the presence of the lactose carrier which is typically large and bulky. Several groups have tried to improve on these shortcomings by developing dry powder inhaler (DPI) formulations that are respirable and dispersible and thus do not require lactose blending. Dry powder formulations for inhalation therapy are described in U.S. Pat. No. 5,993,805 to Sutton et al.; U.S. Pat. No. 6,921,527 to Platz et al.; WO 0000176 to Robinson et al.; WO 9916419 to Tarara et al.; WO 0000215 to Bot et al; U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, in keeping the dry powder stored in a dry state, and in developing a convenient, hand-held device that effectively disperses the respirable dry particles to be inhaled in air. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability which considerably diminish dispersibility and the efficiency of dry powder-based inhalation therapies. For example, interparticular Van der Waals interactions and capillary condensation effects are known to contribute to aggregation of dry particles. Hickey, A. et al., "Factors Influencing the Dispersion of Dry Powders as Aerosols", Pharmaceutical Technology, August, 1994.

The propensity for particles to aggregate or agglomerate increases as particle size decreases. In order to deaggregate particles of a smaller size, a relatively larger dispersion energy is needed. This can be described as inhaled flowrate dependency since the degree of dispersion of the agglomerated particles is a function of inhaled flowrate. What this means to a clinician and a patient is that the dose the patient receives varies depending on their inspiratory flowrate.

One example of how the art has dealt with the need for a high dispersion energy is to require the patient to inhale on a passive dry powder inhaler (DPI) at a high inspiratory flow rate. In Anderson, et al. European Respiratory Journal, 1997, November; 10(11):2465-73, micronized sodium chloride was delivered to patients to cause broncho-provocation. Patients were required to breathe forcefully on the DPI in order to receive the broncho-provocative dose. Flowrates of greater than or equal to 50 LPM on a standard DPI and greater than 28 LPM on a high-resistance DPI were required, both produce higher dispersion energies.

Requiring a patient to inspire at a high flowrate is not always possible, or predictable, e.g., due to patient's disease state or physical condition. Previously, the problem of delivering active agents to the respiratory tract at a relatively constant dose across various flowrates was addressed i) by adding large carrier particle (e.g., typically with an average particle size in excess of 40 μm), such as lactose, ii) by manufacturing particles that are large and porous (e.g., tap density of less than 0.4 g/cc), or iii) by using active dry powder devices that apply significant force to disperse the powders. The first method is still subject to significant variability at varying inspiratory flowrates. The second method requires large volumes of powder to deliver a relatively large dose of powder. The third method requires an expensive inhaler to be purchased, that may also be subject to technical failure.

To overcome interparticle adhesive forces, Batycky et al. in U.S. Pat. No. 7,182,961 teach production of so called "aerodynamically light respirable particles," which have a volume median geometric diameter (VMGD) of greater than 5 microns (μm) as measured using a laser diffraction instrument such as HELOS (manufactured by Sympatec, Princeton, N.J.) and a tap density of less than 0.4 g/cc. See Batycky et al., column 4, lines 21-45, and column 7, lines 42-65.

Similar to Batycky, et al., Lipp et al., in U.S. Pat. No. 7,807,200 teach production of "aerodynamically light respirable particles" that possess a tap density of less than 0.4 g/cc. See Lipp et al., column 4, line 65 to column 5, line 47 where the use of a carboxylate moiety, e.g., citric acid and sodium citrate, a multivalent salt, e.g., a divalent salt, and a phospholipid, e.g., a phospholipid that is endogenous to the lung is taught. Due to the presence of the three components, as well as porous nature of the particle, as indicated by a tap density which is less than 0.4 g/cc, the formulations in Lipp et al. would be difficult to prepare with a high loading of active agents.

Another approach to improve dispersibility of respirable particles of average particle size of less than 10 μm, involves the addition of a water soluble polypeptide or addition of suitable excipients (including amino acid excipients such as leucine) in an amount of 50% to 99.9% by weight of the total composition. Eljamal et al., U.S. Pat. No. 6,582,729, column 4, lines 12-19 and column 5, line 55 to column 6, line 31. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. No. 7,601,336 to Lewis et al., U.S. Pat. No. 6,737,044 to Dickinson et al., U.S. Pat. No. 6,546,928 to Ashurst et al., or U.S. Pat. Applications 20090208582 to Johnston et al.

A further limitation that is shared by each of the above methods is that the aerosols produced typically include substantial quantities of inert carriers, solvents, emulsifiers, propellants, and other non-drug material. In general, large quantities of non-drug material are required for effective formation of respirable dry particles small enough for alveolar delivery (e.g. less than 5 microns and preferably less than 3 microns). However, these amounts of non-drug material also serve to reduce the purity and amount of active drug substance that can be delivered. Thus, these methods remain substantially incapable of introducing large active drug dosages accurately to a patient for systemic delivery.

Therefore, there remains a need for the formation of small particle size aerosols that are highly dispersible. In addition, methods that produce aerosols comprising greater quantities of drug and lesser quantities of non-drug material are needed. Finally, a method that allows a patient to administer a unit dosage rapidly with one or two, small volume breaths is needed.

SUMMARY OF THE INVENTION

The invention relates to respirable dry particles that contain one or more monovalent metal cations (such as $Na^+$) and to dry powders that contain the respirable particles. In particular, aspects of the invention relate to respirable dry powders that contain respirable dry particles that comprise a monovalent metal cation salt in an amount of at least about 3% by weight of the dry particle; the respirable dry particles have a volume median geometric diameter (VMGD) of about 10 microns or less and a dispersibility ratio (1/4 bar) of less than about 2 as measured by laser diffraction (RODOS/HELOS system). Respirable dry particles that consist of 10% leucine and 90% NaCl; or 60% leucine and 40% NaCl; and respirable dry particles that contain a divalent metal cation in an amount of 3% or more by weight of the dry particle are not included in the invention. Preferably, the respirable dry particles have a volume median geometric diameter (VMGD) of about 5.0 microns or less.

The respirable dry powder can have a dispersibility ratio (1/4 bar) of less than about 1.5 as measured at the 1 bar and 4 bar dispersion settings on the HELOS/RODOS laser diffraction system. The respirable dry powder can have a Fine Particle Fraction (FPF) of less than 5.6 microns of at least 45% and/or a Fine Particle Fraction (FPF) of less than 3.4 microns of at least 30%, and/or a Fine Particle Fraction (FPF) of less than 5.0 microns of at least 45%. The respirable dry powder can have a mass median aerodynamic diameter (MMAD) of about 5 microns or less.

The monovalent metal cation salt present in the respirable dry particles can have a solubility of ≥0.5 g/L in water or ≥400 g/L in water at 25° C., 1 bar. In some embodiments, the monovalent metal salt is selected from the group consisting of a sodium salt, a potassium salt, a lithium salt, and combinations thereof. Preferred salts include sodium chloride, sodium lactate, sodium citrate, sodium sulfate or combinations thereof. Other preferred salts include potassium chloride, potassium citrate and combinations thereof.

The respirable dry powder can further comprise at least one pharmaceutically acceptable excipient. The excipient can be present in any desired amount. In some embodiments, the excipient is selected from the group consisting of leucine, maltodextrin, mannitol and combinations thereof.

The respirable dry powder can have a tap density of greater than 0.4 g/cc, greater than 0.5 g/cc or greater than 0.6 g/cc.

If desired, the respirable dry powder can comprise a pharmaceutically active agent. The pharmaceutically active agent can be a component of the respirable dry particles, or can be blended with the respirable dry particles. In some embodiments, the pharmaceutically active agent is an antibiotic, a LABA, a LAMA, a corticosteroid, or any combination thereof. In other embodiments, the pharmaceutically active agent is a macromolecule. For example, the macromolecule can be a cytokine, chemokine, growth factor, hormone or antibody.

Aspects of the invention also relate to a method for treating a respiratory disease comprising administering to the respiratory tract of a patient in need thereof an effective amount of a respirable dry powder as described herein.

Aspects of the invention also relate to a method for treating or preventing an acute exacerbation of a respiratory disease comprising administering to the respiratory tract of a patient in need thereof an effective amount of a respirable dry powder as described herein.

Aspects of the invention also relate to a method for treating or preventing an infectious disease of the respiratory tract comprising administering to the respiratory tract of a patient in need thereof an effective amount of a respirable dry powder as described herein.

Aspects of the invention also relate to a dry powder as described herein for use in therapy and for the treatment or prevention of a disease as described herein.

Described herein are respirable dry particles that contain one or more monovalent metal cations (such as $Na^+$ or $K^+$) and dry powders that contain the respirable particles. In particular, aspects of the invention relate to respirable dry powders that contain respirable dry particles that comprise a monovalent metal cation salt in an amount of at least about 3% by weight of the dry particle. The respirable dry particles and respirable dry powders can further contain a pharmaceutically active agent (e.g. therapeutic and/or prophylactic agent). For example, one or more active agents are co-formulated (e.g., co-spray dried, co-freeze-dried, processed via super-critical fluid-based technologies, etc.) with the one or more monovalent salt(s) and optionally one or more excipient(s) to make respirable dry particles. In another example, the respirable dry powders are comprised of respirable dry particles containing the one or more monovalent metal cations, and can be used as carrier particles to deliver one or more pharmaceutically active agents (e.g., as a blend of the respirable dry particles and the one or more pharmaceutically active agents). In a further example, one or more active agents are co-formulated with the one or more monovalent salts to make respirable dry particles. These co-formulated respirable dry particles (comprising a first, second, etc. active agent) can be used as such, or as carrier particles, to deliver one or more additional active agents (a second, third, fourth, etc. active agent). The additional active agent(s) may be, for example, in micronized form. The one or more additional active agent(s) can be the same active agent(s) that are co-formulated in the dry particle, different active agent(s), or a combination thereof.

Suitable active agents include, but are not limited to, mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF). Preferred active agents include, but are not limited to, LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), antibodies (e.g., therapeutic antibodies), hormones (e.g. insulin), cytokines, chemokines, growth factors, and combinations thereof. When the dry powders are intended for treatment of CF, preferred additional active agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof.

The respirable dry particles of the invention are generally small and dispersible, and can be used to administer pharmaceutically active agent to the lungs, including the deep lung, for local action in the lung and/or for absorption through the lung for systemic action. The respirable dry particles can also be large and dispersible.

In certain embodiments, the respirable dry powders and dry particles described herein are small and highly dispersible, and have other properties that enable them to be delivered to the respiratory tract, including the upper airway and the deep lung upon inhalation, such as high dispersibility, flowrate independence and/or minimized oropharyngeal deposition. Accordingly, the dry powders and dry particles described herein are suitable for delivery of pharmaceutically active agents to the upper airway or deep lung for local or systemic activity.

In addition to being small and dispersible, the respirable dry particles are generally monovalent metal cation (e.g., $Na^+$ or $K^+$) dense and/or pharmaceutically active agent dense. For example, the dry particles can contain a high percentage of monovalent metal cation salt (i.e., be dense in monovalent metal cation salt) and/or contain monovalent metal cation salts that dissociate to release two or more moles of monovalent metal cation per mole of salt. Alternatively, or in addition, the dry particles can contain a high percentage of one or more pharmaceutically active agents. Accordingly, in some aspects, the respirable dry particles of the invention may be monovalent metal cation salt (e.g., a sodium salt or a potassium salt) and/or active agent dense and are small and dispersible.

In another aspect, the respirable dry particles are mass dense (e.g. have a tap density or envelope mass density of greater than about 0.4 g/cc, or at least about 0.45 g/cc or greater, about 0.5 g/cc or greater, about 0.55 g/cc or greater, about 0.6 g/cc or greater, about 0.7 g/cc or greater or about 0.8 g/cc or greater), small, and dispersible.

The respirable dry particles are generally small, e.g., they possess a geometric diameter (VMGD) of less than about 10 microns, between 0.5 microns and 10 microns, between 1 micron and 7 microns or between 1 micron and 5 microns. Optionally, the MMAD of the dry powder may be less than 10 microns, less than 5 microns, between 0.5 and 10 microns, more preferably between 1 and 5 microns, more preferably between 1 and 3 microns or between 3 and 5 microns. The particles optionally have a tap density or envelope mass density greater than 0.4 g/cc, greater than 0.45 g/cc, greater than 0.55 g/cc, between 0.45 g/cc and 1.2 g/cc, or between 0.55 g/cc and 1.0 g/cc. They are also generally dispersible.

The respirable dry particles may also be large, e.g., they may possess a VMGD between 10 microns and 30 microns, or between 10 microns and 20 microns. Optionally, the MMAD of the dry powder may be between 0.5 and 10 microns, more preferably between 1 and 5 microns. The particles optionally have a tap density or envelope mass density between 0.01 g/cc and 0.4 g/cc, or between 0.05 g/cc and 0.25 g/cc. They are also generally dispersible.

Respirable dry powders that contain small particles and that are dispersible in air, and preferably dense (e.g., dense in monovalent metal cation and/or pharmaceutically active agent) are a departure from the conventional wisdom. It is well known that the propensity for particles to aggregate or agglomerate increases as particle size decreases. See, e.g., Hickey, A. et al., "Factors Influencing the Dispersion of Dry Powders as Aerosols", Pharmaceutical Technology, August, 1994.

Respirable dry powder and dry particles described herein that are small, dispersible and dense (e.g., dense in monovalent metal cations (e.g., sodium containing salt(s)), active agent) and/or mass dense) provide advantages for administration and/or therapeutic uses. For example, a desired therapeutically effective dose of an active agent can be delivered when a subject inhales a small volume of dry powder. Accordingly, in comparison to conventional dry powders, such as powders that contain lactose carrier particles a smaller amount of powder will need to be administered in order to deliver the desired dose of pharmaceutically active agent. For example, the desired dose can be delivered with one or two inhalations from a capsule-type or blister-type inhaler.

In certain embodiments, provided herein are respirable dry powders that contain respirable particles that are small and dispersible in air without the need for additional energy sources beyond the subject's inhalation. Thus, the respirable dry powders and respirable dry particles can be used to deliver active agents to the respiratory tract, without including large amounts of non-active components (e.g., excipients such as lactose carrier particles) in the particles or powders, or by using devices that apply mechanical forces to disrupt aggregated or agglomerated particles during or just prior to administration. For example, devices such as passive dry powder inhalers may be used to deliver a dry powder comprised of one or more monovalent cation salts and one or more active agents described herein. In some embodiments, the respirable dry powders and respirable dry particles do not include any excipient (e.g., leucine) in the particles or powders.

Provided herein, in certain embodiments, are respirable dry particles that contain one or more divalent metal cation salts, such as magnesium or calcium-containing salts, where the divalent metal cation is present in an amount of less than 3% by weight.

In one aspect, the respirable particles are not only small and highly dispersible, but can contain a large amount of active agent, e.g., 5% or more, 10% or more, 20% or more, 30% or more, 40% or more, 50% or more, 60% or more, 70% or more, 80% or more, 90% or more, 95% or more, or 97% or more by weight of the dry particle. When an excipient is included in the respirable dry powder or particles, the excipient may comprise about, 50% or less by weight, about 40% or less by weight, about 30% or less by weight, about 20% or less by weight, about 12% or less by weight, about 10% or less by weight, about 8% or less by weight, about 5% or less by weight, about 3% or less by weight, about 2% or less by weight or about 1% or less by weight).

DETAILED DESCRIPTION OF THE INVENTION

Figure 1A:
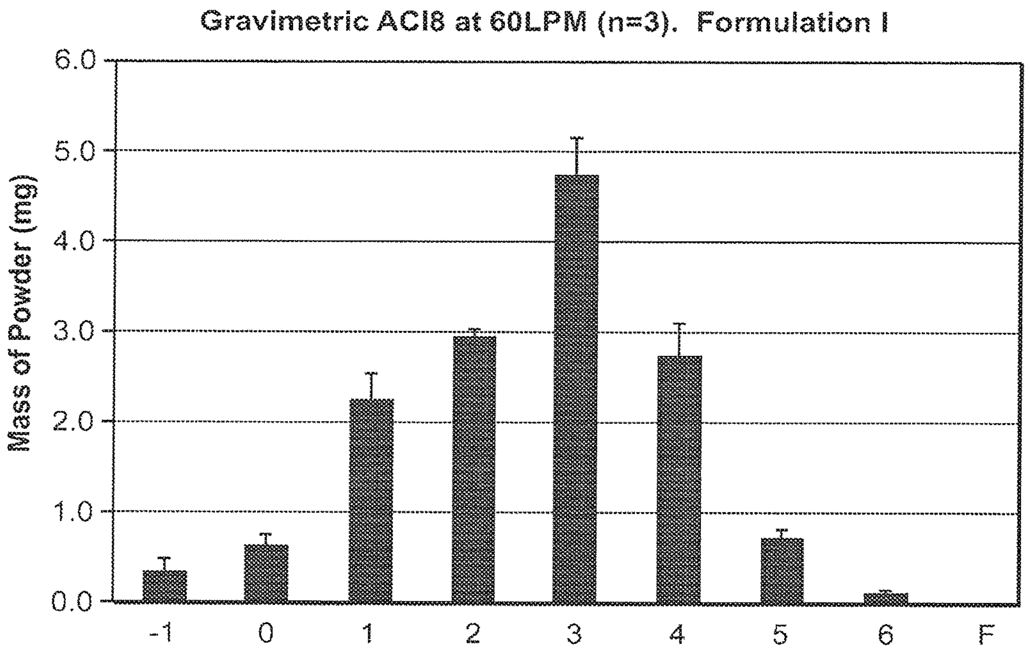
FIGS. 1A-1E are graphs illustrating the aerodynamic particle size distribution of exemplary dry powders of the invention as measured by an eight stage Andersen Cascade Impactor (ACI). The graphs indicate that all five dry powders were of a respirable size.
Figure 1B:
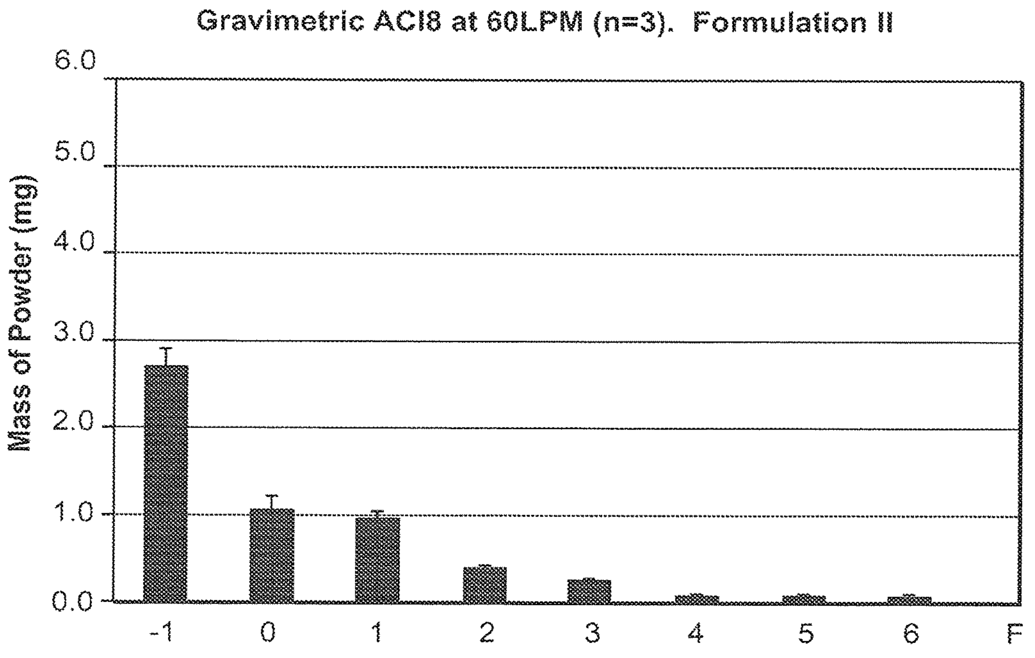
Figure 1C:
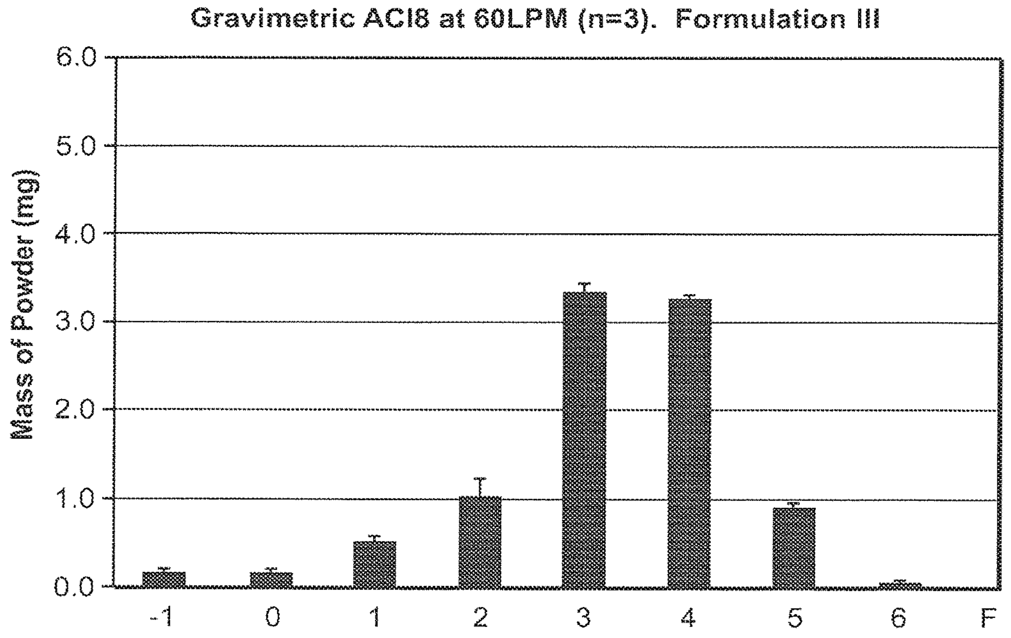
Figure 1D:
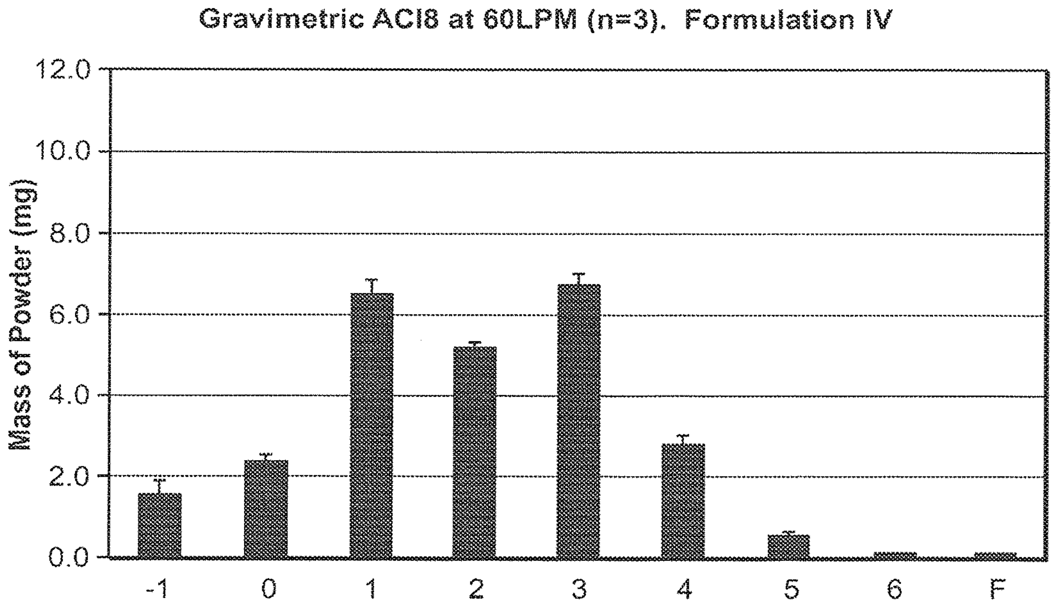
Figure 1E:
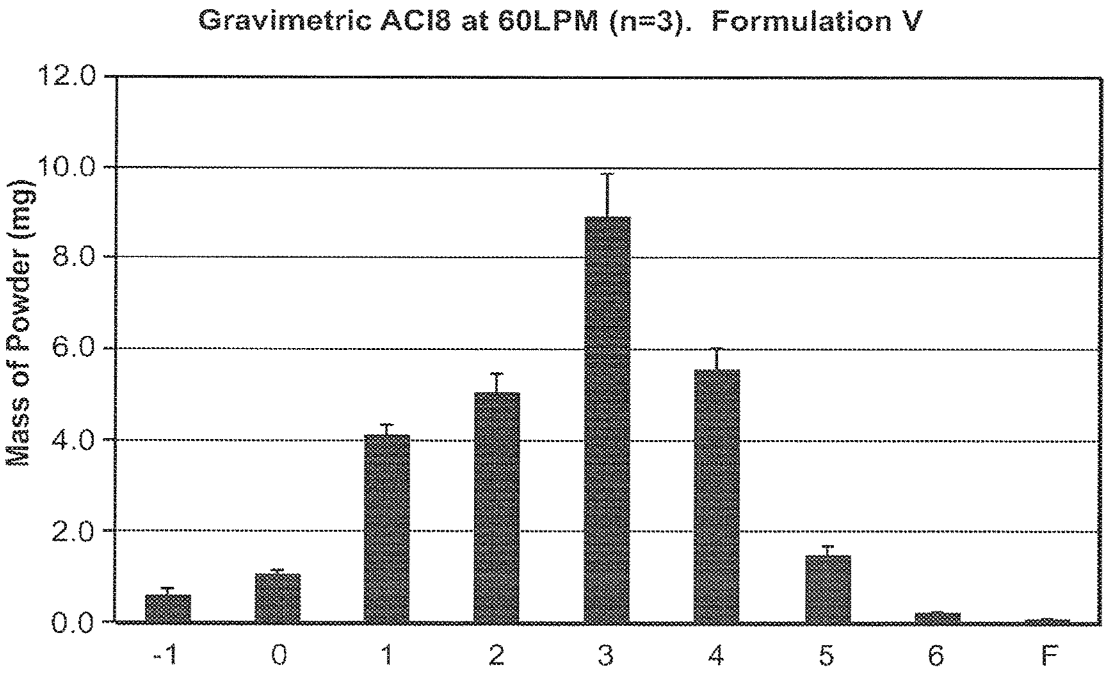

The invention relates to respirable dry particles that contain one or more monovalent metal cations (such as $Na^+$) and to dry powders that contain the respirable particles. The dry particles can further contain a pharmaceutically active agent, or can be used as carrier particles to deliver a pharmaceutically active agent. The respirable dry particles of the invention are generally small and dispersible, and can be used to administer pharmaceutically active agent to the lungs, including the deep lung, for local action in the lung or for absorption through the lung for systemic action.

In addition to being small and dispersible, the respirable dry particles are generally monovalent metal cation (e.g., $Na^+$) dense and/or pharmaceutically active agent dense. Respirable dry powders that contain small particles and that are dispersible in air, and preferably dense (e.g., dense in monovalent metal cation and/or pharmaceutically active agent) are a departure from the conventional wisdom. It is well known that the propensity for particles to aggregate or agglomerate increases as particle size decreases. See, e.g., Hickey, A. et al., "Factors Influencing the Dispersion of Dry Powders as Aerosols", Pharmaceutical Technology, August, 1994.

Provided herein are respirable dry powders that contain respirable particles that are small and dispersible in air without additional energy sources beyond the subject's inhalation. Thus, the respirable dry powders and respirable dry particles can be used to deliver active agents to the respiratory tract, without including large amounts of non-active components (e.g., excipients such as lactose carrier particles) in the particles or powders, or by using devices that apply mechanical forces to disrupt aggregated or agglomerated particles during or just prior to administration.

The respirable dry powders and respirable particles of the invention can be dense in monovalent metal cations (e.g., sodium containing salt(s)) and/or active agent). Thus, in one aspect, the respirable particles are not only small and highly dispersible, but can contain a large amount of monovalent metal cation and/or pharmaceutically active agent. Accordingly, a smaller amount of powder will need to be administered in order to deliver the desired dose of pharmaceutically active agent, in comparison to conventional dry powders, such as powders that contain lactose carrier particles. For example, the desired dose can be delivered with one or two inhalations from a capsule-type or blister-type inhaler.

The respirable dry powders and dry particles described herein are small and highly dispersible, and have other properties that enable them to be delivered to the respiratory tract, including the upper airway and the deep lung upon inhalation, such as high dispersibility, flowrate independence and minimized oropharyngeal deposition. Accordingly, the dry powders and dry particles described herein are suitable for delivering pharmaceutically active agents to the upper airway or deep lung for local or systemic activity.

Definitions

The term "dry powder" as used herein refers to a composition that contains finely dispersed respirable dry particles that are capable of being dispersed in an inhalation device and subsequently inhaled by a subject. Such a dry powder may contain up to about 25%, up to about 20%, or up to about 15% water or other solvent, or be substantially free of water or other solvent, or be anhydrous.

The term "dry particles" as used herein refers to respirable particles that may contain up to about 25%, up to about 20%, or up to about 15% water or other solvent, or be substantially free of water or other solvent, or be anhydrous.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

The term "small" as used herein to describe respirable dry particles refers to particles that have a volume median geometric diameter (VMGD) of about 10 microns or less, preferably about 5 microns or less. VMGD may also be called the volume median diameter (VMD), x50, or Dv50.

As used herein, the terms "administration" or "administering" of respirable dry particles refers to introducing respirable dry particles to the respiratory tract of a subject.

As used herein, the term "respiratory tract" includes the upper respiratory tract (e.g., nasal passages, nasal cavity, throat, and pharynx), respiratory airways (e.g., larynx, trachea, bronchi, and bronchioles) and lungs (e.g., respiratory bronchioles, alveolar ducts, alveolar sacs, and alveoli).

The term "dispersible" is a term of art that describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, VMGD at 0.5 bar divided by the VMGD at 4 bar as measured by HELOS/RODOS, VMGD at 0.2 bar divided by the VMGD at 2 bar as measured by HELOS/RODOS, or VMGD at 0.2 bar divided by the VMGD at 4 bar as measured by HELOS/RODOS. These quotients are referred to herein as "1 bar/4 bar," "0.5 bar/4 bar," "0.2 bar/2 bar," and "0.2 bar/4 bar," respectively, and dispersibility correlates with a low quotient. For example, 1 bar/4 bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a 1 bar/4 bar or 0.5 bar/4 bar ratio that is close to 1.0. Highly dispersible powders have a low tendency to agglomerate, aggregate or clump together and/or, if agglomerated, aggregated or clumped together, are easily dispersed or deagglomerated as they emit from an inhaler and are breathed in by a subject. Dispersibility can also be assessed by measuring the size emitted from an inhaler as a function of flow rate. VMGD may also be called the volume median diameter (VMD), x50, or Dv50.

The terms "FPF (<5.6)," "FPF (<5.6 microns)," and "fine particle fraction of less than 5.6 microns" as used herein, refer to the fraction of a sample of dry particles that have an aerodynamic diameter of less than 5.6 microns. For example, FPF (<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD(<5.6)," where TD means total dose. A similar measurement can be conducted using an eight-stage ACI. The eight-stage ACI cutoffs are different at the standard 60 L/min flow rate, but the FPF_TD(<5.6) can be extrapolated from the eight-stage complete data set. The eight-stage ACI result can also be calculated by the USP method of using the dose collected in the ACI instead of what was in the capsule to determine FPF.

The terms "FPF (<5.0)", "FPF<5 μm", "FPF (<5.0 microns)," and "fine particle fraction of less than 5.0 microns" as used herein, refer to the fraction of a mass of respirable dry particles that have an aerodynamic diameter of less than 5.0 micrometers. For example, FPF (<5.0) can be determined by using an eight-stage ACI at the standard 60 L/min flow rate by extrapolating from the eight-stage complete data set. This parameter may also be identified as "FPF_TD(<5.0)," where TD means total dose. When used in conjunction with a geometric size distribution such as those given by a Malvern Spraytec, Malvern Mastersizer or Sympatec HELOS particle sizer, "FPF (<5.0)" refers to the fraction of a mass of respirable dry particles that have a geometric diameter of less than 5.0 micrometers.

The terms "FPD(<4.4)", 'FPD<4.4 μm", FPD(<4.4 microns)" and "fine particle dose of less than 4.4 microns" as used herein, refer to the mass of respirable dry powder particles that have an aerodynamic diameter of less than 4.4 micrometers. For example, FPD<4.4 μm can be determined by using an eight-stage ACI at the standard 60 L/min flowrate and summing the mass deposited on the filter, and stages 6, 5, 4, 3, and 2 for a single dose of powder actuated into the ACI.

The terms "FPF (<3.4)," "FPF (<3.4 microns)," and "fine particle fraction of less than 3.4 microns" as used herein, refer to the fraction of a mass of respirable dry particles that have an aerodynamic diameter of less than 3.4 microns. For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD(<3.4)," where TD means total dose. A similar measurement can be conducted using an eight-stage ACI. The eight-stage ACI result can also be calculated by the USP method of using the dose collected in the ACI instead of what was in the capsule to determine FPF.

The terms "FPF (<5.0)," "FPF (<5.0 microns)," and "fine particle fraction of less than 5.0 microns" as used herein, refer to the fraction of a mass of respirable dry particles that have an aerodynamic diameter of less than 5.0 microns. For example, FPF (<5.0) can be determined by using an eight-stage ACI at the standard 60 L/min flow rate by extrapolating from the eight-stage complete data set. This parameter may also be identified as "FPF_TD(<5.0)," where TD means total dose.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopeia convention, Rockville, Md., 13$^{th}$ Revision, 222-225, 2007. This method utilizes an in vitro device set up to mimic patient dosing.

The term "capsule emitted powder mass" or "CEPM" as used herein, refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The term "effective amount," as used herein, refers to the amount of active agent needed to achieve the desired therapeutic or prophylactic effect, such as an amount that is sufficient to reduce pathogen (e.g., bacteria, virus) burden, reduce symptoms (e.g., fever, coughing, sneezing, nasal discharge, diarrhea and the like), reduce occurrence of infection, reduce viral replication, or improve or prevent deterioration of respiratory function (e.g., improve forced expiratory volume in 1 second $FEV_1$ and/or forced expiratory volume in 1 second $FEV_1$ as a proportion of forced vital capacity $FEV_1$/FVC, reduce bronchoconstriction), produce an effective serum concentration of a pharmaceutically active agent, increase mucociliary clearance, reduce total inflammatory cell count, or modulate the profile of inflammatory cell counts. The actual effective amount for a particular use can vary according to the particular dry powder or dry particle, the mode of administration, and the age, weight, general health of the subject, and severity of the symptoms or condition being treated. Suitable amounts of dry powders and dry particles to be administered, and dosage schedules for a particular patient can be determined by a clinician of ordinary skill based on these and other considerations.

The term "pharmaceutically acceptable excipient" as used herein means that the excipient can be taken into the lungs with no significant adverse toxicological effects on the lungs. Such excipients are generally regarded as safe (GRAS) by the U.S. Food and Drug Administration.

All references to salts (e.g., sodium containing salts) herein include anhydrous forms and all hydrated forms of the salt.

All weight percentages are given on a dry basis.

Dry Powders and Dry Particles

Aspects of the invention relate to respirable dry powders and dry particles that contain one or more monovalent metal cation salts, preferably one or more sodium salts and/or potassium salts.

Chemical Composition

In one aspect, the respirable dry particles of the invention contain one or more monovalent metal cation salts, such as a sodium salt, a potassium salt and/or a lithium salt, but do not contain a pharmaceutically active agent. These types of respirable dry particles can be used as carrier particles to deliver a pharmaceutically active agent to the respiratory tract (e.g., lungs) for local or systemic delivery. For example, this type of respirable dry particle can be blended with a pharmaceutically active agent, for example in the form of a micronized powder, to produce a dry powder of the invention.

In another aspect, the respirable dry particles of the invention contain one or more monovalent metal cation salts, such as a sodium salt and/or a potassium salt, and further contain a pharmaceutically active agent. These types of respirable dry particles can be prepared, for example, by spray drying a feed stock that contains the monovalent metal cation salt, the pharmaceutically active agent and optionally an excipient, as described herein. This type of dry particle can be used to deliver a pharmaceutically active agent to the respiratory tract (e.g., lungs) for local or systemic delivery.

In a further aspect, the respirable dry particles contain one or more monovalent metal cation salts and one or more active agents. These dry particles can be combined, additionally, with one or more active agents, e.g., by blending, to form a respirable dry powder.

The invention excludes respirable dry powders and respirable dry particles that consist of 10% leucine and 90% NaCl; or 60% leucine and 40% NaCl. The invention also excludes respirable dry powders and respirable dry particles that contain a divalent metal cation (e.g., in the form of a salt) in an amount of 3% or more or that contain a divalent metal cation salt in an amount of 5% or more. In some embodiments, the respirable dry powders and respirable dry particles do not include sodium chloride. In some embodiments, the respirable dry powders and respirable dry particles do not include sodium citrate or citric acid. In some embodiments, the respirable dry powders and respirable dry particles do not include potassium phosphate. In some embodiments, the respirable dry powders and respirable dry particles do not include potassium sulfate. In some embodiments, the respirable dry powders and respirable dry particles do not include a phospholipid as an excipient. Some examples of phospholipids include dipalmitoylphosphatidylcholine (DPPC) and 1.2-distearoyl-sn-glycero-3-phosphocholine (DSPC). In some embodiments, the respirable dry powders and respirable dry particles do not include a surfactant as an active agent. Some examples of surfactants include phospholipids such as dipalmitoylphosphatidylcholine (DPPC) and 1.2-distearoyl-sn-glycero-3-phosphocholine (DSPC). In some embodiments, the respirable dry powders and respirable dry particles do not include lactose as an excipient. In some embodiments, the respirable dry powders and respirable dry particles do not include leucine as an excipient. In some embodiments, the respirable dry powders and respirable dry particles do not include mannitol as an excipient. In some embodiments, the respirable dry powders and respirable dry particles do not include a divalent salt. Examples of divalent salts include a calcium salt and a magnesium salt.

Preferred monovalent metal salts (e.g., sodium salts, potassium salts) have one, or preferably two or more of the following characteristics: (i) can be processed into respirable dry powders, (ii) possess sufficient physicochemical stability in dry powder form to facilitate the production of a powder that is dispersible and physically stable over a range of conditions, including upon exposure to elevated humidity, (iii) undergo rapid dissolution upon deposition in the lungs, for example, half of the mass of the cation of the monovalent metal salt can be dissolved in less than 30 minutes, less than 15 minutes, less than 5 minutes, less than 2 minutes, less than 1 minute, or less than 30 seconds, and (iv) do not possess properties that can result in poor tolerability or adverse events, such as a significant exothermic or endothermic heat of solution ($\Delta H$) for example, a $\Delta H$ lower than of about −10 kcal/mol or greater than about 10 kcal/mol. Rather, a preferred $\Delta H$ is between about −9 kcal/mol and about 9 kcal/mol, between about −8 kcal/mol and about 8 kcal/mol, between about −7 kcal/mol and about 7 kcal/mol, between about −6 kcal/mol and about 6 kcal/mol, between about −5 kcal/mol and about 5 kcal/mol, between about −4 kcal/mol and about 4 kcal/mol, between about −3 kcal/mol and about 3 kcal/mol, between about −2 kcal/mol and about 2 kcal/mol, between about −1 kcal/mol and about 1 kcal/mol, or about 0 kcal/mol.

Suitable sodium, potassium and lithium salts can have desired solubility characteristics. In general, highly or moderately soluble sodium and potassium salts are preferred. For example, sodium and potassium salts that are contained in the respirable dry particles and dry powders can have a solubility in distilled water at room temperature (20-30° C.) and 1 bar of at least about 0.4 g/L, at least about 0.85 g/L, at least about 0.90 g/L, at least about 0.95 g/L, at least about 1.0 g/L, at least about 2.0 g/L, at least about 5.0 g/L, at least about 6.0 g/L, at least about 10.0 g/L, at least about 20 g/L, at least about 50 g/L, at least about 90 g/L, at least about 120 g/L, at least about 500 g/L, at least about 700 g/L or at least about 1000 g/L. Preferably, the sodium and potassium salts have a solubility greater than about 0.90 g/L, greater than about 2.0 g/L, or greater than about 90 g/L. Alternatively, the sodium and potassium salts that are contained in the respirable dry particles and dry powders can have a solubility in distilled water at room temperature (20-30° C.) and 1 bar of between at least about 0.4 g/L to about 200 g/L, between about 1.0 g/L to about 120 g/L, between 5.0 g/L to about 50 g/L.

Suitable sodium salts that can be present in the respirable dry particles of the invention include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, dibasic sodium phosphate, sodium phosphate, sodium bisulfite, sodium borate, sodium gluconate, sodium metasilicate, sodium propionate and the like. In a preferred aspect, the dry powders and dry particles include sodium chloride, sodium citrate, sodium lactate, sodium sulfate, or any combination of these salts. In another preferred aspect, the dry powders and dry particles include sodium lactate, sodium sulfate, or any combination of these salts. In another aspect, the dry powders and dry particles include sodium acetate, sodium carbonate, sodium gluconate, or any combination of these salts.

Suitable potassium salts include, for example, potassium chloride, potassium citrate, potassium bromide, potassium iodide, potassium bicarbonate, potassium nitrite, potassium persulfate, potassium sulfite, potassium sulfate, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium sodium tartrate and any combination thereof. For example, the dry powders and dry particles include potassium chloride, potassium citrate, potassium phosphare, potassium sulfate, or any combination of these salts. In a preferred aspect, the dry powders and dry particles include potassium chloride and/or potassium citrate.

Suitable lithium salts include, for example, lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate or and combination thereof.

Dry powder and particles of the invention can contain a high percentage of sodium salt and/or potassium salt in the composition, and can be sodium cation ($Na^+$) and/or potassium cation ($K^+$) dense. The dry particles may contain 3% or more, 5% or more, 10% or more, 15% or more, 20% ore more, 25% or more, 30% or more, 35% or more, 40% or more, 50% or more, 60% or more, 70% or more, 75% or more, 80% or more, 85% or more, 90% or more, or 95% or more sodium salt or potassium salt by weight.

Alternatively or in addition, the respirable dry particles of the invention can contain a monovalent metal cation salt (e.g., sodium salt or potassium salt), which provides monovalent cation (e.g., $Na^+$ or $K^+$) in an amount of at least about 3% by weight of the respirable dry particles. For example, the respirable dry particles of the invention can include a sodium salt or potassium salt which provides $Na^+$ or $K^+$, in an amount of at least about 5% by weight, at least about 7% by weight, at least about 10% by weight, at least about 11% by weight, at least about 12% by weight, at least about 13% by weight, at least about 14% by weight, at least about 15% by weight, at least about 17% by weight, at least about 20% by weight, at least about 25% by weight, at least about 30% by weight, at least about 35% by weight, at least about 40% by weight, at least about 45% by weight, at least about 50% by weight, at least about 55% by weight, at least about 60% by weight, at least about 65% by weight or at least about 70% by weight of the respirable dry particles.

In some embodiments, the dry particles are small, dispersible, and preferably dense in either monovalent metal cation (e.g., sodium, potassium), dense in monovalent metal cation salt (e.g. contain at least about 30% or at least about 40% (w/w) monovalent metal cation salt), and/or active agent dense. In a further aspect of the invention, the dry particles are small, dispersible, and dense in mass (e.g. tap density, envelope mass density). In this last aspect, the particles can be dense in monovalent metal cation salt (e.g. sodium, potassium), or can have low loading of metal cation salt in the formulation.

If desired, the respirable dry particles of the invention contain one or more other salts in addition to the sodium salt and/or potassium salt, such as one or more non-toxic salts of the elements magnesium, calcium, aluminum, silicon, scandium, titanium, vanadium, chromium, cobalt, nickel, copper, manganese, zinc, tin, silver and the like.

Suitable magnesium salts that can be present in the respirable dry particles described herein include, for example, magnesium fluoride, magnesium chloride, magnesium bromide, magnesium iodide, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof. In a preferred aspect, the dry powder or dry particles include magnesium sulfate, magnesium lactate, magnesium chloride, magnesium citrate, and magnesium carbonate. Preferred magnesium salts are magnesium sulfate and magnesium lactate.

Suitable calcium salts that can be present in the respirable dry particles described herein include, for example, calcium chloride, calcium sulfate, calcium lactate, calcium citrate, calcium carbonate, calcium acetate, calcium phosphate, calcium alginate, calcium stearate, calcium sorbate, calcium gluconate and the like. In certain preferred aspects, the dry powder or dry particles of the invention do not contain calcium phosphate, calcium citrate, and/or calcium chloride.

When the respirable dry particles of the invention contain a divalent metal cation salt, such as a calcium salt or magnesium salt, and a monovalent cation salt, the divalent cation, as a component of one or more salts, is present in an amount of less than 5% by weight of dry particle, less than 3% by weight of dry particle, between 0.01% to about 2.9% by weight of dry particle, or between 0.1% to 2.9% by weight of dry particle.

The respirable dry particles of the invention can contain one or more monovalent metal cation salts (e.g., sodium salts and/or potassium salts) in a total amount of about 1% to about 20% by weight of the respirable dry particles, about 21% to about 60% by weight of the respirable dry particles, or about 61% to about 100% by weight of the respirable dry particles. For example, the respirable dry particles of the invention can include one or more of the monovalent metal cation salts (e.g., sodium salts and/or potassium salts) in a total amount of between about 1% and about 5%, about 5% and about 25%, about 5% and about 15%, about 21% and about 50%, about 21% and about 40%, about 30% and about 40%, about 30% and about 50%, about 61% and about 99%, about 61% and about 90%, about 70% and about 100%, about 70% and about 99%, or about 80% and about 99% by weight of the respirable dry particles.

If desired, the respirable dry particles described herein can include a physiologically or pharmaceutically acceptable excipient. For example, a pharmaceutically-acceptable excipient includes any of the standard carbohydrates, sugar alcohols, and amino acids that are known in the art to be useful excipients for inhalation therapy, either alone or in any desired combination. These excipients are generally relatively free-flowing particulates, do not thicken or polymerize upon contact with water, are toxicologically innocuous when inhaled as a dispersed powder and do not significantly interact with the active agent in a manner that adversely affects the desired physiological action. Carbohydrate excipients that are useful in this regard include the mono- and polysaccharides. Representative monosaccharides include carbohydrate excipients such as dextrose (anhydrous and the monohydrate; also referred to as glucose and glucose monohydrate), galactose, mannitol, D-mannose, sorbose and the like. Representative disaccharides include lactose, maltose, sucrose, trehalose and the like. Representative trisaccharides include raffinose and the like. Other carbohydrate excipients include maltodextrin and cyclodextrins, such as 2-hydroxypropyl-beta-cyclodextrin can be used as desired. Representative sugar alcohols include mannitol, sorbitol and the like.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cysteine, glycine, glutamine, serine, threonine, and tyrosine. Representative examples of polar, positively charged amino acids include arginine, histidine and lysine. Representative examples of negatively charged amino acids include aspartic acid and glutamic acid. These amino acids can be in the D or L optical isomer form, or a mixture of the two forms. These amino acids are generally available from commercial sources that provide pharmaceutical-grade products such as the Aldrich Chemical Company, Inc., Milwaukee, Wis. or Sigma Chemical Company, St. Louis, Mo.

Preferred amino acid excipients, such as the hydrophobic amino acid leucine, in the D or L optical form, or a mixture of the two forms, and can be present in the dry particles of the invention in an amount of about 99% or less by weight of respirable dry particles. For example, the respirable dry particles of the invention can contain the amino acid leucine in an amount of about 0.1% to about 10% by weight, 5% to about 30% by weight, about 10% to about 20% by weight, about 5% to about 20% by weight, about 11% to about 50% by weight, about 15% to about 50% by weight, about 20% to about 50% by weight, about 30% to about 50% by weight, about 11% to about 40% by weight, about 11% to about 30% by weight, about 11% to about 20% by weight, about 20% to about 40% by weight, about 51% to about 99% by weight, about 60% to about 99% by weight, about 70% to about 99% by weight, about 80% to about 99% by weight, about 51% to about 90% by weight, about 51% to about 80% by weight, about 51% to about 70% by weight, about 60% to about 90% by weight, about 70% to about 90% by weight, about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight.

Preferred carbohydrate excipients, such as maltodextrin and mannitol, can be present in the dry particles of the invention in an amount of about 99% or less by weight of respirable dry particles. For example, the respirable dry particles of the invention can contain maltodextrin in an amount of about 0.1% to about 10% by weight, 5% to about 30% by weight by weight, about 10% to about 20% by weight by weight, about 5% to about 20% by weight, about 11% to about 50% by weight, about 15% to about 50% by weight, about 20% to about 50% by weight, about 30% to about 50% by weight, about 11% to about 40% by weight, about 11% to about 30% by weight, about 11% to about 20% by weight, about 20% to about 40% by weight, about 51% to about 99% by weight, about 60% to about 99% by weight, about 70% to about 99% by weight, about 80% to about 99% by weight, about 51% to about 90% by weight, about 51% to about 80% by weight, about 51% to about 70% by weight, about 60% to about 90% by weight, about 70% to about 90% by weight, about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight.

In some preferred aspects, the dry particles contain an excipient selected from leucine, maltodextrin, mannitol and any combination thereof. In particular embodiments, the excipient is leucine, maltodextrin, or mannitol.

Aspects of the invention include respirable dry powders that contain respirable dry particles that contain one or more monovalent metal cation salts, such as a sodium salt and/or a potassium salt, but do not contain a pharmaceutically active agent, that are blended with a pharmaceutically active agent in powder form (e.g., micronized). These particles can be used as carrier particles. The respirable dry powder can include any desired pharmaceutically active agent, such as any of the pharmaceutically active agents described herein.

Aspects of the invention include, respirable dry particles that contain one or more monovalent metal cation salts, such as a sodium salt and/or a potassium salt, and further contain a pharmaceutically active agent, such as any of the pharmaceutically active agents described herein, in a co-formulation.

Suitable pharmaceutically active agents for use in the respirable dry powders and respirable dry particles include mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF).

Preferred active agents include, but are not limited to, LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), antibodies (e.g., therapeutic antibodies), hormones (e.g. insulin), chemokines, cytokines, growth factors, and combinations thereof. When the dry powders are intended for treatment of CF, preferred additional active agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof. In certain embodiments, the pharmaceutically active agent(s) can be blended with the respirable dry particles described herein, or co-formulated (e.g., spray dried) as desired.

In some embodiments, the respirable dry particles and respirable dry powders can contain an agent that disrupts and/or disperses biofilms. Suitable examples of agents to promote disruption and/or dispersion of biofilms include specific amino acid stereoisomers, e.g., D-leucine, D-methionine, D-tyrosine, D-tryptophan, and the like. (Kolodkin-Gal, I., D. Romero, et al. "D-amino acids trigger biofilm disassembly." Science 328(5978): 627-629.) For example, all or a portion of the leucine in the dry powders described herein which contain leucine can be D-leucine.

Examples of suitable mucoactive or mucolytic agents include MUC5AC and MUC5B mucins, DNase, N-acetylcysteine (NAC), cysteine, nacystelyn, dornase alfa, gelsolin, heparin, heparin sulfate, P2Y2 agonists (e.g. UTP, INS365), nedocromil sodium, hypertonic saline, and mannitol.

Suitable surfactants include L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, and alkylated sugars.

If desired, the respirable dry particles and respirable dry powders can contain an antibiotic. The antibiotic can be suitable for treating any desired bacterial infection. The respirable dry particles and respirable dry powders that contain an antibiotic can be used to reduce the spread of infection, either within a patient or from patient to patient. For example, the respirable dry particles and respirable dry powders for treating bacterial pneumonia or VAT, can further comprise an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-*mycobacterium* antibiotics and the like.

If desired, the respirable dry particles and respirable dry powders can contain an agent for treating infections with mycobacteria, such as *Mycobacterium tuberculosis*. Suitable agents for treating infections with mycobacteria (e.g., *M. tuberculosis*) include an aminoglycoside (e.g. capreomycin, kanamycin, streptomycin), a fluoroquinolone (e.g. ciprofloxacin, levofloxacin, moxifloxacin), isozianid and isozianid analogs (e.g. ethionamide), aminosalicylate, cycloserine, diarylquinoline, ethambutol, pyrazinamide, protionamide, rifampin, and the like.

If desired, the respirable dry particles and respirable dry powders can contain a suitable antiviral agent, such as oseltamivir, zanamavir, amantidine, rimantadine, ribavirin, gancyclovir, valgancyclovir, foscavir, Cytogam® (Cytomegalovirus Immune Globulin), pleconaril, rupintrivir, palivizumab, motavizumab, cytarabine, docosanol, denotivir, cidofovir, and acyclovir. The respirable dry particles and respirable dry powders can contain a suitable anti-influenza agent, such as zanamivir, oseltamivir, amantadine, or rimantadine.

Suitable antihistamines include clemastine, asalastine, loratadine, fexofenadine and the like.

Suitable cough suppressants include benzonatate, benproperine, clobutinal, diphenhydramine, dextromethorphan, dibunate, fedrilate, glaucine, oxalamine, piperidione, opiods such as codeine and the like.

Suitable brochodilators include short-acting $beta_2$ agonists, long-acting $beta_2$ agonists (LABA), long-acting muscarinic anagonists (LAMA), combinations of LABAs and LAMAs, methylxanthines, short-acting anticholinergic agents (may also be referred to as short acting anti-muscarinic), long-acting bronchodilators, and the like.

Suitable short-acting $beta_2$ agonists include albuterol, epinephrine, pirbuterol, levalbuterol, metaproteronol, maxair, and the like.

Examples of albuterol sulfate formulations (also called salbutamol) include Inspiryl (AstraZeneca Plc), Salbutamol SANDOZ (Sanofi-Aventis), Asmasal clickhaler (Vectura Group Plc.), Ventolin® (GlaxoSmithKline Plc), Salbutamol GLAND (GlaxoSmithKline Plc), Airomir® (Teva Pharmaceutical Industries Ltd.), ProAir HFA (Teva Pharmaceutical Industries Ltd.), Salamol (Teva Pharmaceutical Industries Ltd.), Ipramol (Teva Pharmaceutical Industries Ltd), Albuterol sulfate TEVA (Teva Pharmaceutical Industries Ltd), and the like. Examples of epinephrine include Epinephine Mist KING (King Pharmaceuticals, Inc.), and the like. Examples of pirbuterol as pirbuterol acetate include Maxair® (Teva Pharmaceutical Industries Ltd.), and the like. Examples of levalbuterol include Xopenex® (Sepracor), and the like. Examples of metaproteronol formulations as metaproteronol sulfate include Alupent® (Boehringer Ingelheim GmbH), and the like.

Suitable LABAs include salmeterol, formoterol and isomers (e.g., arformoterol), clenbuterol, tulobuterol, vilanterol (Revolair™), indacaterol, carmoterol, isoproterenol, procaterol, bambuterol, milveterol, olodaterol, and the like.

Examples of salmeterol formulations include salmeterol xinafoate as Serevent® (GlaxoSmithKline Plc), salmeterol as Inaspir (Laboratorios Almirall, S.A.), Advair® HFA (GlaxoSmithKline PLC), Advair Diskus® (GlaxoSmithKline PLC, Theravance Inc), Plusvent (Laboratorios Almirall, S.A.), VR315 (Novartis, Vectura Group PLC) and the like. Examples of formoterol and isomers (e.g., arformoterol) include Foster (Chiesi Farmaceutici S.p.A), Atimos (Chiesi Farmaceutici S.p.A, Nycomed Internaional Management), Flutiform® (Abbott Laboratories, SkyePharma PLC), MFF258 (Novartis AG), Formoterol clickhaler (Vectura Group PLC), Formoterol HFA (SkyePharma PLC), Oxis® (Astrazeneca PLC), Oxis pMDI (Astrazeneca), Foradil® Aerolizer (Novartis, Schering-Plough Corp, Merck), Foradil® Certihaler (Novartis, SkyePharma PLC), Symbicort® (AstraZeneca), VR632 (Novartis AG, Sandoz International GmbH), MFF258 (Merck & Co Inc, Novartis AG), Alvesco® Combo (Nycomed International Management GmbH, Sanofi-Aventis, Sepracor Inc), Mometasone furoate (Schering-Plough Corp), and the like. Examples of clenbuterol include Ventipulmin® (Boehringer Ingelheim), and the like. Examples of tulobuterol include Hokunalin Tape (Abbott Japan Co., Ltd., Maruho Co., Ltd.), and the like. Examples of vilanterol include Revolair™ (GlaxoSmithKline PLC), GSK64244 (GlaxoSmithKline PLC), and the like. Examples of indacaterol include QAB149 (Novartis AG, SkyePharma PLC), QMF149 (Merck & Co Inc) and the like. Examples of carmoterol include CHF4226 (Chiese Farmaceutici S.p.A., Mitsubishi Tanabe Pharma Corporation), CHF5188 (Chiesi Farmaceutici S.p.A), and the like. Examples of isoproterenol sulfate include Aludrin (Boehringer Ingelheim GmbH) and the like. Examples of procaterol include Meptin clickhaler (Vectura Group PLC), and the like. Examples of bambuterol include Bambec (AstraZeneca PLC), and the like. Examples of milveterol include GSK159797C (GlaxoSmithKline PLC), TD3327 (Theravance Inc), and the like. Examples of olodaterol include BI1744CL (Boehringer Ingelheim GmbH) and the like.

Examples of LAMAs include tiotroprium (Spiriva), trospium chloride, glycopyrrolate, aclidinium, ipratropium and the like.

Examples of tiotroprium formulations include Spiriva® (Boehringer-Ingleheim, Pfizer), and the like. Examples of glycopyrrolate include Robinul® (Wyeth-Ayerst), Robinul® Forte (Wyeth-Ayerst), NVA237 (Novartis), and the like. Examples of aclidinium include Eklira® (Forest Labaoratories, Almirall), and the like.

Examples of combinations of LABAs and LAMAs include indacaterol with glycopyrrolate, formoterol with glycopyrrolate, indacaterol with tiotropium, olodaterol and tiotropium, vilanterol with a LAMA, and the like. Examples of combinations of formoterol with glycopyrrolate include PT003 (Pearl Therapeutics) and the like. Examples of combinations of olodaterol with tiotropium include BI1744 with Spirva (Boehringer Ingelheim) and the like. Examples of combinations of vilanterol with a LAMA include GSK573719 with GSK642444 (GlaxoSmithKline PLC), and the like.

Examples of combinations of indacaterol with glycopyrrolate include QVA149A (Novartis), and the like.

Examples of methylxanthine include aminophylline, ephedrine, theophylline, oxtriphylline, and the like.

Examples of aminophylline formulations include Aminophylline BOEHRINGER (Boehringer Ingelheim GmbH) and the like. Examples of ephedrine include Bronkaid® (Bayer AG), Broncholate (Sanofi-Aventis), Primatene® (Wyeth), Tedral SA®, Marax (Pfizer Inc) and the like. Examples of theophylline include Euphyllin (Nycomed International Management GmbH), Theo-dur (Pfizer Inc, Teva Pharmacetuical Industries Ltd) and the like. Examples of oxtriphylline include Choledyl SA (Pfizer Inc) and the like.

Examples of short-acting anticholinergic agents include ipratropium bromide, and oxitropium bromide.

Examples of ipratropium bromide formulations include Atrovent®/Apovent/Inpratropio (Boehringer Ingelheim GmbH), Ipramol (Teva Pharmaceutical Industries Ltd) and the like. Examples of oxitropium bromide include Oxivent (Boehringer Ingelheim GmbH), and the like.

Suitable anti-inflammatory agents include leukotriene inhibitors, phosphodiesterase 4 (PDE4) inhibitors, other anti-inflammatory agents, and the like.

Suitable leukotriene inhibitors include montelukast formulations (cystinyl leukotriene inhibitors), masilukast, zafirleukast (leukotriene D4 and E4 receptor inhibitors), pranlukast, zileuton (5-lipoxygenase inhibitors), and the like.

Examples of montelukast (cystinyl leukotriene inhibitor) include Singulair® (Merck & Co Inc), Loratadine, montelukast sodium SCHERING (Schering-Plough Corp), MK0476C (Merck & Co Inc), and the like. Examples of masilukast include MCC847 (AstraZeneca PLC), and the like. Examples of zafirlukast (leukotriene D4 and E4 receptor inhibitor) include Accolate® (AstraZeneca PLC), and the like. Examples of pranlukast include Azlaire (Schering- Plough Corp). Examples of zileuton (5-LO) include Zyflo® (Abbott Laboratories), Zyflo CR® (Abbott Laboratories, SkyePharma PLC), Zileuton ABBOTT LABS (Abbott Laboratories), and the like. Suitable PDE4 inhibitors include cilomilast, roflumilast, oglemilast, tofimilast, and the like.

Examples of cilomilast formulations include Ariflo (GlaxoSmithKline PLC), and the like. Examples of roflumilast include Daxas® (Nycomed International Management GmbH, Pfizer Inc), APTA2217 (Mitsubishi Tanabe Pharma Corporation), and the like. Examples of oglemilast include GRC3886 (Forest Laboratories Inc), and the like. Examples of tofimilast include Tofimilast PFIZER INC (Pfizer Inc), and the like.

Other anti-inflammatory agents include omalizumab (anti-IgE immunoglobulin Daiichi Sankyo Company, Limited), Zolair (anti-IgE immunoglobulin, Genentech Inc, Novartis AG, Roche Holding Ltd), Solfa (LTD4 antagonist and phosphodiesterase inhibitor, Takeda Pharmaceutical Company Limited), IL-13 and IL-13 receptor inhibitors (such as AMG-317, MILR1444A, CAT-354, QAX576, IMA-638, Anrukinzumab, IMA-026, MK-6105, DOM-0910, and the like), IL-4 and IL-4 receptor inhibitors (such as Pitrakinra, AER-003, AIR-645, APG-201, DOM-0919, and the like), IL-1 inhibitors such as canakinumab, CRTh2 receptor antagonists such as AZD1981 (CRTh2 receptor antagonist, AstraZeneca), neutrophil elastase inhibitor such as AZD9668 (neutrophil elastase inhibitor, from AstraZeneca), GW856553X Losmapimod (P38 kinase inhibitor, GlaxoSmithKline PLC), Arofylline LAB ALMIRALL (PDE-4 inhibitor, Laboratorios Almirall, S.A.), ABT761 (5-LO inhibitor, Abbott Laboratories), Zyflo® (5-LO inhibitor, Abbott Laboratories), BT061 (anti-CD4 mAb, Boehringer Ingelheim GmbH), Corus (inhaled lidocaine to decrease eosinophils, Gilead Sciences Inc), Prograf® (IL-2-mediated T-cell activation inhibitor, Astellas Pharma), Bimosiamose PFIZER INC (selectin inhibitor, Pfizer Inc), R411 (α4 β1/α4 β7 integrin antagonist, Roche Holdings Ltd), Tilade® (inflammatory mediator inhibitor, Sanofi-Aventis), Orenica® (T-cell co-stimulation inhibitor, Bristol-Myers Squibb Company), Soliris® (anti-C5, Alexion Pharmaceuticals Inc), Entorken® (Farmacija d.o.o.), Excellair® (Syk kinase siRNA, ZaBeCor Pharmaceuticals, Baxter International Inc), KB003 (anti-GMCSF mAb, KaloBios Pharmaceuticals), Cromolyn sodiums (inhibit release of mast cell mediators): Cromolyn sodium BOEHRINGER (Boehringer Ingelheim GmbH), Cromolyn sodium TEVA (Teva Pharmaceutical Industries Ltd), Intal (Sanofi-Aventis), BI1744CL (oldaterol (32-adrenoceptor antagonist) and tiotropium, Boehringer Ingelheim GmbH), NFκ-B inhibitors, CXR2 antagaonists, HLE inhibitors, HMG-CoA reductase inhibitors and the like.

Anti-inflammatory agents also include compounds that inhibit/decrease cell signaling by inflammatory molecules like cytokines (e.g., IL-1, IL-4, IL-5, IL-6, IL-9, IL-13, IL-18 IL-25, IFN-α, IFN-β, and others), CC chemokines CCL-1-CCL28 (some of which are also known as, for example, MCP-1, CCL2, RANTES), CXC chemokines CXCL1-CXCL17 (some of which are also know as, for example, IL-8, MIP-2), growth factors (e.g., GM-CSF, NGF, SCF, TGF-3, EGF, VEGF and others) and/or their respective receptors.

Some examples of the aforementioned anti-inflammatory antagonists/inhibitors include ABN912 (MCP-1/CCL2, Novartis AG), AMG761 (CCR4, Amgen Inc), Enbrel® (TNF, Amgen Inc, Wyeth), huMAb OX40L GENENTECH (TNF superfamily, Genentech Inc, AstraZeneca PLC), R4930 (TNF superfamily, Roche Holding Ltd), SB683699/Firategrast (VLA4, GlaxoSmithKline PLC), CNT0148 (TNFα, Centocor, Inc, Johnson & Johnson, Schering-Plough Corp); Canakinumab (IL-13, Novartis); Israpafant MITSUBISHI (PAF/IL-5, Mitsubishi Tanabe Pharma Corporation); IL-4 and IL-4 receptor antagonists/inhibitors: AMG317 (Amgen Inc), BAY169996 (Bayer AG), AER-003 (Aerovance), APG-201 (Apogenix); IL-5 and IL-5 receptor antagonists/inhibitors: MEDI563 (AstraZeneca PLC, MedImmune, Inc), Bosatria® (GlaxoSmithKline PLC), Cinquil® (Ception Therapeutic), TMC120B (Mitsubishi Tanabe Pharma Corporation), Bosatria (GlaxoSmithKline PLC), Reslizumab SCHERING (Schering-Plough Corp); MEDI528 (IL-9, AstraZeneca, MedImmune, Inc); IL-13 and IL-13 receptor antagonists/inhibitors: TNX650 GENENTECH (Genentech), CAT-354 (AstraZeneca PLC, MedImmune), AMG-317 (Takeda Pharmaceutical Company Limited), MK6105 (Merck & Co Inc), IMA-026 (Wyeth), IMA-638 Anrukinzumab (Wyeth), MILR1444A/Lebrikizumab (Genentech), QAX576 (Novartis), CNTO-607 (Centocor), MK-6105 (Merck, CSL); Dual IL-4 and IL-13 inhibitors: AIR645/ISIS369645 (ISIS Altair), DOM-0910 (GlaxoSmithKline, Domantis), Pitrakinra/AER001/Aerovant™ (Aerovance Inc), AMG-317 (Amgen), and the like.

Suitable steroids include corticosteroids, combinations of corticosteroids and LABAs, combinations of corticosteroids and LAMAs, combinations of corticosteroids, LABAs and LAMAs, and the like.

Suitable corticosteroids include budesonide, fluticasone, flunisolide, triamcinolone, beclomethasone, mometasone, ciclesonide, dexamethasone, and the like.

Examples of budesonide formulations include Captisol-Enabled® Budesonide Solution for Nebulization (AstraZeneca PLC), Pulmicort® (AstraZeneca PLC), Pulmicort® Flexhaler (AstraZeneca Plc), Pulmicort® HFA-MDI (AstraZeneca PLC), Pulmicort Respules® (AstraZeneca PLC), Inflammide (Boehringer Ingelheim GmbH), Pulmicort® HFA-MDI (SkyePharma PLC), Unit Dose Budesonide ASTRAZENECA (AstraZeneca PLC), Budesonide Modulite (Chiesi Farmaceutici S.p.A), CHF5188 (Chiesi Farmaceutici S.p.A), Budesonide ABBOTT LABS (Abbott Laboratories), Budesonide clickhaler (Vestura Group PLC), Miflonide (Novartis AG), Xavin (Teva Pharmaceutical Industries Ltd.), Budesonide TEVA (Teva Pharmaceutical Industries Ltd.), Symbicort® (AstraZeneca K.K., AstraZeneca PLC), VR632 (Novartis AG, Sandoz International GmbH), and the like.

Examples of fluticasone propionate formulations include Flixotide Evohaler (GlaxoSmithKline PLC), Flixotide Nebules (GlaxoSmithKline Plc), Flovent® (GlaxoSmithKline Plc), Flovent® Diskus (GlaxoSmithKline PLC), Flovent® HFA (GlaxoSmithKline PLC), Flovent® Rotadisk (GlaxoSmithKline PLC), Advair® HFA (GlaxoSmithKline PLC, Theravance Inc), Advair Diskus® (GlaxoSmithKline PLC, Theravance Inc.), VR315 (Novartis AG, Vectura Group PLC, Sandoz International GmbH), and the like. Other formulations of fluticasone include fluticasone as Flusonal (Laboratorios Almirall, S.A.), fluticasone furoate as GW685698 (GlaxoSmithKline PLC, Thervance Inc.), Plusvent (Laboratorios Almirall, S.A.), Flutiform® (Abbott Laboratories, SkyePharma PLC), and the like.

Examples of flunisolide formulations include Aerobid® (Forest Laboratories Inc), Aerospan® (Forest Laboratories Inc), and the like. Examples of triamcinolone include Triamcinolone ABBOTT LABS (Abbott Laboratories), Azmacort® (Abbott Laboratories, Sanofi-Aventis), and the like. Examples of beclomethasone dipropionate include Beclovent (GlaxoSmithKline PLC), QVAR® (Johnson & Johnson, Schering-Plough Corp, Teva Pharmacetucial Industries Ltd), Asmabec clickhaler (Vectura Group PLC), Beclomethasone TEVA (Teva Pharmaceutical Industries Ltd), Vanceril (Schering-Plough Corp), BDP Modulite (Chiesi Farmaceutici S.p.A.), Clenil (Chiesi Farmaceutici S.p.A), Beclomethasone dipropionate TEVA (Teva Pharmaceutical Industries Ltd), and the like. Examples of mometasone include QAB149 Mometasone furoate (Schering-Plough Corp), QMF149 (Novartis AG), Fomoterol fumarate, mometoasone furoate (Schering-Plough Corp), MFF258 (Novartis AG, Merck & Co Inc), Asmanex® Twisthaler (Schering-Plough Corp), and the like. Examples of cirlesonide include Alvesco® (Nycomed International Management GmbH, Sepracor, Sanofi-Aventis, Tejin Pharma Limited), Alvesco® Combo (Nycomed International Management GmbH, Sanofi-Aventis), Alvesco® HFA (Nycomed Intenational Management GmbH, Sepracor Inc), and the like. Examples of dexamethasone include DexPak® (Merck), Decadron® (Merck), Adrenocot, CPC-Cort-D, Decaject-10, Solurex and the like. Other corticosteroids include Etiprednol dicloacetate TEVA (Teva Pharmaceutical Industries Ltd), and the like.

Combinations of corticosteroids and LABAs include salmeterol with fluticasone, formoterol with budesonide, formoterol with fluticasone, formoterol with mometasone, indacaterol with mometasone, and the like.

Examples of salmeterol with fluticasone include Plusvent (Laboratorios Almirall, S.A.), Advair® HFA (GlaxoSmithKline PLC), Advair® Diskus (GlaxoSmithKline PLV, Theravance Inc), VR315 (Novartis AG, Vectura Group PLC, Sandoz International GmbH) and the like. Examples of formoterol with budesonide include Symbicort® (AstraZeneca PLC), VR632 (Novartis AG, Vectura Group PLC), and the like. Examples of vilanterol with fluticasone include GSK642444 with fluticasone and the like. Examples of formoterol with fluticasone include Flutiform® (Abbott Laboratories, SkyePharma PLC), and the like. Examples of formoterol with mometasone include Dulera®/MFF258 (Novartis AG, Merck & Co Inc), and the like. Examples of indacaterol with mometasone include QAB149 Mometasone furoate (Schering-Plough Corp), QMF149 (Novartis AG), and the like. Combinations of corticosteroids with LAMAs include fluticasone with tiotropium, budesonide with tiotropium, mometasone with tiotropium, salmeterol with tiotropium, formoterol with tiotropium, indacaterol with tiotropium, vilanterol with tiotropium, and the like. Combinations of corticosteroids with LAMAs and LABAs include, for example, fluticasone with salmeterol and tiotropium.

Other anti-asthma molecules include: ARD111421 (VIP agonist, AstraZeneca PLC), AVE0547 (anti-inflammatory, Sanofi-Aventis), AVE0675 (TLR agonist, Pfizer, Sanofi-Aventis), AVE0950 (Syk inhibitor, Sanofi-Aventis), AVE5883 (NK1/NK2 antagonist, Sanofi-Aventis), AVE8923 (tryptase beta inhibitor, Sanofi-Aventis), CGS21680 (adenosine A2A receptor agonist, Novartis AG), ATL844 (A2B receptor antagonist, Novartis AG), BAY443428 (tryptase inhibitor, Bayer AG), CHF5407 (M3 receptor inhibitor, Chiesi Farmaceutici S.p.A.), CPLA2 Inhibitor WYETH (CPLA2 inhibitor, Wyeth), IMA-638 (IL-13 antagonist, Wyeth), LAS100977 (LABA, Laboratorios Almirall, S.A.), MABA (M3 and β2 receptor antagonist, Chiesi Farmaceutici S.p.A), R1671 (mAb, Roche Holding Ltd), CS003 (Neurokinin receptor antagonist, Daiichi Sankyo Company, Limited), DPC168 (CCR antagonist, Bristol-Myers Squibb), E26 (anti-IgE, Genentech Inc), HAE1 (Genentech), IgE inhibitor AMGEN (Amgen Inc), AMG853 (CRTH2 and D2 receptor antagonist, Amgen), IPL576092 (LSAID, Sanofi-Aventis), EPI2010 (antisense adenosine 1, Chiesi Farmaceutici S.p.A.), CHF5480 (PDE-4 inhibitor, Chiesi Farmaceutici S.p.A.), KI04204 (corticosteroid, Abbott Laboratories), SVT47060 (Laboratorios Salvat, S.A.), VML530 (leukotriene synthesis inhibitor, Abbott Laboratories), LAS35201 (M3 receptor antagonist, Laboratorios Almirall, S.A.), MCC847 (D4 receptor antagonist, Mitsubishi Tanabe Pharma Corporation), MEM1414 (PDE-4 inhibitor, Roche), TA270 (5-LO inhibitor, Chugai Pharmaceutical Co Ltd), TAK661 (eosinophil chemotaxis inhibitor, Takeda Pharmaceutical Company Limited), TBC4746 (VLA-4 antagonist, Schering-Plough Corp), VR694 (Vectura Group PLC), PLD177 (steroid, Vectura Group PLC), KI03219 (corticosteroid+LABA, Abbott Laboratories), AMG009 (Amgen Inc), AMG853 (D2 receptor antagonist, Amgen Inc);

AstraZeneca PLC: AZD1744 (CCR3/histamine-1 receptor antagonist, AZD1419 (TLR9 agonist), Mast Cell inhibitor ASTRAZENECA, AZD3778 (CCR antagonist), DSP3025 (TLR7 agonist), AZD1981 (CRTh2 receptor antagonist), AZD5985 (CRTh2 antagonist), AZD8075 (CRTh2 antagonist), AZD1678, AZD2098, AZD2392, AZD3825 AZD8848, AZD9215, ZD2138 (5-LO inhibitor), AZD3199 (LABA);

GlaxoSmithKline PLC: GW328267 (adenosine A2 receptor agonist), GW559090 (α4 integrin antagonist), GSK679586 (mAb), GSK597901 (adrenergic β2 agonist), AM103 (5-LO inhibitor), GSK256006 (PDE4 inhibitor), GW842470 (PDE-4 inhibitor), GSK870086 (glucocorticoid agonist), GSK159802 (LABA), GSK256066 (PDE-4 inhibitor), GSK642444 (LABA, adrenergic β2 agonist), GSK64244 and Revolair (fluticasone/vilanterol), GSK799943 (corticosteroid), GSK573719 (mAchR antagonist), and GSK573719;

Pfizer Inc: PF3526299, PF3893787, PF4191834 (FLAP antagonist), PF610355 (adrenergic β2 agonist), CP664511 (α4β1/VCAM-1 interaction inhibitor), CP609643 (inhibitor of α4β1/VCAM-1 interactions), CP690550 (JAK3 inhibitor), SAR21609 (TLR9 agonist), AVE7279 (Th1 switching), TBC4746 (VLA-4 antagonist); R343 (IgE receptor signaling inhibitor), SEP42960 (adenosine A3 antagonist);

Sanofi-Aventis: MLN6095 (CrTH2 inhibitor), SAR137272 (A3 antagonist), SAR21609 (TLR9 agonist), SAR389644 (DP1 receptor antagonist), SAR398171 (CRTH2 antagonist), SSR161421 (adenosine A3 receptor antagonist);

Merck & Co Inc: MK0633, MK0633, MK0591 (5-LO inhibitor), MK886 (leukotriene inhibitor), BIO01211 (VLA-4 antagonist); Novartis AG: QAE397 (long-acting corticosteroid), QAK423, QAN747, QAP642 (CCR3 antagonist), QAX935 (TLR9 agonist), NVA237 (LAMA).

The pharmaceutically active agent can also be selected from the group consisting of transient receptor potential (TRP) channel agonists. In certain embodiments, the TRP agonist is a TRPC, TRPV, TRPM and/or TRPA1 subfamily agonist. In some embodiments, the TRP channel agonist is selected from the group consisting of TRPV2, TRPV3, TRPV4, TRPC6, TRPM6, and/or TRPA1 agonist. Suitable TRP channel agonists may be selected from the group consisting of allyl isothiocyanate (AITC), benyzl isothiocyanate (BITC), phenyl isothiocyanate, isopropyl isothiocyanate, methyl isothiocyanate, diallyl disulfide, acrolein (2-propenal), disulfiram (Antabuse®), farnesyl thiosalicylic acid (FTS), farnesyl thioacetic acid (FTA), chlodantoin (Sporostacin®, topical fungicidal), (15-d-PGJ2), 5,8,11,14 eicosatetraynoic acid (ETYA), dibenzoazepine, mefenamic acid, fluribiprofen, keoprofen, diclofenac, indomethacin, SC alkyne (SCA), pentenal, mustard oil alkyne (MOA), iodoacetamine, iodoacetamide alkyne, (2-aminoethyl) methanethiosulphonate (MTSEA), 4-hydroxy-2-noneal (HNE), 4-hydroxy xexenal (HHE), 2-chlorobenzalmalononitrile, N-chloro tosylamide (chloramine-T), formaldehyde, isoflurane, isovelleral, hydrogen peroxide, URB597, thiosulfinate, Allicin (a specific thiosulfinate), flufenamic acid, niflumic acid, carvacrol, eugenol, menthol, gingerol, icilin, methyl salicylate, arachidonic acid, cinnemaldehyde, super sinnemaldehyde, tetrahydrocannabinol (THC or $\Delta^9$-THC), cannabidiol (CBD), cannabichromene (CBC), cannabigerol (CBG), THC acid (THC-A), CBD acid (CBD-A), Compound 1 (AMG5445), 4-methyl-N-[2,2,2-trichloro-1-(4-chlorophenylsulfanyl) ethyl]benzamide, N-[2,2,2-trichloro-1-(4-chlorophenylsulfanyl)ethyl]acetamid, AMG9090, AMG5445, 1-oleoyl-2-acetyl-sn-glycerol (OAG), carbachol, diacylglycerol (DAG), 1,2-Didecanoylglycerol, flufenamate/flufenamic acid, niflumate/niflumic acid, hyperforin, 2-aminoethoxydiphenyl borate (2-APB), diphenylborinic anhydride (DPBA), delta-9-tetrahydrocannabinol ($\Delta^9$-THC or THC), cannabiniol (CBN), 2-APB, O-1821, 11-hydroxy-A9-tetrahydrocannabinol, nabilone, CP55940, HU-210, HU-211/dexanabinol, HU-331, HU-308, JWH-015, WIN55, 212-2, 2-Arachidonoylglycerol (2-AG), Arvil, PEA, AM404, O-1918, JWH-133, incensole, incensole acetate, menthol, eugenol, dihydrocarveol, carveol, thymol, vanillin, ethyl vanillin, cinnemaldehyde, 2 aminoethoxydiphenyl borate (2-APB), diphenylamine (DPA), diphenylborinic anhydride (DPBA), camphor, (+)-borneol, (−)-isopinocampheol, (−)-fenchone, (−)-trans-pinocarveol, isoborneol, (+)-camphorquinone, (−)-α-thujone, α-pinene oxide, 1,8-cineole/eucalyptol, 6-butyl-m-cresol, carvacrol, p-sylenol, kreosol, propofol, p-cymene, (−)-isoppulegol, (−)-carvone, (+)-dihydrocarvone, (−)-menthone, (+)-linalool, geraniol, 1-isopropyl-4-methylbicyclo[3.1.0]hexan-4-ol, 4αPDD, GSK1016790A, 5'6'Epoxyeicosatrienoic (5'6'-EET), 8'9'Epoxyeicosatrienoic (8'9'-EET), APP44-1, RN1747, Formulation Ib WO200602909, Formulation IIb WO200602909, Formulation IIc WO200602929, Formulation IId WO200602929, Formulation IIIb WO200602929, Formulation IIIc WO200602929, arachidonic acid (AA), 12-O-Tetradecanoylphorbol-13-acetate (TPA)/phorbol 12-myristate 13-acetate (PMA), bisandrographalide (BAA), incensole, incensole acetate, Compound IX WO2010015965, Compound X WO2010015965, Compound XI WO2010015965, Compound XII WO2010015965, WO2009004071, WO2006038070, WO2008065666, Formula VII WO2010015965, Formula IV WO2010015965, dibenzoazepine, dibenzooxazepine, Formula I WO2009071631, N-{(1S)-1-[({(4R)-1-[(4-chlorophenyl)sulfonyl]-3-oxohexahydro-1Hazepin-4-yl}amino) carbonyl]-3-methylbutyl}-1-benzothiophen-2-carboxamide, N-{(1S)-1-[({(4R)-1-[(4-fluorophenyl)sulfonyl]-3-oxohexahydro-1H-azepin-4-yl}amino)carbonyl]-3-methylbutyl}-1-benzothiophen-2-carboxamide, N-{(1S)-1-[({(4R)-1-[(2-cyanophenyl)sulfonyl]-3-oxohexahydro-1H-azepin-4-yl}amino)carbonyl]-3-methylbutyl}-1-methyl-1H-indole-2-carboxamide, and N-{(1S)-1-[({(4R)-1-[(2-cyanophenyl) sulfonyl]hexahydro-1H-azepin-4-yl}amino)carbonyl]-3-methylbutyl}-1-methyl-1H-indole-2-carboxamide.

Suitable expectorants include guaifenesin, guaiacolculfonate, ammonium chloride, potassium iodide, tyloxapol, antimony pentasulfide and the like.

Suitable vaccines include nasally inhaled influenza vaccines and the like.

Suitable macromolecules include proteins and large peptides, polysaccharides and oligosaccharides, DNA and RNA nucleic acid molecules and their analogs having therapeutic, prophylactic or diagnostic activities. Proteins can include growth factors, hormones, cytokines (e.g., chemokines), and antibodies. As used herein, antibodies can include: all types of immunoglobulins, e.g. IgG, IgM, IgA, IgE, IgD, etc., from any source, e.g. human, rodent, rabbit, cow, sheep, pig, dog, other mammals, chicken, other avian, aquatic animal species etc., monoclonal and polyclonal antibodies, single chain antibodies (including IgNAR (single-chain antibodies derived from sharks)), chimeric antibodies, bifunctional/bispecific antibodies, humanized antibodies, human antibodies, and complementary determining region (CDR)-grafted antibodies, that are specific for the target protein or fragments thereof, and also include antibody fragments, including Fab, Fab', F(ab')2, scFv, Fv, camelbodies, microantibodies, nanobodies, and small-modular immunopharmaceuticals (SMIPs). Nucleic acid molecules include DNA, e.g. encoding genes or gene fragments, or RNA, including mRNA, antisense molecules, such as antisense RNA, RNA molecules involved in RNA interference (RNAi), such as microRNA (miRNA), small interfering RNA (siRNA) and small hairpin RNA (shRNA), ribozymes or other molecules capable of inhibiting transcription and/or translation. Preferred macromolecules have a molecular weight of at least 800 Da, at least 3000 Da or at least 5000 Da.

In preferred embodiments, the respirable dry powder or respirable dry particle comprises a therapeutic antibody. In certain preferred embodiments, the antibody is a monoclonal antibody. In certain preferred embodiments, the antibody is a single chain antibody, a chimeric antibody, a bifunctional/bispecific antibody, a humanized antibody, or a combination thereof. In preferred embodiments, the antibody is selected from the group consisting of: monoclonal antibodies, e.g. Abciximab (ReoPro®, chimeric), Adalimumab (Humira®, human), Alemtuzumab (Campath®, humanized), Basiliximab (Simulect®, chimeric), Belimumab (Benlysta®, human), Bevacizumab (Avastin®, humanized), Brentuximab vedotin (Adcetris®, chimeric), Canakinumab (Ilaris®, human), Cetuximab (Erbitux®, chimeric), Certolizumab pegol (Cimzia®, humanized), Daclizumab (Zenapax®, humanized), Denosumab (Prolia®, Xgeva®, human), Eculizumab (Soliris®, humanized), Efalizumab (Raptiva®, humanized), Gemtuzumab (Mylotarg®, humanized), Golimumab (Simponi®, human), Ibritumomab tiuxetan (Zevalin®, murin), Infliximab (Remicade®, chimeric), Ipilimumab (MDX-101) (Yervoy®, human), Muromonab-CD3 (Orthoclone OKT3, murine), Natalizumab (Tysabri®, humanized), Ofatumumab (Arzerra®, human), Omalizumab (Xolair®, humanized), Palivizumab (Synagis®, humanized), Panitumumab (Vectibix®, human), Ranibizumab (Lucentis®, humanized), Rituximab (Rituxan®, Mabthera®, chimeric), Tocilizumab (or Atlizumab) (Actemra® and RoActemra®, humanized), Tositumomab (Bexxar®, murine), Trastuzumab (Herceptin®, humanized), and bispecific antibodies, e.g. catumaxomab (Removab®, rat-mouse hybrid monoclonal antibody).

Selected macromolecule active agents for systemic applications include, but are not limited to: Ventavis® (Iloprost), Calcitonin, Erythropoietin (EPO), Factor IX, Granulocyte Colony Stimulating Factor (G-CSF), Granulocyte Macrophage Colony, Stimulating Factor (GM-CSF), Growth Hormone, Insulin, TGF-beta, Interferon Alpha, Interferon Beta, Interferon Gamma, Luteinizing Hormone Releasing Hormone (LHRH), follicle stimulating hormone (FSH), Ciliary Neurotrophic Factor, Growth Hormone Releasing Factor (GRF), Insulin-Like Growth Factor, Insulinotropin, Interleukin-1 Receptor Antagonist, Interleukin-3, Interleukin-4, Interleukin-6, Macrophage Colony Stimulating Factor (M-CSF), Thymosin Alpha 1, IIb/IIIa Inhibitor, Alpha-1 Antitrypsin, Anti-RSV Antibody, palivizumab, motavizumab, and ALN-RSV, Cystic Fibrosis Transmembrane Regulator (CFTR) Gene, Deoxyribonuclase (DNase), Heparin, Bactericidal/Permeability Increasing Protein (BPI), Anti-Cytomegalovirus (CMV) Antibody, Interleukin-1 Receptor Antagonist, and the like, alpha-defensins (e.g. human neutrophil proteins (HNPs): HNP1, 2, 3, and 4; human defensins 5 and 6 (HD5 and HD6)), beta-defensins (HBD1, 2, 3, and 4), or Θ-defensins/retrocyclins, GLP-1 analogs (liraglutide, exenatide, etc.), Domain antibodies (dAbs), Pramlintide acetate (Symlin), Leptin analogs, Synagis (palivizumab, MedImmune) and cisplatin. In certain preferred embodiments, the respirable dry powder or respirable dry particle comprises a macromolecule involved in intra- or inter-cellular signaling, such as a growth factor, a cytokine, a chemokine or a hormone. In preferred embodiments, the respirable dry powder or respirable dry particle comprises a hormone. In certain preferred embodiments, the hormone is insulin.

Selected therapeutics helpful for chronic maintenance of CF include antibiotics/macrolide antibiotics, bronchodilators, inhaled LABAs, and agents to promote airway secretion clearance. Suitable examples of antibiotics/macrolide antibiotics include tobramycin, azithromycin, ciprofloxacin, colistin, aztreonam and the like. Another exemplary antibiotic/macrolide is levofloxacin. Suitable examples of bronchodilators include inhaled short-acting beta$_2$ agonists such as albuterol, and the like. Suitable examples of inhaled LABAs include salmeterol, formoterol, and the like. Suitable examples of agents to promote airway secretion clearance include Pulmozyme (dornase alfa, Genentech) hypertonic saline, DNase, heparin, and the like. Selected therapeutics helpful for the prevention and/or treatment of CF include VX-770 (Vertex Pharmaceuticals) and amiloride.

Selected therapeutics helpful for the treatment of idiopathic pulmonary fibrosis include Metelimumab (CAT-192) (TGF-β1 mAb inhibitor, Genzyme), Aerovant™ (AER001, pitrakinra) (Dual IL-13, IL-4 protein antagonist, Aerovance), Aeroderm™ (PEGylated Aerovant, Aerovance), microRNA, RNAi, and the like.

In preferred embodiments, the respirable dry powder or respirable dry particle comprises an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g. doripenem, ertapenem, imipenem and meropenem), a monobactam (e.g., aztreonam), an oxazolidinone (e.g., linezolid), vancomycin, glycopeptide antibiotics (e.g. telavancin), tuberculosis-*mycobacterium* antibiotics, tobramycin, azithromycin, ciprofloxacin, colistin, and the like. In a preferred embodiment, the respirable dry powder or respirable dry particle comprises levofloxacin. In another preferred embodiment, the respirable dry powder or respirable dry particle comprises aztreonam or a pharmaceutically acceptable salt thereof (i.e., Cayston®). In a further preferred embodiment, the respirable dry powder or respirable dry particle does not comprise tobramycin. In another embodiment, the respirable dry powder or respirable dry particle does not comprise levofloxacin. In another embodiment, the respirable dry powder or respirable dry particle does not comprise Cayston®.

In preferred embodiments, the respirable dry powder or respirable dry particle comprises a LABA, such as salmeterol, formoterol and isomers (e.g., arformoterol), clenbuterol, tulobuterol, vilanterol (Revolair™), indacaterol, carmoterol, isoproterenol, procaterol, bambuterol, milveterol, and the like. In a further preferred embodiment, the respirable dry powder or respirable dry particle comprises formoterol. In a further preferred embodiment, the respirable dry powder or respirable dry particle comprises salmeterol. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

In preferred embodiments, the respirable dry powder or respirable dry particle comprises a LAMA, such as tiotroprium, glycopyrrolate, aclidinium, ipratropium and the like. In a further preferred embodiment, the respirable dry powder or respirable dry particle comprises tiotropium.

In preferred embodiments, the respirable dry powder or respirable dry particle comprises a corticosteroid, such as budesonide, fluticasone, flunisolide, triamcinolone, beclomethasone, mometasone, ciclesonide, dexamethasone, and the like. In a further preferred embodiment, the respirable dry powder or respirable dry particle comprises fluticasone.

In preferred embodiments, the respirable dry powder or respirable dry particle comprises a combination of two or more of the following; a LABA, a LAMA, and a corticosteroid. In a further preferred embodiment, the respirable dry powder or respirable dry particle comprises fluticasone and salmeterol. In a further preferred embodiment, the respirable dry powder or respirable dry particle comprises fluticasone, salmeterol, and tiotropium.

When an additional therapeutic agent is administered to a patient with a dry powder or dry particles disclosed herein, the agent and the dry powder or dry particles are administered to provide overlap of the therapeutic effect of the additional therapeutic agent with the administration of the dry powder or dry particles. For example, a LABA such as formoterol, or a short-acting beta agonist such as albuterol can be administered to the patient before a dry powder or dry particle, as described herein, is administered.

In preferred embodiments, the respirable dry powder or respirable dry particle does not comprise a surfactant, such as L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, or alkylated sugars.

Dry Powder and Dry Particle Properties

The dry particles of the invention are preferably small and dispersible, and can be sodium cation (Na+) and/or potassium cation (K+) dense. Generally, the dry particles of the invention have a VMGD as measured by HELOS/RODOS at 1.0 bar of about 10 μm or less (e.g., about 0.1 μm to about 10 μm). Preferably, the dry particles of the invention have a VMGD of about 9 μm or less (e.g., about 0.1 μm to about 9 μm), about 8 μm or less (e.g., about 0.1 μm to about 8 μm), about 7 μm or less (e.g., about 0.1 μm to about 7 μm), about 6 μm or less (e.g., about 0.1 μm to about 6 μm), about 5 μm or less (e.g., less than 5 μm, about 0.1 μm to about 5 μm), about 4 μm or less (e.g., 0.1 μm to about 4 μm), about 3 μm or less (e.g., 0.1 μm to about 3 μm), about 2 μm or less (e.g., 0.1 μm to about 2 μm), about 1 μm or less (e.g., 0.1 μm to about 1 μm), about 1 μm to about 6 μm, about 1 μm to about 5 μm, about 1 μm to about 4 μm, about 1 μm to about 3 μm, or about 1 μm to about 2 μm as measured by HELOS/RODOS at 1.0 bar.

The respirable dry powders of the invention can have poor flow properties, such as bulk flow properties, for example as assessed by Hausner Ratio, as described herein. Yet, surprisingly, the powders are highly dispersible. This is surprising because flow properties and dispersibility are both known to be negatively affected by particle agglomeration or aggregation. Thus, it was unexpected that particles that have poor flow characteristics, such as bulk flow characteristics, would be highly dispersible.

The respirable dry powders can have a Hausner Ratio that is at least 1.5, and can be at least 1.6, at least 1.7, at least 1.8, at least 1.9, at least 2.0, at least 2.1, at least 2.2, at least 2.3, at least 2.4, at least 2.5, at least 2.6 or at least 2.7.

Generally, the dry particles of the invention are dispersible, and have 1 bar/4 bar and/or 0.5 bar/4 bar and/or 0.2 bar/4 bar and/or 0.2 bar/2 bar of about 2.2 or less (e.g., about 1.0 to about 2.2) or about 2.0 or less (e.g., about 1.0 to about 2.0). Preferably, the dry particles of the invention have 1 bar/4 bar and/or 0.5 bar/4 bar of about 1.9 or less (e.g., about 1.0 to about 1.9), about 1.8 or less (e.g., about 1.0 to about 1.8), about 1.7 or less (e.g., about 1.0 to about 1.7), about 1.6 or less (e.g., about 1.0 to about 1.6), about 1.5 or less (e.g., about 1.0 to about 1.5), about 1.4 or less (e.g., about 1.0 to about 1.4), about 1.3 or less (e.g., less than 1.3, about 1.0 to about 1.3), about 1.2 or less (e.g., 1.0 to about 1.2), about 1.1 or less (e.g., 1.0 to about 1.1 μm) or the dry particles of the invention have 1 bar/4 bar and/or 0.5 bar/4 bar of about 1.0. Preferably 1 bar/4 bar and/or 0.5 bar/4 bar are measured by laser diffraction using a HELOS/RODOS system.

Alternatively or in addition, the respirable dry particles of the invention can have an MMAD of about 10 microns or less, such as an MMAD of about 0.5 micron to about 10 microns. Preferably, the dry particles of the invention have an MMAD of about 5 microns or less (e.g., about 0.5 micron to about 5 microns, preferably about 1 micron to about 5 microns), about 4 microns or less (e.g., about 1 micron to about 4 microns), about 3.8 microns or less (e.g., about 1 micron to about 3.8 microns), about 3.5 microns or less (e.g., about 1 micron to about 3.5 microns), about 3.2 microns or less (e.g., about 1 micron to about 3.2 microns), about 3 microns or less (e.g., about 1 micron to about 3.0 microns), about 2.8 microns or less (e.g., about 1 micron to about 2.8 microns), about 2.2 microns or less (e.g., about 1 micron to about 2.2 microns), about 2.0 microns or less (e.g., about 1 micron to about 2.0 microns) or about 1.8 microns or less (e.g., about 1 micron to about 1.8 microns).

Alternatively or in addition, the respirable dry powders and dry particles of the invention can have an FPF of less than about 5.6 microns (FPF<5.6 μm) of at least about 20%, at least about 30%, at least about 40%, preferably at least about 45%, at least about 50%, at least about 55%, at least about 60%, at least about 65%, or at least about 70%.

Alternatively or in addition, the dry powders and dry particles of the invention have a FPF of less than 5.0 microns (FPF_TD<5.0 μm) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the invention have a FPF of less than 5.0 microns of the emitted dose (FPF_ED<5.0 μm) of at least about 45%, preferably at least about 50%, at least about 60%, at least about 65%, at least about 70%, at least about 75%, at least about 80%, or at least about 85%. Alternatively or in addition, the dry powders and dry particles of the invention can have an FPF of less than about 3.4 microns (FPF<3.4 μm) of at least about 20%, preferably at least about 25%, at least about 30%, at least about 35%, at least about 40%, at least about 45%, at least about 50%, or at least about 55%.

Alternatively or in addition, the respirable dry powders and dry particles of the invention have a tap density of about 0.1 $g/cm^3$ to about 1.0 $g/cm^3$. For example, the small and dispersible dry particles have a tap density of about 0.1 $g/cm^3$ to about 0.9 $g/cm^3$, about 0.2 $g/cm^3$ to about 0.9 $g/cm^3$, about 0.2 $g/cm^3$ to about 0.9 $g/cm^3$, about 0.3 $g/cm^3$ to about 0.9 $g/cm^3$, about 0.4 $g/cm^3$ to about 0.9 $g/cm^3$, about 0.5 $g/cm^3$ to about 0.9 $g/cm^3$, or about 0.5 $g/cm^3$ to about 0.8 $g/cm^3$, greater than about 0.4 g/cc, greater than about 0.5 g/cc, greater than about 0.6 g/cc, greater than about 0.7 g/cc, about 0.1 $g/cm^3$ to about 0.8 $g/cm^3$, about 0.1 $g/cm^3$ to about 0.7 $g/cm^3$, about 0.1 $g/cm^3$ to about 0.6 $g/cm^3$, about 0.1 $g/cm^3$ to about 0.5 $g/cm^3$, about 0.1 $g/cm^3$ to about 0.4 $g/cm^3$, about 0.1 $g/cm^3$ to about 0.3 $g/cm^3$, less than 0.3 $g/cm^3$. In a preferred embodiment, tap density is greater than about 0.4 $g/cm^3$. In another preferred embodiment, tap density is greater than about 0.5 $g/cm^3$. Alternatively, tap density is less than about 0.4 g/cc.

Alternatively or in addition, the respirable dry powders and dry particles of the invention can have a water or solvent content of less than about 15% by weight of the respirable dry particle. For example, the respirable dry particles of the invention can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the invention can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

The dissolution of the respirable dry powders and respirable dry particles upon deposition of the dry powder or particles in the lungs may be rapid or sustained. The period of sustained dissolution, in one aspect, is on the time scale of minutes, for example half of the calcium cation of the calcium lactate can be released from the particle in more than about 30 minutes or more than about 45 minutes. In another aspect, the period of sustained dissolution is over a time scale of hours, for example half of the calcium ion of the calcium lactate can be released in more than about 1 hour, more than 1.5 hours, more than about 2 hours, more than about 4 hours, more than about 8 hours, or more than about 12 hours. In a further aspect, the period of sustained dissolution is over a period of one day or two days.

The respirable dry particles can be characterized by the crystalline and amorphous content of the particles. The respirable dry particles can comprise a mixture of amorphous and crystalline content, in which the monovalent metal cation salt, e.g., sodium salt and/or potassium salt, is substantially in the crystalline phase. As described herein, the respirable dry particles can further comprise an excipient, such as leucine, maltodextrin or mannitol, and/or a pharmaceutically active agent. The excipient and pharmaceutically active agent can independently be crystalline or amorphous or present in a combination of these forms. In some embodiments, the excipient is amorphous or predominately amorphous. In some embodiments, the respirable dry particles are substantially crystalline.

This provides several advantages. For example, the crystalline phase (e.g., crystalline sodium chloride) can contribute to the stability of the dry particle in the dry state and to the dispersibility characteristics, whereas the amorphous phase (e.g., amorphous active agent and/or excipient) can facilitate rapid water uptake and dissolution of the particle upon deposition in the respiratory tract. It is particularly advantageous when salts with relatively high aqueous solubilities (such as sodium chloride) that are present in the dry particles are in a crystalline state and when salts with relatively low aqueous solubilities (such as calcium citrate) are present in the dry particles in an amorphous state.

The amorphous phase can be characterized by a high glass transition temperature ($T_g$), such as a $T_g$ of at least 100° C., at least 110° C., 120° C., at least 125° C., at least 130° C., at least 135° C., at least 140° C., between 120° C. and 200° C., between 125° C. and 200° C., between 130° C. and 200° C., between 120° C. and 190° C., between 125° C. and 190° C., between 130° C. and 190° C., between 120° C. and 180° C., between 125° C. and 180° C., or between 130° C. and 180° C. Alternatively, the amorphous phase can be characterized by a high $T_g$ such as at least 80° C. or at least 90° C.

In some embodiments, the respirable dry particles contain an excipient and/or active agent rich amorphous phase and a monovalent salt (sodium salt, potassium salt) crystalline phase and the ratio of amorphous phase to crystalline phase (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain an amorphous phase and a monovalent salt crystalline phase and the ratio of amorphous phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain an amorphous phase and a monovalent salt crystalline phase and the ratio of crystalline phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5.

In addition to any of the features and properties described herein, in any combination, the respirable dry particles can have a heat of solution that is not highly exothermic. Preferably, the heat of solution is determined using the ionic liquid of a simulated lung fluid (e.g., as described in Moss, O. R. 1979. Stimulants of lung interstitial fluid. Health Phys. 36, 447-448; or in Sun, G. 2001. Oxidative interactions of synthetic lung epithelial lining fluid with metal-containing particulate matter. Am J Physiol Lung Cell Mol Physiol. 281, L807-L815) at pH 7.4 and 37° C. in an isothermal calorimeter. For example, the respirable dry particles can have a heat of solution that is less exothermic than the heat of solution of calcium chloride dihydrate, e.g., have a heat of solution that is greater than about −10 kcal/mol, greater than about −9 kcal/mol, greater than about −8 kcal/mol, greater than about −7 kcal/mol, greater than about −6 kcal/mol, greater than about −5 kcal/mol, greater than about −4 kcal/mol, greater than about −3 kcal/mol, greater than about −2 kcal/mol, greater than about −1 kcal/mol or about −10 kcal/mol to about 10 kcal/mol.

The respirable dry powders and dry particles are characterized by a high emitted dose (e.g., CEPM of at least 40%, at least 45%, at least 50%, at least 55%, at least 60%, at least 65%, at least 70%, at least 75%, at least 80%, at least 85%, at least 90%, at least 95%) from a dry powder inhaler when a total inhalation energy of less than about 2 Joules or less than about 1 Joule, or less than about 0.8 Joule, or less than about 0.5 Joule, or less than about 0.3 Joule is applied to the dry powder inhaler. The dry powder can fill the unit dose container, or the unit dose container can be at least 10% full, at least 20% full, at least 30% full, at least 40% full, at least 50% full, at least 60% full, at least 70% full, at least 80% full, or at least 90% full. The unit dose container can be a capsule (e.g., size 000, 00, 0E, 0, 1, 2, 3, and 4, with respective volumetric capacities of 1.37 ml, 950 μl, 770 μl, 680 μl, 480 μl, 360 μl, 270 μl, and 200 μl).

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa1/2/LPM, with a inhalation volume of 2 L based on both FDA guidance documents for dry powder inhalers and on the work of Tiddens et al. (Journal of Aerosol Med, 19(4), p. 456-465, 2006) who found adults averaging 2.2 L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p. 780-783, 2001) was used to predict maximum and minimum achievable PIFR through 2 dry powder inhalers of resistances 0.021 and 0.032 kPa1/2/LPM for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention.

An advantage of aspects of the invention is the production of powders that disperse well across a wide range of flow rates and are relatively flow rate independent. In certain aspects, the dry particles and powders of the invention enable the use of a simple, passive DPI for a wide patient population.

In preferred aspects, the respirable dry powder comprises respirable dry particles that characterized by:

1. VMGD at 1 bar as measured using a HELOS/RODOS system between 0.5 microns and 10 microns, preferably between 1 microns and 7 microns, between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. tap density of about 0.4 $g/cm^3$ to about 1.2 $g/cm^3$, 0.5 $g/cm^3$ to about 1.0 $g/cm^3$, preferably between about 0.6 $g/cm^3$ and about 0.9 $g/cm^3$.

In other preferred aspects, the respirable dry powder comprises respirable dry particles that are characterized by:

1. VMGD at 1 bar as measured using a HELOS/RODOS system between 0.5 microns and 10 microns, preferably between 1 microns and 7 microns, between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. MMAD between 0.5 and 6.0, between 1.0 and 5.0 or between 1.0 and 3.0.

In other preferred aspects, the respirable dry powder comprises respirable dry particles that are characterized by:

1. VMGD at 1 bar as measured using a HELOS/RODOS system between 0.5 microns and 10 microns, preferably between 1 microns and 7 microns, between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. FPF_TD<5.0 μm of at least 30%, at least 40%, at least 50% or at least 60%.

In other preferred aspects, the respirable dry powder comprises respirable dry particles that are characterized by:

1. VMGD at 1 bar as measured using a HELOS/RODOS system; less than 10 microns, between 0.5 microns and 10 microns, between 1 microns and 7 microns, preferably between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. Hausner Ratio greater than 1.5, greater than 1.8, or greater than 2.1.

In other preferred aspects, the respirable dry powder comprises respirable dry particles that are characterized by:

1. tap density of about 0.4 $g/cm^3$ to about 1.2 $g/cm^3$, 0.5 $g/cm^3$ to about 1.0 $g/cm^3$, preferably between about 0.6 $g/cm^3$ and about 0.9 $g/cm^3$.
2. FPF_TD<5.0 μm of at least 30%, at least 40%, at least 50% or at least 60%.
3. Hausner Ratio greater than 1.5, greater than 1.8, or greater than 2.1.

For each of the preferred embodiments described, the respirable dry particles described herein contain a monovalent salt; such as a sodium salt and/or a potassium salt, e.g., sodium chloride, sodium citrate, sodium lactate, sodium sulfate, potassium chloride, potassium citrate, or any combinations thereof, in an amount between about 1% and about 20%, between about 3% and about 20%, between about 20% and about 60%, or between about 60% and about 99%. The preferred embodiments may further contain:

(a) an active agent, such as a LABA (e.g., formoterol, salmeterol), a short-acting beta agonist (e.g., albuterol), a corticosteroid (e.g., fluticasone), a LAMA (e.g., tiotropium), an antibiotic (e.g., levofloxacin, tobramycin), antibodies (e.g., therapeutic antibodies), hormones (e.g. insulin), cytokines, growth factors and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof, in an amount between about 0.01% and about 10%, between about 10% and about 50%, or between about 50% and about 99.9, and further may contain, (b) an excipient, such as leucine, maltodextrin, mannitol or any combination thereof, or the like, can be present in an amount of about 80% or less or about 50% or less or about 20% or less by weight of the dry particle.

The respirable dry particles and dry powders described herein are suitable for inhalation therapies. The respirable dry particles may be fabricated with the appropriate material, surface roughness, diameter and density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration.

Because the respirable dry powders and respirable dry particles described herein contain salts, they may be hygroscopic. Accordingly it is desirable to store or maintain the respirable dry powders and respirable dry particles under conditions to prevent hydration of the powders. For example, if it is desirable to prevent hydration, the relative humidity of the storage environment should be less than 75%, less than 60%, less than 50%, less than 40%, less than 35%, less than 30%, less than 25%, less than 20%, less than 15%, less than 10%, or less than 5% humidity. In other embodiments, the storage environment should be between 20% to 40%, between 25% to 35%, about 30%, between 10% to 20%, or about 15% humidity. The respirable dry powders and respirable dry particles can be packaged (e.g., in sealed capsules, blisters, vials) under these conditions.

In preferred embodiments, the respirable dry powders or respirable dry particles of the invention possess aerosol characteristics that permit effective delivery of the respirable dry particles to the respiratory system without the use of propellants.

The dry particles of the invention can be blended with an active ingredient or co-formulated with an active ingredient to maintain the characteristic high dispersibility of the dry particles and dry powders of the invention.

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, spray freeze drying, milling (e.g., jet milling), blending, solvent extraction, solvent evaporation, phase separation, simple and complex coacervation, interfacial polymerization, suitable methods that involve the use of supercritical carbon dioxide ($CO_2$), sonocrystalliztion, nanoparticle aggregate formation and other suitable methods, including combinations thereof. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

The respirable dry particles are preferably spray dried. Suitable spray drying techniques are described, for example, by K. Masters in "Spray Drying Handbook", John Wiley & Sons, New York (1984). Generally, during spray drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by GEA Group (Niro, Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C. If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the invention, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions.

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD, or between 0.5 to about 5 micron VMGD.

The invention also relates to respirable dry powders or respirable dry particles produced by preparing a feedstock solution, emulsion or suspension and spray drying the feedstock according to the methods described herein, and to the methods described herein. The feedstock can be prepared, for example, using (a) monovalent salt, such as sodium chloride or potassium chloride, in an amount of about 1% to 100% by weight (e.g., of total solutes used for preparing the feedstock), an excipient, such as leucine, in an amount of about 0% to 99% by weight (e.g., of total solutes used for preparing the feedstock), and optionally a pharmaceutically active agent in an amount of about 0.001% to 99% by weight (e.g., of total solutes used for preparing the feedstock), and one or more suitable solvents for dissolution of the solute and formation of the feedstock.

Any suitable method can be used for mixing the solutes and solvents to prepare feedstocks (e.g., static mixing, bulk mixing). If desired, additional components that cause or facilitate the mixing can be included in the feedstock. For example, carbon dioxide produces fizzing or effervescence and thus can serve to promote physical mixing of the solute and solvents. Various salts of carbonate or bicarbonate can promote the same effect that carbon dioxide produces and, therefore, can be used in preparation of the feedstocks of the invention.

In an embodiment, the respirable dry powders or respirable dry particles of the invention can be produced through an ion exchange reaction. In certain embodiments of the invention, two saturated or sub-saturated solutions are fed into a static mixer in order to obtain a saturated or supersaturated solution post-static mixing. Preferably, the post-mixed solution is supersaturated. The post-mixed solution may be supersaturated in all components or supersaturated in one, two, or three of the components.

The two solutions may be aqueous or organic, but are preferably substantially aqueous. When the active agent is dissolved in an organic solvent, then one feed solution may be organic while the other one may be aqueous, or both feed solutions may be organic. The post-static mixing solution is then fed into the atomizing unit of a spray dryer. In a preferable embodiment, the post-static mixing solution is immediately fed into the atomizer unit. Some examples of an atomizer unit include a two-fluid nozzle, a rotary atomizer, or a pressure nozzle. Preferably, the atomizer unit is a two-fluid nozzle. In one embodiment, the two-fluid nozzle is an internally mixing nozzle, meaning that the gas impinges on the liquid feed before exiting to most outward orifice. In another embodiment, the two-fluid nozzle is an externally mixing nozzle, meaning that the gas impinges on the liquid feed after exiting the most outward orifice.

The diameter of the respirable dry particles, for example, their VMGD, can be measured using an electrical zone sensing instrument such as a Multisizer IIe, (Coulter Electronic, Luton, Beds, England), or a laser diffraction instrument such as a HELOS system (Sympatec, Princeton, N.J.) or a Mastersizer system (Malvern, Worcestershire, UK). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Aerosol Particle Sizer (APS) Spectrometer (TSI Inc., Shoreview, Minn. can be used to measure aerodynamic diameter. The APS measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor (ACI) and the multi-stage liquid impinger (MSLI) methods. The methods and instruments for measuring particle aerodynamic diameter are well known in the art.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture, high particle cohesiveness and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopeia convention, Rockville, Md., $10^{th}$ Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade Impactor, is one method of measuring the size distribution, or fine particle fraction, of airborne respirable dry particles. The ACI is an eight-stage Impactor that can separate aerosols into nine distinct fractions based on aerodynamic size. The size cutoffs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages 0 and 2 of the eight-stage ACI, as well as the final collection filter, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on the final collection filter is thus composed of respirable dry particles having an aerodynamic diameter of less than 3.4 microns. The airflow at such a calibration is approximately 60 L/min. The FPF(<5.6) has been demonstrated to correlate to the fraction of the powder that is able to reach the lungs of the patient, while the FPF(<3.4) has been demonstrated to correlate to the fraction of the powder that reaches the deep lung of a patient. These correlations provide a quantitative indicator that can be used for particle optimization.

The FPF(<5.6) has been demonstrated to correlate to the fraction of the powder that is able to make it into the lung of the patient, while the FPF(<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing and analyzing all stages, all stage filters, and the induction port of the ACI to the nominal dose. The FPF_TD(<5.0) is the ratio of the interpolated amount of powder depositing below 5.0 μm on the ACI to the nominal dose. The FPF_RD (<5.0) is the ratio of the interpolated amount of powder depositing below 5.0 μm on the ACI to either the gravimetric recovered dose or the analytical recovered dose.

Another way to approximate emitted dose is to determine how much powder leaves its container, e.g. capture or blister, upon actuation of a dry powder inhaler (DPI). This takes into account the percentage leaving the capsule, but does not take into account any powder depositing on the DPI. The emitted powder mass is the difference in the weight of the capsule with the dose before inhaler actuation and the weight of the capsule after inhaler actuation. This measurement can be called the capsule emitted powder mass (CEPM) or sometimes termed "shot-weight".

A Multi-Stage Liquid Impinger (MSLI) is another device that can be used to measure fine particle fraction. The MSLI operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The geometric particle size distribution can be measured for the respirable dry powder after being emitted from a dry powder inhaler (DPI) by use of a laser diffraction instrument such as the Malvern Spraytec. With the inhaler adapter in the close-bench configuration, an airtight seal is made to the DPI, causing the outlet aerosol to pass perpendicularly through the laser beam as an internal flow. In this way, known flow rates can be drawn through the DPI by vacuum pressure to empty the DPI. The resulting geometric particle size distribution of the aerosol is measured by the photodetectors with samples typically taken at 1000 Hz for the duration of the inhalation and the DV50, GSD, FPF<5.0 μm measured and averaged over the duration of the inhalation.

The invention also relates to a respirable dry powder or respirable dry particles produced using any of the methods described herein.

The respirable dry particles of the invention can also be characterized by the physicochemical stability of the salts or the excipients that the respirable dry particles comprise. The physicochemical stability of the constituent salts can affect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the invention include salts that are generally stable over a long period time.

If desired, the respirable dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. For example, maltodextrin may act as an amorphous phase stabilizer and inhibit the components from converting from an amorphous to crystalline state. Alternatively, a post-processing step to help the particles through the crystallization process in a controlled way (e.g., on the product filter at elevated humidity) can be employed with the resultant powder potentially being further processed to restore their dispersibility if agglomerates formed during the crystallization process, such as by passing the particles through a cyclone to break apart the agglomerates. Another possible approach is to optimize around formulation or process conditions that lead to manufacturing particles that are more crystalline and therefore more stable. Another approach is to use different excipients, or different levels of current excipients to attempt to manufacture more stable forms of the salts.

Therapeutic Use and Methods

The respirable dry powders and respirable dry particles of the present invention are for administration to the respiratory tract. Administration to the respiratory tract can be for local activity of the delivered pharmaceutically active agent or for systemic activity. For example, the respirable dry powders can be administered to the nasal cavity or upper airway to provide, for example, anti-inflammatory, anti-viral, or anti-bacterial activity to the nasal cavity or upper airway. The respirable dry powders can be administered to the deep lung to provide local activity in the lung or for absorption into the systemic circulation. Systemic delivery of certain pharmaceutically active agents via the lung is particularly advantageous for agents that undergo substantial first pass metabolism (e.g., in the liver) following oral administration.

The respirable dry powders and respirable dry particles of the present invention may also be administered to the buccal cavity. Administration to the buccal cavity can be for local activity of the delivered pharmaceutically active agent or for systemic activity. For example, the respirable dry powders can be administered to the buccal cavity to provide, for example, anti-inflammatory, anti-viral, or anti-bacterial activity to the buccal cavity.

The dry powders and dry particles of the invention can be administered to a subject in need thereof for systemic delivery of a pharmaceutically active agent, such as to treat an infectious disease or metabolic disease.

The dry powders and dry particles of the invention can be administered to a subject in need thereof for the treatment of respiratory (e.g., pulmonary) diseases, such as respiratory syncytial virus infection, idiopathic fibrosis, alpha-1 antitrypsin deficiency, asthma, airway hyperresponsiveness, seasonal allergic allergy, brochiectasis, chronic bronchitis, emphysema, chronic obstructive pulmonary disease, cystic fibrosis and the like, and for the treatment and/or prevention of acute exacerbations of these chronic diseases, such as exacerbations caused by viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Burkholderis* ssp., *Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, including pollen and cat dander, airborne particulates, and the like).

The dry powders and dry particles of the invention can be administered to a subject in need thereof for the treatment and/or prevention and/or reducing contagion of infectious diseases of the respiratory tract, such as pneumonia (including community-acquired pneumonia, nosocomial pneumonia (hospital-acquired pneumonia, HAP; health-care associated pneumonia, HCAP), ventilator-associated pneumonia (VAP)), ventilator-associated tracheobronchitis (VAT), bronchitis, croup (e.g., postintubation croup, and infectious croup), tuberculosis, influenza, common cold, and viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella*

*pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, airborne particulates, and the like).

In some aspects, the invention provides a method for treating a pulmonary diseases, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention provides a method for the treatment or prevention of acute exacerbations of a chronic pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In some aspects, the invention provides a method for the treatment or prevention of cardiovascular disease, autoimmune disorders, transplant rejections, autoimmune disorders, allergy-related asthma, infections, and cancer. For example, the invention provides a method for the treatment or prevention of postmenopausal osteoporosis, cryopyrin-associated periodic syndromes (CAPS), paroxysmal nocturnal hemoglobinuria, psoriasis, rheumatoid arthritis, psoriatic arthritis, ankylosing spondylitis, multiple sclerosis, and macular degeneration. For example, dry powders or dry particles of the invention are co-formulated or blended with therapeutic antibodies as described herein. The co-formulated or blended dry powders may then be administered to a subject in need of therapy or prevention.

In certain aspects, the invention provides a method for the treatment or prevention of cancer such as acute myeloid leukemia, B cell leukemia, non-Hodgkin's lymphoma, breast cancer (e.g. with HER2/neu overexpression), glioma, squamous cell carcinomas, colorectal carcinoma, anaplastic large cell lymphoma (ALCL), Hodgkin lymphoma, head and neck cancer, acute myelogenous leukemia (AML), melanoma, and chronic lymphocytic leukemia (CLL). Alternatively or in addition, the invention provides a method for the treatment or prevention of cancer by anti-angiogenic cancer therapy. For example, dry powders or dry particles of the invention are co-formulated or blended with therapeutic antibodies as described herein. Therapeutic antibodies can be cancer-specific antibodies, such as a humanized monoclonal antibody, e.g. gemtuzumab, alemtuzumab, trastuzumab, nimotuzumab, bevacizumab, or a chimeric monoclonal antibody, e.g. rituximab and cetuximab. The co-formulated or blended dry powders may then be administered to a subject in need of therapy or prevention.

In certain aspects, the invention provides a method for the treatment or prevention of inflammation such as rheumatoid arthritis, Crohn's disease, ulcerative Colitis, acute rejection of kidney transplants, moderate-to-severe allergic asthma. For example, dry powders or dry particles of the invention are co-formulated or blended with therapeutic antibodies as described herein. Therapeutic antibodies can be inflammation-specific antibodies, such as chimeric monoclonal antibodies, e.g. infliximab, basiliximab, humanized monoclonal antibodies, e.g. daclizumab, omalizumab, or human antibodies, e.g. adalimumab. The co-formulated or blended dry powders may then be administered to a subject in need of therapy or prevention.

In certain aspects, the invention provides a method for the treatment or prevention of RSV infections in children. For example, dry powders or dry particles of the invention are co-formulated or blended with therapeutic antibodies as described herein. Therapeutic antibodies can be RSV infection-specific antibodies, such as the humanized monoclonal antibody palivizumab which inhibits an RSV fusion (F) protein. The co-formulated or blended dry powders may then be administered to a subject in need of RSV infection therapy or prevention.

In certain aspects, the invention provides a method for the treatment or prevention of diabetes. For example, dry powders or dry particles of the invention are co-formulated or blended with insulin as described herein. The co-formulated or blended dry powders may then be administered to a subject in need of insulin therapy or prevention.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, N.C.), FlowCapss® (Hovione, Loures, Portugal), Inhalators® (Boehringer-Ingelheim, Germany), Aerolizer® (Novartis, Switzerland), high-resistance and low-resistacne RS-01 (Plastiape, Italy), and others known to those skilled in the art.

Generally, inhalation devices (e.g., DPIs) are able to deliver a maximum amount of dry powder or dry particles in a single inhalation, which is related to the capacity of the blisters, capsules (e.g. size 000, 00, 0E, 0, 1, 2, 3, and 4, with respective volumetric capacities of 1.37 ml, 950 al, 770 μl, 680 μl, 480 μl, 360 μl, 270 μl, and 200 μl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using a breath-activated DPI. When this type of device is used, the energy of the subject's inhalation both disperses the respirable dry particles and draws them into the respiratory tract.

The respirable dry particles or dry powders can be delivered by inhalation to a desired area within the respiratory tract, as desired. It is well-known that particles with an aerodynamic diameter of about 1 micron to about 3 microns, can be delivered to the deep lung. Larger aerodynamic diameters, for example, from about 3 microns to about 5 microns can be delivered to the central and upper airways.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g. above 5 um, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 microns or less), the size distribution of the inhaled powder may have an MMAD of greater than 5 μm, leading to enhanced oral cavity deposition.

Therefore, it is desirable to have a powder in which the particles are small (e.g., MMAD of 5 microns or less, e.g. between 1 to 5 microns), and are highly dispersible (e.g. 1 bar/4 bar or alternatively, 0.5 bar/4 bar of 2.0, and preferably less than 1.5). More preferably, the respirable dry powder is comprised of respirable dry particles with an MMAD between 1 to 4 microns or 1 to 3 microns, and have a 1 bar/4 bar less than 1.4, or less than 1.3, and more preferably less than 1.2.

The absolute geometric diameter of the particles measured at 1 bar using the HELOS system is not critical provided that the particle's envelope mass density is sufficient such that the MMAD is in one of the ranges listed above, wherein MMAD is VMGD times the square root of the envelope mass density (MMAD=VMGD*sqrt(envelope mass density)). If it is desired to deliver a high unit dose of pharmaceutically active agent using a fixed volume dosing container, then, particles of higher envelop density are desired. High envelope mass density allows for more mass of powder to be contained within the fixed volume dosing container. Preferable envelope mass densities are greater than 0.1 g/cc, greater than 0.25 g/cc, greater than 0.4 g/cc, greater than 0.5 g/cc, greater than 0.6 g/cc, greater than 0.7 g/cc, and greater than 0.8 g/cc.

The respirable dry powders and particles of the invention can be employed in compositions suitable for drug delivery via the respiratory system. For example, such compositions can include blends of the respirable dry particles of the invention and one or more other dry particles or powders, such as dry particles or powders that contain another active agent, or that consist of or consist essentially of one or more pharmaceutically acceptable excipients.

Respirable dry powders and dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry powders or particles deposit in the deep lung. In another embodiment of the invention, delivery is primarily to the central airways. In another embodiment, delivery is to the upper airways.

The respirable dry particles or dry powders of the invention can be delivered by inhalation at various parts of the breathing cycle (e.g., laminar flow at mid-breath). An advantage of the high dispersibility of the dry powders and dry particles of the invention is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they are released later in the inhalation.

The highly dispersible powders of the invention can provide advantages for targeting the timing of drug delivery in the breathing cycle and also location in the human lung. Because the respirable dry powders of the invention can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate which diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Elsevier, Amsterdam (1985).

Suitable dosing to provide the desired therapeutic effect can be determined by a clinician based on the severity of the condition (e.g., infection), overall well being of the subject and the subject's tolerance to respirable dry particles and dry powders and other considerations. Based on these and other considerations, a clinician can determine appropriate doses and intervals between doses. Generally, respirable dry particles and dry powders are administered once, twice or three times a day, as needed.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

Another advantage provided by the respirable dry powders and respirable dry particles described herein, is that dosing efficiency can be increased as a result of hygroscopic growth of particles inside the lungs, due to particle moisture growth. The propensity of the partially amorphous, high salt compositions of the invention to take up water at elevated humidities can also be advantageous with respect to their deposition profiles in vivo. Due to their rapid water uptake at high humidities, these powder formulations can undergo hygroscopic growth do the absorbance of water from the humid air in the respiratory tract as they transit into the lungs. This can result in an increase in their effective aerodynamic diameters during transit into the lungs, which will further facilitate their deposition in the airways.

EXEMPLIFICATION

Methods:

Geometric or Volume Diameter.

Volume median diameter (VMD) (x50), which may also be referred to as volume median geometric diameter (VMGD) and Dv(50), was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar with maximum orifice ring pressure) of the incoming compressed dry air. The pressure settings may be varied to vary the amount of energy used to disperse the powder. For example, the regulator pressure may be varied from 0.2 bar to 4.0 bar. Powder sample is dispensed from a microspatula into the RODOS funnel. The dispersed particles travel through a laser beam where the resulting diffracted light pattern produced is collected, typically using an R1 lens, by a series of detectors. The ensemble diffraction pattern is then translated into a volume-based particle size distribution using the Fraunhofer diffraction model, on the basis that smaller particles diffract light at larger angles. Using this method, geometric standard deviation (GSD) for the volume mean geometric diameter was also determined.

Fine Particle Fraction.

The aerodynamic properties of the powders dispersed from an inhaler device were assessed with a Mk-II 1 ACFM Andersen Cascade Impactor (Copley Scientific Limited, Nottingham, UK). The instrument was run in controlled environmental conditions of 18 to 25° C. and relative humidity (RH) between 25 and 35%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain. Gravimetric or analytical analysis can then be performed to determine the particle size distribution.

The impaction technique utilized allowed for the collection of eight separate powder fractions. The capsules (Capsugel, Greenwood, S.C.) were filled with approximately 20, 40 or 50 mg powder and placed in a hand-held, breath-activated dry powder inhaler (DPI) device, the high resistance RS-01 DPI (Plastiape, Osnago, Italy). The capsule was punctured and the powder was drawn through the cascade impactor operated at a flow rate of 60.0 L/min for 2.0 seconds. At this flow rate, the calibrated cut-off diameters for the eight stages are 8.6, 6.5, 4.4, 3.3, 2.0, 1.1, 0.5 and 0.3 microns. The fractions were collected by placing filters in the apparatus and determining the amount of powder that impinged on them by gravimetric and/or analytical measurements. The fine particle fraction of the total dose of powder (FPF_TD) less than or equal to an effective cut-off aerodynamic diameter was calculated by dividing the powder mass recovered from the desired stages of the impactor by the total particle mass in the capsule. Results are reported as the fine particle fraction of less than 4.4 microns (FPF<4.4 microns), as well as mass median aerodynamic diameter (MMAD) and GSD calculated from the FPF trend across stages. The fine particle fraction can alternatively be calculated relative to the recovered or emitted dose of powder by dividing the powder mass recovered from the desired stages of the impactor by the total powder mass recovered.

If desired, a two-stage collapsed ACI can also be used to measure fine particle fraction. The two-stage collapsed ACI consists of only stages 0 and 2, and the collection filter, all from the eight-stage ACI, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on a collection filter (stage F) is thus composed of respirable dry particles having an aerodynamic diameter of less than 3.4 microns. The airflow at such a calibration is approximately 60 L/min.

Tap Density.

Tap density was measured using a modified USP method requiring smaller powder quantities by following USP <616> with the substitution of a 1.5 cc microcentrifuge tube (Eppendorf AG, Hamburg, Germany) or a 0.3 cc section of a disposable serological polystyrene micropipette (Grenier Bio-One, Monroe, N.C.) with polyethylene caps (Kimble Chase, Vineland, N.J.) to cap both ends and hold the powder within the pipette section. Instruments for measuring tap density, known to those skilled in the art, include but are not limited to the Dual Platform Microprocessor Controlled Tap Density Tester (Vankel, Cary, N.C.) or a SOTAX Tap Density Tester model TD1 (Horsham, Pa.). Tap density is a standard measure of the envelope mass density. The envelope mass density of an isotropic particle is defined as the mass of the particle divided by the minimum spherical envelope volume within which it can be enclosed.

Bulk Density.

Bulk density was estimated prior to tap density measurement by dividing the weight of the powder by the volume of the powder, as estimated using the volumetric measuring device.

Emitted Geometric or Volume Diameter.

The volume median diameter (VMD) (Dv50) of the powder after it emitted from a dry powder inhaler, which may also be referred to as volume median geometric diameter (VMGD) and x50, was determined using a laser diffraction technique via the Spraytec diffractometer (Malvern, Inc., Westborough, Mass.). Powder was filled into size 3 capsules (V-Caps, Capsugel) and placed in a capsule based dry powder inhaler (RS01 Model 7 High resistance, Plastiape, Italy), or DPI, which was joined via an airtight connection to the inhaler adapter of the Spraytec. A steady airflow rate was drawn through the DPI typically at 60 L/min for a set duration, typically of 2 seconds controlled by a timer controlled solenoid (TPK2000, Copley, Scientific, UK). The outlet aerosol then passed perpendicularly through the laser beam as an internal flow. The resulting geometric particle size distribution of the aerosol was calculated from the software based on the measured scatter pattern on the photodetectors with samples typically taken at 1000 Hz for the duration of the inhalation. The Dv50, GSD, and FPF<5.0 μm measured were then averaged over the duration of the inhalation.

Fine Particle Dose.

The fine particle dose is determined using the information obtained by the ACI. The cumulative mass deposited on the filter, and stages 6, 5, 4, 3, and 2 for a single dose of powder actuated into the ACI is equal to the fine particle dose less than 4.4 microns (FPD<4.4 μm).

Capsule Emitted Powder Mass.

A measure of the emission properties of the powders was determined by using the information obtained from the ACI tests or emitted geometric diameter by Spraytec. The filled capsule weight was recorded at the beginning of the run and the final capsule weight was recorded after the completion of the run. The difference in weight represented the amount of powder emitted from the capsule (CEPM or capsule emitted powder mass). The CEPM was reported as a mass of powder or as a percent by dividing the amount of powder emitted from the capsule by the total initial particle mass in the capsule.

Example 1. Production and Characterization of Monovalent Cation Dry Powders

Several powders of the invention were produced by spray drying of homogenous particles. The dry powders produced are shown in Table 1.

TABLE 1

Composition of monovalent cation dry powders.

| Form. | Salt | % Salt load (w/w) | Excipient | % Excipient load (w/w) | Drug | % Drug load (w/w) |
|---|---|---|---|---|---|---|
| I | Sodium chloride | 65.4 | Leucine | 30 | fluticasone propionate/ salmeterol xinafoate (FP/SX) | 4/0.58 |
| II | Sodium lactate | 10 | Mannitol | 85.42 | FP/SX | 4/0.58 |
| III | Potassium chloride | 60 | Trehalose | 30 | budesonide | 10 |
| IV | Sodium chloride | 40 | Mannitol | 10 | ciprofloxacin | 50 |
| V | Potassium citrate | 5 | Maltodextrin | 45 | tobramycin | 50 |
| VI | Sodium chloride | 40.9 | Leucine | 59.1 | N/A | N/A |
| VII | Sodium chloride | 67.7 | Leucine | 30 | FP/SX | 2.0/0.29 |
| VIII | Sodium chloride | 66.7 | Leucine | 30 | FP/SX | 2.9/0.42 |
| IX | N/A | N/A | Leucine | 95.4 | FP/SX | 4/0.58 |
| X | Sodium chloride | 65.4 | Lactose | 30 | FP/SX | 4/0.58 |
| XI | N/A | N/A | Lactose | 95.4 | FP/SX | 4/0.58 |

The materials used to make the above powders and their sources are as follows. Potassium chloride, potassium citrate, sodium chloride, sodium lactate, L-leucine, lactose monohydrate, maltodextrin, mannitol, trehalose, budesonide, ciprofloxacin hydrochloride, fluticasone propionate (FP), salmeterol xinafoate (SX) and tobramycin were obtained from Sigma-Aldrich Co. (St. Louis, Mo.) or Spectrum Chemicals (Gardena, Calif.), except for sodium lactate (Chem Service, West Chester, Pa.), potassium chloride (Fisher Scientific, Pittsburgh, Pa.) and trehalose (Acros Organics, Morris Plane, N.J.). Ultrapure water was from a water purification system (Millipore Corp., Billerica, Mass.). Ethyl alcohol (200 Proof, ACS/USP Grade) was from Pharmco-Aaper (Shelbyville, Ky.).

Spray drying homogenous particles requires that the ingredients of interest be solubilized in solution or suspended in a uniform and stable suspension. Most of the materials mentioned in the material section are sufficiently water-soluble to prepare suitable spray drying solutions. However, budesonide, flucticasone propionate and salmeterol xinafoate are practically insoluble in water. As a result of these low solubilities, formulation feedstock development work was necessary to prepare solutions or suspensions that could be spray dried. Budesonide, flucticasone propionate and salmeterol xinafoate are slightly soluble in ethanol, so these were fully solubilized in 99% ethanol prior to mixing with other components dissolved in water to obtain a 2-10 g/L solids concentration in 60% ethanol solution.

For the spray drying process, the salts, excipients and other drugs were dissolved or suspended in a solvent (e.g., water). The solid concentrations (w/v) were chosen dependent on the solubility of the different components (see Table 2). The ratios used for formulations were based on the molecular weight of the anhydrous salts (see Table 3).

TABLE 2

Salt solubilities

| Salt | Water solubility at 20-30° C., 1 bar |
|---|---|
| Potassium chloride | 1 g/2.8 mL[1] |
| Potassium citrate | Monohydrate, 1 g/0.65 mL[1] |
| Sodium ascorbate | 62 g/100 mL[1] |
| Sodium bicarbonate | Soluble in 10 parts[1] |
| Sodium carbonate | Soluble in 3.5 parts[1] |
| Sodium chloride | 1 g/2.8 mL[1] |
| Sodium citrate | Dihydrate, soluble in 1.3 parts[1] |
| Sodium lactate | Commercially available as 70-80% in water[1] |
| Dibasic sodium phosphate | Soluble in ~8 parts[1] |

TABLE 2-continued

| Salt solubilities | |
|---|---|
| Salt | Water solubility at 20-30° C., 1 bar |
| Sodium propionate | 1 g/~1 mL[1] |
| Sodium sulfate | Soluble in 3.6 parts[1] |

[1]O'Neil, Maryadele J. *The Merck Index: an Encyclopedia of Chemicals, Drugs, and Biologicals.* 14th ed. Whitehouse Station, N.J.: Merck, 2006.

TABLE 3

| Weight Percent $K^+$ and $Na^+$ in Salt Molecules | | | |
|---|---|---|---|
| Salt | Molecular Formula | MW (g/mol) | Weight % of cation in molecule |
| Potassium chloride | KCl | 74.55 | 52.45 |
| Potassium citrate | $C_6H_5K_3O_7$ | 306.39 | 38.28 |
| Sodium ascorbate | $C_6H_7NaO_6$ | 198.11 | 20.23 |
| Sodium bicarbonate | $CHNaO_3$ | 84.01 | 47.71 |
| Sodium carbonate | $CNa_2O_3$ | 105.99 | 43.38 |
| Sodium chloride | NaCl | 58.44 | 39.34 |
| Sodium citrate | $C_6H_5Na_3O_7$ | 258.07 | 26.73 |
| Sodium lactate | $C_3H_5NaO_3$ | 112.06 | 20.52 |
| Dibasic sodium phosphate | $HNa_2O_4P$ | 141.96 | 28.23 |
| Sodium propionate | $C_3H_5NaO_2$ | 96.06 | 41.72 |
| Sodium sulfate | $Na_2O_4S$ | 142.04 | 32.37 |

Dry powders were prepared by spray drying on a Büchi B-290 Mini Spray Dryer (BÜCHI Labortechnik AG, Flawil, Switzerland) with powder collection from a High Performance cyclone. The system used the Büchi B-296 dehumidifier to ensure stable temperature and humidity of the air used to spray dry. Furthermore, when the relative humidity in the room exceeded 30% RH, an external LG dehumidifier (model 49007903, LG Electronics, Englewood Cliffs, N.J.) was run constantly. Atomization of the liquid feed utilized a Büchi two-fluid nozzle with a 1.5 mm diameter. Inlet temperature of the process gas can range from 100° C. to 220° C. and outlet temperature from 80° C. to 120° C. with a liquid feedstock flowrate of 3 mL/min to 10 mL/min. The two-fluid atomizing gas ranges from 25 mm to 45 mm (300 LPH to 530 LPH) and the aspirator rate from 70% to 100%. The feedstock was prepared as a batch by dissolving the specific salt in ultrapure water, then the excipient, and finally the drug component. For Formulations I-III and VII-IX where budesonide, FP and SX are practically insoluble in water, but slightly soluble in ethanol, the drug components were fully dissolved in ethanol and mixed slowly with the aqueous solution (salt and excipient previously dissolved in water) to avoid precipitation. The solution was kept agitated throughout the process until the materials were completely dissolved in the water or ethanol solvent system at room temperature.

Formulation I dry powders were produced by spray drying on the Büichi B-290 Mini Spray Dryer (BÜCHI Labortechnik AG, Flawil, Switzerland) with powder collection in a 60 mL glass vessel from a High Performance cyclone. The system used the Büichi B-296 dehumidifier and an external LG dehumidifier (model 49007903, LG Electronics, Englewood Cliffs, N.J.) was run constantly. Atomization of the liquid feed utilized a Büichi two-fluid nozzle with a 1.5 mm diameter. The two-fluid atomizing gas was set at 40 mm and the aspirator rate to 90%. Room air was used as the drying gas. Inlet temperature of the process gas was 180° C. and outlet temperature from 86° C. to 87° C. with a liquid feedstock flow rate of 8 mL/min to 9 mL/min. The solids concentration was 10 g/L in 60% ethanol.

Formulation II was produced using the same equipment and settings. Inlet temperature of the process gas was 180° C. and outlet temperature from 83° C. to 85° C. with a liquid feedstock flow rate of 9 mL/min. The solids concentration was 5 g/L in 60% ethanol.

Formulation III was produced using the same equipment and settings. Inlet temperature of the process gas was 180° C. and outlet temperature from 92° C. to 94° C. with a liquid feedstock flow rate of 6 mL/min to 7 mL/min. The solids concentration was 5 g/L in 60% ethanol.

Formulation IV was produced using the same equipment and settings. Inlet temperature of the process gas was 180° C. and outlet temperature from 75° C. to 81° C. with a liquid feedstock flow rate of 6 mL/min. The solids concentration was 10 g/L in ultrapure water.

Formulation V was produced using the same equipment and settings. Inlet temperature of the process gas was 180° C. and outlet temperature from 81° C. to 86° C. with a liquid feedstock flow rate of 6 mL/min to 7 mL/min. The solids concentration was 5 g/L in ultrapure water.

Formulation VI was produced using the same equipment and settings. Inlet temperature of the process gas was 180° C. and outlet temperature from 61° C. to 87° C. with a liquid feedstock flow rate of 6 mL/min. The solids concentration was 5 g/L in 60% ethanol.

Formulation VII was produced using the same equipment and settings. Inlet temperature of the process gas was 180° C. and outlet temperature from 88° C. to 89° C. with a liquid feedstock flow rate of 9 mL/min to 10 mL/min. The solids concentration was 10 g/L in 60% ethanol.

Formulation VIII was produced using the same equipment and settings. Inlet temperature of the process gas was 180° C. and outlet temperature from 84° C. to 85° C. with a liquid feedstock flow rate of 9 mL/min to 10 mL/min. The solids concentration was 10 g/L in 60% ethanol.

Formulation IX was produced using the same equipment and settings. Inlet temperature of the process gas was 180° C. and outlet temperature from 76° C. to 87° C. with a liquid feedstock flow rate of 9 mL/min to 10 mL/min. The solids concentration was 5 g/L in 60% ethanol.

Formulation X was produced using the same equipment and settings. Inlet temperature of the process gas was 180° C. and outlet temperature from 86° C. to 87° C. with a liquid feedstock flow rate of 9 mL/min to 10 mL/min. The solids concentration was 5 g/L in 60% ethanol.

Formulation XI was produced using the same equipment and settings. Inlet temperature of the process gas was 180° C. and outlet temperature from 87° C. to 88° C. with a liquid feedstock flow rate of 9 mL/min to 10 mL/min. The solids concentration was 5 g/L in 60% ethanol.

Formulations I, II and VII-XI comprise FP, SX and excipients. The drug loading for FP ranged from 2.0 to 4.0 wt %, while that of SX ranged from 0.29 to 0.58 wt %. The higher drug loads are comparable to the amount of drug contained within a single dosage unit of a commercial formulation of FP and SX. The lower drug loads take into account deposition efficiency of the commercial formulation, as well as anticipated aerosol properties of the formulations produced here, to target a nominal drug mass that results in the desired drug dose.

The spray drying process yield was obtained by calculating the ratio of the weight of dry powder collected after the spray drying process was completed divided by the weight of the starting solid components placed into the spray drying liquid feed.

The FPF_TD (<5.6 microns) and FPF_TD (<3.4 microns) were measured by characterizing the powders with a two stage ACI using stages 0, 2 and F. Powder formulations were filled into size 3 HPMC capsules by hand with the fill weight measured gravimetrically using an analytical balance. Fill weights of 20 mg were filled for Formulations I-III and VI-XI, 40 mg for Formulation VII and 50 mg for Formulations IV and V. An RS-01 DPI was used to disperse the powder into the cascade impactor. One capsule was used for each measurement, with two actuations of 2 L of air at 60 LPM drawn through the dry powder inhaler (DPI). The flow rate and inhaled volume were set using a timer controlled solenoid valve with flow control valve. Three replicate ACI measurements were performed for each formulation. The impactor stage plates were inverted and pre-weighed 81 mm glass fiber filters were placed on them. After the inhalation maneuver, the impactor was disassembled and the glass fiber filters were weighed. Powder that is collected on stage two is composed of respirable dry particles that have an aerodynamic diameter of less than 5.6 microns and greater than 3.4 microns. The fraction of powder passing stage two and depositing on a collection filter on stage F is thus composed of respirable dry particles having an aerodynamic diameter of less than 3.4 microns. The results of the size characterization of the powders are shown in Table 4 below.

TABLE 4

Size characteristics of monovalent cation dry powders.

| Formulation | Spray Drying Yield (%) | FPF_TD <3.4 µm (%) | FPF_TD <5.6 µm (%) |
|---|---|---|---|
| I NaCl:Leu:FP/SX | 52.1% | 59.1% | 72.3% |
| II NaLac:Mann:FP/SX | 44.7% | 2.6% | 12.5% |
| III KCl:Tre:Budes | 44.9% | 42.2% | 48.7% |
| IV NaCl:Mann:Cipro | 81.4% | 27.1% | 48.3% |
| V KCit:Malt:Tobra | 69.2% | 35.9% | 51.8% |
| VI NaCl:Leu | 40.0% | 66.9% | 82.3% |
| VII NaCl:Leu:FP/SX | 54.7% | 59.1% | 76.4% |
| VIII NaCl:Leu:FP/SX | 58.7% | 53.1% | 74.9% |
| IX Leu:FP/SX | 43.5% | 26.1% | 40.0% |
| X NaCl:Lact:FP/SX | 50.0% | 24.6% | 44.9% |
| XI Lact:FP/SX | 44.7% | 46.0% | 70.2% |

The powders produced were further characterized with regard to density and dispersibility ratio.

Bulk and tapped densities were determined using a SOTAX Tap Density Tester model TD1 (Horsham, Pa.). For any given run, a sample was introduced to a tared 0.3 cc section of a disposable serological polystyrene micropipette (Grenier Bio-One, Monroe, N.C.) using a funnel made with weighing paper (VWR International, West Chester, Pa.) and the pipette section was plugged with polyethylene caps (Kimble Chase, Vineland, N.J.) to hold the powder. The powder mass and initial volume ($V_0$) were recorded and the pipette was attached to the anvil and run according to the USP I method. For the first pass, the pipette was tapped using Tap Count 1 (500 taps) and the resulting volume $V_a$ was recorded. For the second pass, Tap Count 2 was used (750 taps) resulting in the new volume $V_{b1}$. If $V_{b1}$>98% of $V_a$, the test was complete, otherwise Tap Count 3 was used (1250 taps) iteratively until $V_{bn}$>98% of $V_{bn-1}$. Bulk density was estimated prior to tap density measurement by dividing the weight of the powder by the volume of the powder, as estimated using the volumetric measuring device. Calculations were made to determine the powder bulk density ($d_B$), tap density ($d_T$), and Hausner Ratio (H), which is the tap density divided by the bulk density.

Volume median diameter was determined using a HELOS laser diffractometer and a RODOS dry powder disperser (Sympatec, Inc., Princeton, N.J.). A microspatula of material (approximately 5 milligrams) was introduced into the RODOS funnel, where a shear force is applied to a sample of particles as controlled by the regulator pressure of the incoming compressed dry air. The pressure settings were varied to use different amounts of energy to disperse the powder. The regulator pressure was set at 0.2 bar, 0.5 bar, 1.0 bar, 2.0 bar and 4.0 bar, with maximum orifice ring pressure at each pressure. The dispersed particles traveled through a laser beam where the resulting diffracted light pattern produced is collected, using an R1 or R3 lens, by a series of detectors. The ensemble diffraction pattern is then translated into a volume-based particle size distribution using the Fraunhofer diffraction model, on the basis that smaller particles diffract light at larger angles. 1 bar/4 bar, 0.5 bar/4 bar, 0.2 bar/4 bar ratios were obtained by dividing average volume median diameter values obtained at each of 0.2 bar, 0.5 bar and 1.0 bar by the volume median diameter value obtained at 4.0 bar.

Results for the density tests for the formulations are shown in Table 5. The tap densities for Formulations I-X were relatively high (e.g., >0.4 g/cc). The bulk densities were such that the Hausner ratio was also rather high for all formulations, particularly Formulations II and IX. All of the powders tested possessed Hausner Ratios that have been described in the art as being characteristic of powders with extremely poor flow properties (See, e.g., USP <1174>). USP <1174> notes that dry powders with a Hausner ratio greater than 1.35 are poor flowing powders. Flow properties and dispersibility are both negatively affected by particle agglomeration or aggregation. It is therefore unexpected that powders with Hausner Ratios of 1.9 to 3.3 would be highly dispersible and possess good aerosolization properties

TABLE 5

Characteristics of monovalent cation dry powders.

| Formulation | Density: Bulk Density (g/cc) | Density: Tap Density (g/cc) | Hausner Ratio | HELOS/RODOS 1/4 bar | HELOS/RODOS 0.5/4 bar | HELOS/RODOS 0.2/4 bar | VMGD at 1 bar (µm) |
|---|---|---|---|---|---|---|---|
| I NaCl:Leu:FP/SX | 0.23 ± 0.01 | 0.48 ± 0.11 | 2.09 | 1.19 | 1.36 | 1.42 | 1.58 |
| II NaLac:Mann:FP/SX | 0.12 ± 0.02 | 0.39 ± 0.11 | 3.25 | 1.10 | 1.62 | 2.12 | 11.00 |
| III KCl:Tre:Budes | 0.29 ± 0.03 | 0.59 ± 0.00 | 2.03 | 1.18 | 1.39 | 1.83 | 1.27 |

TABLE 5-continued

| Characteristics of monovalent cation dry powders. | | | | | | | |
|---|---|---|---|---|---|---|---|
| | Density | | | | | | |
| | Bulk Density | Tap Density | Hausner | HELOS/RODOS | | | VMGD at 1 bar |
| Formulation | (g/cc) | (g/cc) | Ratio | 1/4 bar | 0.5/4 bar | 0.2/4 bar | (μm) |
| IV NaCl:Mann:Cipro | 0.32 ± 0.13 | 0.60 ± 0.02 | 1.88 | 0.92 | 1.00 | 1.21 | 2.00 |
| V KCit:Malt:Tobra | 0.29 ± 0.01 | 0.56 ± 0.00 | 1.93 | 1.10 | 1.16 | 1.40 | 1.55 |
| VI NaCl:Leu | 0.21 ± 0.11 | 0.41 ± 0.02 | 1.94 | 1.09 | 1.11 | 1.26 | 1.89 |
| VII NaCl:Leu:FP/SX | 0.24 ± 0.01 | 0.49 ± 0.00 | 2.04 | 1.11 | 1.16 | 1.25 | 1.76 |
| VIII NaCl:Leu:FP/SX | 0.24 ± 0.03 | 0.47 ± 0.03 | 1.96 | 1.13 | 1.30 | 1.41 | 1.56 |
| IX Leu:FP/SX | 0.22 ± 0.02 | 0.45 ± 0.02 | 2.07 | 1.25 | 1.40 | 2.46 | 1.88 |
| X NaCl:Lact:FP/S | 0.37 ± 0.01 | 0.76 ± 0.08 | 2.05 | 1.07 | 1.32 | 1.93 | 1.44 |
| XI Lact:FP/SX | 0.10 ± 0.00 | 0.19 ± 0.00 | 1.86 | 1.05 | 1.17 | 1.36 | 1.89 |

Table 5 further shows that Formulations I-XI have a HELOS/RODOS dispersibility ratio at 1/4 bar between 0.92 and 1.25, at 0.5/4 bar between 1.00 and 1.62, and at 0.2/4 bar between 1.21 and 2.46. Values that are close to 1.0, as these values are, are considered indicative of powders that are highly dispersible. In particular, Formulation I, IV, V-VIII and XI displayed highly dispersible behavior, as all had dispersive pressure ratios less than about 1.4

Table 5 also shows the VMGD at 1 bar for Formulations I through XI. The VMGD for all the formulations except for Formulation II is between about 1.2 microns and about 2.0 microns.

Example 2. Dispersibility of Monovalent Cation Powders

This example demonstrates the dispersibility of dry powder formulations when delivered from a dry powder inhaler over a range of inhalation flow rate and volumes.

The dispersibility of various powder formulations was investigated by measuring the geometric particle size distribution and the percentage of powder emitted from capsules when inhaling on a dry powder inhaler with flow rates representative of patient use. The particle size distribution and weight change of the filled capsules were measured for multiple powder formulations as a function of flow rate and inhaled volume in a passive dry powder inhaler.

Powder formulations were filled into size 3 HPMC capsules (Capsugel V-Caps) by hand with the fill weight measured gravimetrically using an analytical balance (Mettler Toledo XS205). Fill weights of 20 mg were filled for Formulations I and III. A capsule-based passive dry powder inhaler (RS-01 Model 7, High Resistance, Plastiape S.p.A.) was used which had specific resistance of 0.036 $kPa^{1/2}LPM^{-1}$. Flow rate and inhaled volume were set using a timer controlled solenoid valve and flow control valve with an inline mass flow meter (TSI model 3063). Capsules were placed in the dry powder inhaler, punctured and the inhaler sealed inside a cylinder, exposing the air jet exiting from the DPI to the laser diffraction particle sizer (Spraytec, Malvern) in its open bench configuration. The steady air flow rate through the system was initiated using the solenoid valve and the particle size distribution was measured via the Spraytec at 1 kHz for the duration of the single inhalation maneuver with a minimum of 2 seconds. Particle size distribution parameters calculated included the volume median diameter (Dv50) and the geometric standard deviation (GSD). At the completion of the inhalation duration, the dry powder inhaler was opened, the capsule removed and re-weighed to calculate the mass of powder that had been emitted from the capsule during the inhalation duration. Two inhalation conditions were used for each powder including 60 LPM and 2 L for the high inhalation energy condition and 30 LPM and 1 L for the low inhalation energy condition. At each inhalation condition, 5 replicate capsules were measured and the results of Dv50, GSD and capsule emitted powder mass (CEPM) were averaged.

In order to relate the dispersion of powder at different flow rates, volumes, and from inhalers of different resistances, the energy required to perform the inhalation maneuver was calculated. Inhalation energy was calculated as $E=R^2Q^2V$ where E is the inhalation energy in Joules, R is the inhaler resistance in $kPa^{1/2}$/LPM, Q is the steady flow rate in L/min and V is the inhaled air volume in L. In the example described here, the inhalation energy for the case of 60 LPM and 2 L was 9.2 Joules, while for the other case of 30 LPM and 1 L, the inhalation energy was 1.2 Joules.

Table 6 shows the dose emitted from a capsule (CEPM), and the particle size distribution parameters of the powder emitted (Dv50 and GSD) for Formulations I and III at a capsule fill weight of 20 mg using the high resistance RS-01 dry powder inhaler. For each powder, a 2 L inhalation was used at the high flow rate condition of 60 LPM and a 1 L inhalation for the 30 LPM condition. For Formulation I, the CEPM decreased modestly from 62% to 44% while the volume median diameter increased only slightly from 1.60 to 1.77 μm with a drop of inhalation energy from 9.2 to 1.2 Joules. For Formulation III, while the CEPM did decrease from 90 to 55%, more than 50% of the filled powder weight was emptied from the capsule at the low energy condition. The Dv50 of the emitted powder was less than 5 micrometers for both inhalation conditions.

TABLE 6

| Aerosol properties of monovalent powders. | | | |
|---|---|---|---|
| | | Flow Rate: (LPM) | |
| | | 60 | 30 |
| Formulation I | Dv(50) (μm): | 1.60 ± 0.06 | 1.77 ± 0.20 |
| NaCl:Leu: | GSD (μm): | 2.94 ± 0.46 | 4.27 ± 0.53 |
| FP/SX | CEPM (%): | 62% | 44% |
| Formulation III | Dv(50) (μm): | 1.63 ± 0.05 | 3.43 ± 0.74 |
| KCl:Tre: | GSD (μm): | 4.87 ± 0.83 | 7.09 ± 1.38 |
| Budes | CEPM (%): | 90% | 55% |

Table 7 shows the dose emitted from a capsule (CEPM) and the particle size distribution parameters of the powder emitted Dv(50) for Formulations VI through XI at the indicated capsule fill weight using the high resistance RS-01 dry powder inhaler across several flow rates. In this example, the inhaler resistance was 0.036 $kPa^{1/2}$/LPM and the inhalation energy for 60 LPM and 2 L was 9.2 Joules, for 30 LPM and 1 L was 1.2 Joules, for 20 LPM and 1 L was 0.52 Joules and for 15 LPM and 1 L was 0.29 Joules.

TABLE 7

| Aerosol properties of monovalent cation-based dry powder formulations of FP/SX. | | | | | |
|---|---|---|---|---|---|
| | | Flow Rate: (LPM) | | | |
| | | 60 | 30 | 20 | 15 |
| Formulation VI NaCl:Leu | Dv(50) (μm): | 2.4 | N/A | N/A | N/A |
| | CEPM | N/A | N/A | N/A | N/A |
| Formulation VII-1 NaCl:Leu:FP/SX (40 mg capsule fill) | Dv(50) (μm): | 1.37 ± 0.15 | 2.29 ± 0.06 | 3.53 ± 0.18 | 5.43 ± 0.42 |
| | CEPM (%): | 99.1 ± 0.1 | 69.5 ± 26.8 | 54.9 ± 26.9 | 36.1 ± 16.5 |
| Formulation VII-2 NaCl:Leu:FP/SX | Dv(50) (μm): | N/A | N/A | N/A | 5.33 ± 0.13 |
| | CEPM (%): | N/A | N/A | N/A | 90.7 ± 2.8 |
| Formulation VIII NaCl:Leu:FP/SX | Dv(50) (μm): | 1.62 ± 0.17 | 2.48 ± 0.67 | 3.65 ± 0.08 | 5.42 ± 0.16 |
| | CEPM (%): | 97.9 ± 0.4 | 94.1 ± 03.3 | 87.1 ± 16.1 | 92.5 ± 4.4 |
| Formulation IX Leu:FP/SX | Dv(50) (μm): | 2.79 ± 0.25 | 3.81 ± 0.12 | 6.24 ± 0.16 | 8.23 ± 0.51 |
| | CEPM (%): | 99.1 ± 0.1 | 98.2 ± 0.3 | 97.1 ± 0.9 | 80.7 ± 11.4 |
| Formulation X NaCl:Lact:FP/SX | Dv(50) (μm): | 1.96 ± 0.22 | 31.11 ± 6.96 | 87.03 ± 22.43 | 96.81 ± 11.81 |
| | CEPM (%): | 83.5 ± 14.7 | 40.6 ± 22.3 | 44.4 ± 19.9 | 43.5 ± 18.4 |
| Formulation XI Lact:FP/SX | Dv(50) (μm): | 2.47 ± 0.16 | 7.95 ± 0.88 | 39.61 ± 11.08 | 61.16 ± 4.71 |
| | CEPM (%): | 91.9 ± 2.8 | 49.9 ± 19.6 | 47.8 ± 21.8 | 32.5 ± 17.5 |

All powder formulations at 60 LPM and 2 L were well dispersed from the dry powder inhaler with all listed formulations having greater than 80% of the filled powder mass emptying from the capsules and median volumetric diameters of less than 5 micrometers. At the 30 LPM and 1 L condition corresponding to 1.2 Joules, formulations VIII and IX maintained a CEPM greater than 80% and volume median diameter of less than 5 micrometers, with only modest increases in diameter measured for either formulation. At the lowest flow rate condition of 15 LPM and 1 L corresponding to 0.3 Joules of inhalation energy, Formulations VII-2, VIII, and IX all showed greater than 80% CEPM and volume median diameters below 10 micrometers which is very good dispersibility at such a low applied energy condition.

Example 3. Aerodynamic Particle Size of Monovalent Cation Powders

This example demonstrates that the aerodynamic size distribution of dry powder formulations comprised in part of monovalent cationic salts, when delivered from a dry powder inhaler, is in a range appropriate for deposition in the respiratory tract.

The aerodynamic particle size distributions of five powder formulations were measured by characterizing the powders with an eight stage ACI. Powder formulations were filled into size 3 HPMC capsules (V-Caps, Capsugel) by hand with the fill weight measured gravimetrically using an analytical balance (Mettler Toledo XS205). Fill weights of 20 mg were filled for Formulations I, II, and III, and a fill weights of 50 mg were filled for Formulations IV and V. A reloadable, capsule-based passive dry powder inhaler (RS-01 Model 7, High Resistance, Plastiape, Osnago, Italy) was used to disperse the powder into the cascade impactor. One capsule was used for each measurement, with two actuations of 2 L of air at 60 LPM drawn through the dry powder inhaler (DPI). The flow rate and inhaled volume were set using a timer controlled solenoid valve with flow control valve (TPK2000, Copley Scientific). Three replicate ACI measurements were performed for each formulation. The impactor stage plates were inverted and pre-weighed 81 mm glass fiber filters (1820-6537, Whatman) were placed on them. After the inhalation maneuver, the impactor was disassembled and the glass fiber filters were weighed to determine the mass of powder deposited on each stage and on the final filter. The size distribution of the emitted powder was averaged across the replicates and the average mass of powder delivered to each of the stages (−1, −0, 1, 2, 3, 4, 5, 6, and F) are shown for each formulation in FIGS. 1A to 1E with error bars giving standard deviation of the 3 replicates. The mass median aerodynamic diameter (MMAD), geometric standard deviation (GSD), and fine particle dose (FPD<4.4 μm) of the emitted powder were calculated and averaged across the replicates and are tabulated in Table 8.

TABLE 8

Aerodynamic particle size of monovalent cation dry powder formulations.

| | aPSD (ACI-8) | | |
|---|---|---|---|
| Formulation | MMAD (μm) | GSD (μm) | FPD <4.4 μm (mg) |
| I NaCl:Leu:FP/SX | 3.01 ± 0.16 | 1.81 ± 0.04 | 11.2 ± 0.8 |
| II NaLac:Mann:FP/SX | 8.56 ± 0.40 | 1.62 ± 0.06 | 0.73 ± 0.04 |
| III KCl:Tre:Budes | 2.18 ± 0.10 | 1.71 ± 0.03 | 8.6 + 0.2 |
| IV NaCl:Mann:Cipro | 3.88 ± 0.10 | 1.75 ± 0.02 | 15.4 ± 0.7 |
| V KCit:Malt:Tobra | 2.91 ± 0.11 | 1.83 ± 0.00 | 21.1 + 1.4 |

All five formulations were found to have repeatable size distributions as illustrated by the low standard deviations for all the stages and calculated values. All five formulations had respirable size distributions with Formulations I, III, IV and V having MMADs less than 5 micrometers and Formulation II having an MMAD less than 10 micrometers.

With a maximum GSD of 1.83 for the five formulations, the polydispersity of the size distributions was relatively small compared to typical dry powder formulations for inhalation. The fine particle dose shown in Table 8 for the five powder formulations demonstrated that a significant mass of the powder dose was contained in small diameter particles that would be expected to deposit in the lung.

Example 4. Production and Optimization of Monovalent Cation Dry Powders

Several monovalent cation powders comprised of sodium sulfate and mannitol or maltodextrin were produced by spray drying of homogeneous particles. The powders produced are shown below in Table 9.

TABLE 9

Composition of monovalent cation dry powders.

| Formulation | Salt | % Salt load (w/w) | Excipient | % Excipient load (w/w) |
|---|---|---|---|---|
| XII | Sodium sulfate | 90 | Mannitol | 10 |
| XIII | Sodium sulfate | 50 | Mannitol | 50 |
| XIV | Sodium sulfate | 10 | Mannitol | 90 |
| XV | Sodium sulfate | 90 | Maltodextrin | 10 |
| XVI | Sodium sulfate | 50 | Maltodextrin | 50 |

TABLE 9-continued

Composition of monovalent cation dry powders.

| Formulation | Salt | % Salt load (w/w) | Excipient | % Excipient load (w/w) |
|---|---|---|---|---|
| XVII | Sodium sulfate | 10 | Maltodextrin | 90 |

The materials to make the above powders and their sources are as follows: sodium sulfate, mannitol and maltodextrin were purchased from Spectrum Chemicals (Gardena, Calif.). Ultrapure water was from a water purification system (Millipore Corp., Billerica, Mass.).

Formulation XII-XVII dry powders were prepared by spray drying on a Büchi B-290 Mini Spray Dryer (BÜCHI Labortechnik AG, Flawil, Switzerland) with powder collection from a High Performance cyclone. The system used the Büchi B-296 dehumidifier to ensure stable temperature and humidity of the air used to spray dry. Atomization of the liquid feed utilized a Büchi two-fluid nozzle with a 1.5 mm diameter. Inlet temperature of the process gas was 100° C. and outlet temperature ranged from 51° C. to 58° C. with a liquid feedstock flowrate of 2.6 mL/min. The two-fluid atomizing gas was set to 40 mm (473 LPH) and the aspirator rate to 80% (33 $m^3$/h). Room air was used as the drying gas. The feedstock was prepared as a batch by dissolving the specific salt in ultrapure water, then the excipient, and finally the drug component. The solution was kept agitated throughout the process until the materials were completely dissolved in the water solution at room temperature. The solids concentration was 10 g/L in 60% ultrapure water.

As shown in Table 10, all the powders had acceptable yields (dry powder output collected divided by the total solids added to the solution) from the spray drying process. The powders produced were then characterized with regard to size (FPF_TD<3.4 μm and <5.6 μm) using a two-stage ACI as described in Example 1. The large percentage of particles with a FPF_TD less than 5.6 μm and less than 3.4 μm indicated that the powder particles were respirable and of the appropriate size for deposition in the lung.

TABLE 10

Size characteristics of monovalent cation dry powders.

| Formulation | Spray Drying Yield (%) | FPF_TD <3.4 μm (%) | FPF_TD <5.6 μm (%) |
|---|---|---|---|
| XII | 81 | 27 | 49 |
| XIII | 79 | 26 | 49 |
| XIV | 77 | 32 | 54 |
| XV | 83 | 39 | 59 |
| XVI | 82 | 33 | 51 |
| XVII | 75 | 30 | 48 |

Bulk and tapped densities of the powders were determined using a TD1 as described in Example 1. Results for the density tests for formulations XII-XVII are shown in Table 11.

TABLE 11

| Characterization of monovalent cation dry powders. | | | | | | | |
|---|---|---|---|---|---|---|---|
| | Density | | | | | | VMGD |
| | Bulk Density | Tap Density | Hausner | HELOS/RODOS | | | at 1 bar |
| Formulation | (g/cc) | (g/cc) | Ratio | 1/4 bar | 0.5/4 bar | 0.2/4 bar | (μm) |
| XII | N/A | N/A | N/A | 1.18 | 0.68 | 0.94 | 5.34 |
| XIII | 0.42 ± 0.03 | 0.88 ± 0.00 | 2.11 | 1.04 | 1.12 | 1.31 | 1.80 |
| XIV | 0.38 ± 0.03 | 0.83 ± 0.05 | 2.19 | 1.04 | 1.06 | 1.17 | 1.97 |
| XV | 0.34 ± 0.06 | 0.79 ± 0.28 | 2.31 | 1.20 | 1.07 | 1.13 | 2.34 |
| XVI | 0.41 ± 0.02 | 0.88 ± 0.01 | 2.15 | 0.97 | 1.01 | 1.05 | 1.76 |
| XVII | 0.29 ± 0.03 | 0.57 ± 0.06 | 1.93 | 1.01 | 0.98 | 1.20 | 2.12 |

The tap densities of Formulations XIII-XVII were high (e.g., >than 0.4 g/cc) and their Hausner ratios were well above 1.35, a ratio typically indicative of powders with poor flowability and dispersibility. However, measurement of the dispersibility properties of the powders indicated that the formulations were surprisingly dispersible, in spite of having high Hausner ratios.

Table 11 also shows the VMGD for Formulations XII through XVII at 1 bar. The VMGD at 1 bar for Formulations XIII through XVII is between about 1.7 microns to about 2.4 microns.

The dispersibility of the dry powder formulations was assessed by measuring geometric particle size distribution Dv(50) and percentage of powder emitted from capsules (CEPM) at different flow rates representative of patient use. The Dv(50) and CEPM of Formulations XII-XVII were measured as described in Example 2, and the results are shown in Table 12.

TABLE 12

| Aerosol properties of monovalent cation dry powders. | | | | | |
|---|---|---|---|---|---|
| Formu-lation | Flow Rate: (LPM) | 60 | 30 | 20 | 15 |
| XII | Dv(50) (μm): | 2.29 ± 0.02 | 2.33 ± 0.03 | 2.58 ± 0.08 | 3.10 ± 0.10 |
| | CEPM (%): | 91.2 ± 1.7 | 73.2 ± 12.5 | 47.2 ± 21.0 | 39.5 ± 15.6 |
| XIII | Dv(50) (μm): | 2.19 ± 0.05 | 2.34 ± 0.03 | 2.70 ± 0.05 | 3.35 ± 0.04 |
| | CEPM (%): | 98.4 ± 0.8 | 97.2 ± 0.5 | 93.7 ± 2.6 | 92.8 ± 4.0 |
| XIV | Dv(50) (μm): | 2.16 ± 0.07 | 2.30 ± 0.02 | 2.70 ± 0.05 | 3.26 ± 0.09 |
| | CEPM (%): | 94.6 ± 0.8 | 88.8 ± 2.2 | 78.2 ± 10.9 | 78.8 ± 4.3 |
| XV | Dv(50) (μm): | 1.98 ± 0.01 | 2.03 ± 0.02 | 2.17 ± 0.04 | 2.70 ± 0.11 |
| | CEPM (%): | 92.9 ± 2.0 | 76.5 ± 5.9 | 71.0 ± 9.9 | 54.5 ± 24.8 |
| XVI | Dv(50) (μm): | 1.88 ± 0.02 | 1.93 ± 0.01 | 2.34 ± 0.06 | 3.10 ± 0.17 |
| | CEPM (%): | 85.9 ± 2.9 | 64.3 ± 2.9 | 53.4 ± 13.5 | 64.0 ± 4.4 |

TABLE 12-continued

| Aerosol properties of monovalent cation dry powders. | | | | | |
|---|---|---|---|---|---|
| Formu-lation | Flow Rate: (LPM) | 60 | 30 | 20 | 15 |
| XVII | Dv(50) (μm): | 2.39 ± 0.03 | 2.58 ± 0.08 | 3.37 ± 0.15 | 5.16 ± 1.49 |
| | CEPM (%): | 90.2 ± 3.3 | 36.5 ± 13.0 | 31.7 ± 21.8 | 30.1 ± 15.6 |

All powder formulations at 60 LPM and 2 L were well dispersed from the dry powder inhaler with all listed formulations having greater than 80% of the filled powder mass emptying from the capsules and median volumetric diameters of less than 5 micrometers. At the 30 LPM and 1 L condition corresponding to 1.2 Joules, all formulations still had volume median diameters of less than 5 micrometers and all except formulation XVII had greater than 60% of the powder mass emitted from the capsule. At the lowest flow rate condition of 15 LPM and 1 L corresponding to 0.3 Joules of inhalation energy, all the formulations showed little agglomeration with volume median diameters of less than 5 micrometers and formulations XIII, XIV and XVI having greater than 60% of the powder mass emitted from the capsule, a very good dispersibility a such a low applied energy condition.

Example 5. Sodium Salt-Containing Dry Powders, Optionally Combined with Active Pharmaceutical Agents A. Powder Preparation.

Feedstock solutions were prepared in order to manufacture dry powders comprised of dry particles containing a sodium salt, optionally a non-salt excipient, and at least one pharmaceutical active agent. Table 13 lists the components of the feedstock formulations used in preparation of the dry powders comprised of dry particles. Weight percentages are given on a dry basis.

TABLE 13

| Feedstock compositions of sodium-salt with other pharmaceutically active agents | | | | | | |
|---|---|---|---|---|---|---|
| Formulation | Salt | % Salt load (w/w) | Excipient | % Excipient load (w/w) | Drug | % Drug load (w/w) |
| XVIII | Sodium chloride | 40.9 | Leucine | 59.1 | N/A | 0 |

TABLE 13-continued

| Feedstock compositions of sodium-salt with other pharmaceutically active agents | | | | | | |
|---|---|---|---|---|---|---|
| Formulation | Salt | % Salt load (w/w) | Excipient | % Excipient load (w/w) | Drug | % Drug load (w/w) |
| XIX | Sodium Chloride | 34.5 | Leucine | 50.0 | fluticasone propionate/ salmeterol xinafoate (FP/SX) | 13.5/2.0 |
| XX | Sodium Chloride | 65.42 | Leucine | 34.47 | Tiotropium Bromide (TioB) | 0.113 |
| XXI | Sodium Chloride | 53 | Leucine | 27 | Levofloxacin (Levo) | 20 |
| XXII | Sodium Chloride | 85.31 | Leucine | 10.0 | FP/SX/TioB | 4.0/0.58/ 0.113 |
| XXIII | Sodium Chloride | 65.42 | Leucine | 29.89 | FP/SX/TioB | 4.0/0.58/ 0.113 |
| XXIV | Sodium sulfate | 50.0 | Mannitol | 40.0 | Insulin | 10.0 |
| XXV | Sodium sulfate | 50.0 | Mannitol | 47.5 | Immunoglobulin G (IgG) | 2.5 |
| XXVI | Sodium citrate | 45.42 | Leucine | 50.0 | FP/SX | 4.0/0.58 |
| XXVII | Sodium sulfate | 45.42 | Leucine | 50.0 | FP/SX | 4.0/0.58 |
| XXVIII | Sodium sulfate | 55.0 | Mannitol | 40.0 | Insulin | 5.0 |
| XXIX | Potassium chloride | 50.0 | Mannitol | 50.0 | N/A | N/A |
| XXX | Potassium chloride | 10.0 | Mannitol | 90.0 | N/A | N/A |
| XXXI | Potassium citrate | 10.0 | Mannitol | 90.0 | N/A | N/A |
| XXXII | Sodium lactate | 10.0 | Leucine/ Maltodextrin | 50.0/ 39.9 | TioB | 0.113 |
| XXXIII | Sodium chloride | 65.4 | Leucine | 30.0 | FP/SX | 4.0/0.58 |

N/A = not applicable

The feedstock solutions were made according to the parameters in Table 14.

TABLE 14

| Formulation Conditions | | | | | |
|---|---|---|---|---|---|
| Formulation: | XVIII | XIX | XX | XXI | XXII |
| Total solids (g) | 10 | 7.5 | 3 | 5 | 10 |
| Total volume water (L) | 2 | 2.25 | 0.3 | 0.5 | 0.4 |
| Total solids concentration (g/L) | 5 | 3.3 | 10 | 10 | 10 |
| Amount of NaCl in 1 L (g) | 2.05 | 1.15 | 6.542 | 5.3 | 8.531 |
| Amount leucine in 1 L (g) | 2.96 | 1.67 | 3.447 | 2.7 | 1.0 |
| Amount FP in 1 L (g) | 0 | 0.45 | 0 | 2.0 | 0.4 |
| Amount SX in 1 L (g) | 0 | 0.07 | 0 | 0 | 0.058 |
| Amount TioB in 1 L (g) | 0 | 0 | 0.0113 | 0 | 0.0113 |
| Formulation: | XXIII | XXIV | XXV | XXVI | XXVII |
| Total solids (g) | 4 | 5 | 5 | 2 | 2 |
| Total volume water (L) | 0.4 | 0.5 | 0.5 | 1 | 1 |
| Total solids concentration (g/L) | 10 | 10 | 10 | 2 | 2 |
| Amount of NaCl in 1 L (g) | 6.542 | 0 | 0 | 0 | 0 |
| Amount of NaSulf in 1 L (g) | 0 | 5.0 | 5.0 | 0 | 4.542 |
| Amount of NaCit in 1 L (g) | 0 | 0 | 0 | 4.542 | 0 |
| Amount leucine in 1 L (g) | 2.989 | 0 | 0 | 5.0 | 5.0 |
| Amount mannitol in 1 L (g) | 0 | 5.0 | 5.0 | 0 | 0 |
| Amount FP in 1 L (g) | 0.4 | 0 | 0 | 0.4 | 0.4 |
| Amount SX in 1 L (g) | 0.058 | 0 | 0 | 0.58 | 0.58 |

TABLE 14-continued

| Formulation Conditions | | | | | |
|---|---|---|---|---|---|
| Amount TioB in 1 L (g) | 0.0113 | 0 | 0 | 0 | 0 |
| Amount Insulin in 1 L (g) | 0 | 1 | 0 | 0 | 0 |
| Amount IgG in 1 L (g) | 0 | 0 | 0.25 | 0 | 0 |
| Formulation: | XXVIII | XXIX | XXX | XXXI | XXXII |
| Total solids (g) | 10 | 3 | 3 | 3 | 3 |
| Total volume water (L) | 0.667 | 0.3 | 0.3 | 0.3 | 0.3 |
| Total solids concentration (g/L) | 15 | 10 | 10 | 10 | 10 |
| Amount of NaCl in 1 L (g) | 0 | 0 | 0 | 0 | 0 |
| Amount of NaSulf in 1 L (g) | 5.5 | 0 | 0 | 0 | 0 |
| Amount of NaLact in 1 L (g) | 0 | 0 | 0 | 0 | 1.0 |
| Amount of KCl in 1 L (g) | 0 | 5.0 | 1.0 | 0 | 0 |
| Amount of KCit in 1 L (g) | 0 | 0 | 0 | 1.0 | 0 |
| Amount leucine in 1 L (g) | 0 | 0 | 0 | 0 | 5.0 |
| Amount mannitol in 1 L (g) | 4.0 | 5.0 | 9.0 | 9.0 | 0 |
| Amount maltodextrin in 1 L (g) | 0 | 0 | 0 | 0 | 3.897 |
| Amount TioB in 1 L (g) | 0 | 0 | 0 | 0 | 0.113 |
| Amount Insulin in 1 L (g) | 0.5 | 0 | 0 | 0 | 0 |

For all formulations, the liquid feedstock was batch mixed

The formulation conditions for Formulation XXXIII were: Total solids were 3 grams (g), total volume was 0.3 liters, total solids concentration was 10 grams per liter, amount of NaCl, leucine, FP, and SX in one liter was 6.542 g, 3.0 g, 0.4 g, and 0.058 g, respectively.

Formulation XVIII through XXXIII dry powders were produced by spray drying on the Büchi B-290 Mini Spray Dryer (BÜCHI Labortechnik AG, Flawil, Switzerland) with powder collection from a High Performance cyclone in a 60 mL glass vessel. The system used the Büchi B-296 dehumidifier and an external LG dehumidifier (model 49007903, LG Electronics, Englewood Cliffs, N.J.) was run constantly, except for Formulation XXXII. Atomization of the liquid feed utilized a Büchi two-fluid nozzle with a 1.5 mm diameter except for Formulation XXXII, which used a two-fluid nozzle with a 1.4 mm diameter. The two-fluid atomizing gas was set at 40 mm (667 LPH). The aspirator rate was set to 90% (35 $m^3$/h) for Formulations XVIII, XIX and XXI; to 80% (32 $m^3$/h) for Formulations XX, XXIV, XXV, VVIIII, XXIX, XXX, XXXI and XXXIII; 70% for Formulations XXII, XXIII, XXVI, XXVII. Formulation XXXII had an aspirator rate of 100%, but nitrogen flow limited rate to approximately 31 kg/h or 26 $m^3$/h. Air was used as the drying gas and the atomization gas, except for Formulation XXXII, where nitrogen was used. Table 15 below includes details about the spray drying conditions.

Formulation XXXIII was essentially the same formulation as Formulation I. The solution preparation was the same as for Formulation I. The spray drying process conditions were the same when going from Formulation I to Formulation XXXIII except that the inlet temperature was decreased from 180° C. to 100° C., the aspirator rate was changed from 90% to 80% (35 cubic meters per hour to 32 cubic meters per hour) and the feed rate was increased from 8.6 to 10.2 mL/min, respectively.

TABLE 15

| Spray Drying Process Conditions | | | | | |
|---|---|---|---|---|---|
| | Formulation | | | | |
| Process Parameters | XVIII | XIX | XX | XXI | XXII |
| Liquid feedstock solids concentration (g/L) | 5 | 3.3 | 10 | 10 | 10 |
| Process gas inlet temperature (° C.) | 180 | 180 | 115 | 180 | 180 |
| Process gas outlet temperature (° C.) | 61-87 | 77-92 | 67-68 | 89-92 | 74-75 |
| Process gas flowrate (liter/hr, LPH) | 667 | 667 | 667 | 667 | 667 |
| Atomization gas flowrate (meters$^3$/hr) | 35 | 35 | 32 | 35 | 29 |
| Liquid feedstock flowrate (mL/min) | 6.2 | 6.2 | 2.5 | 5.9 | 10 |
| | Formulation | | | | |
| Process Parameters | XXIII | XXIV | XXV | XXVI | XXVII |
| Liquid feedstock solids concentration (g/L) | 10 | 10 | 10 | 2 | 2 |
| Process gas inlet temperature (° C.) | 180 | 100 | 100 | 180 | 180 |
| Process gas gas outlet temperature (° C.) | 71-74 | 55-57 | 57-59 | 74-78 | 77-80 |
| Process gas flowrate (liter/hr, LPH) | 667 | 667 | 667 | 667 | 667 |

TABLE 15-continued

| Spray Drying Process Conditions | | | | | |
|---|---|---|---|---|---|
| Atomization gas flowrate (meters$^3$/hr) | 29 | 32 | 32 | 29 | 29 |
| Liquid feedstock flowrate (mL/min) | 12.1 | 2.9 | 2.8 | 10.2 | 10.5 |

| | Formulation | | | | |
|---|---|---|---|---|---|
| Process Parameters | XXVIII | XXIX | XXX | XXXI | XXXII |
| Liquid feedstock solids concentration (g/L) | 15 | 10 | 10 | 10 | 10 |
| Process gas inlet temperature (° C.) | 100 | 115 | 115 | 115 | 100 |
| Process gas outlet temperature (° C.) | 54-56 | 65-66 | 64-67 | 65-66 | 65-66 |
| Process gas flowrate (liter/hr, LPH) | 667 | 667 | 667 | 667 | 667 |
| Atomization gas flowrate (meters$^3$/hr) | 32 | 32 | 32 | 32 | 32 |
| Liquid feedstock flowrate (mL/min) | 3.2 | 2.8 | 2.7 | 2.7 | 2.7 |

The spray drying process conditions for Formulation XXXIII was: Liquid feedstock solids concentration was 10 g/L, Process gas inlet temperature was 100° C., Process gas outlet temperature was 42-43° C., Process gas flowrate was 667 liters per hour, Atomization gas flowrate (meters 3/hr) was 32 cubic meters per hour, and Liquid feedstock flowrate was 10.2 mL/min.

B. Powder Characterization.

Powder physical and aerosol properties are summarized in Tables 16 to 20 below. Values with ± indicate standard deviation of the value reported. Two-stage ACI-2 results are reported in Table 16 for $FPF_{TD}$<3.4 μm and $FPF_{TD}$<5.6 μm. All formulations had a $FPF_{TD}$<3.4 μm greater than 20%, and all but Formulations XXV, XXX and XXXI had a $FPF_{TD}$<3.4 μm greater than 30%. Formulations XVIII, XIX, XX, XXI, XXIV, XXVIII, and XXXII each had a $FPF_{TD}$<3.4 μm greater than 45%. All formulations had a $FPF_{TD}$<5.6 μm greater than 40%. Formulations XVIII through XXIV, XXVII, XXVIII, XXXII, and XXXIII each had a $FPF_{TD}$<5.6 μm of greater than 60%.

TABLE 16

| Aerodynamic properties | | | | | | |
|---|---|---|---|---|---|---|
| | ACI-2 | | | | | |
| Formulation | $FPF_{TD}$ <3.4 μm % | | | $FPF_{TD}$ <5.6 μm % | | |
| XVIII | 66.90% | ± | 0.52% | 82.35% | ± | 3.70% |
| XIX | 47.49% | ± | 4.65% | 67.70% | ± | 1.20% |
| XX | 53.96% | ± | 1.44% | 73.00% | ± | 1.80% |
| XXI | 48.24% | ± | 0.49% | 68.78% | ± | 1.81% |
| XXII | 40.29% | ± | 0.28% | 65.33% | ± | 0.41% |
| XXIII | 37.80% | ± | 2.97% | 62.74% | ± | 2.47% |
| XXIV | 53.92% | ± | 2.25% | 69.47% | ± | 0.21% |
| XXV | 29.03% | ± | 0.12% | 57.84% | ± | 0.52% |
| XXVI | 39.26% | ± | 1.35% | 59.61% | ± | 0.90% |
| XXVII | 43.06% | ± | 5.09% | 65.48% | ± | 6.09% |
| XXVIII | 56.37% | ± | 1.45% | 71.90% | ± | 0.57% |
| XXIX | 33.70% | ± | 0.68% | 50.43% | ± | 4.14% |
| XXX | 22.46% | ± | 0.73% | 45.76% | ± | 1.25% |
| XXXI | 24.40% | ± | 3.68% | 41.84% | ± | 4.50% |
| XXXII | 60.19% | ± | 1.59% | 78.87% | ± | 0.66% |
| XXXIII | 38.73% | ± | 2.10% | 64.87% | ± | 1.59% |

Data for Formulations XVIII and XIX is not available for the data presented in Tables 16 to 20, except for RODOS data reported for Formulation XVIII in Table 20.

All formulations had a tapped density greater than 0.35 g/cc, and all but Formulations XXIII and XXIV had a tapped density greater than 0.40 g/cc. Formulations XX, XXI, XXII, XXV, XXVI, XXVIII, XXX, XXXI, and XXXII each had a tapped density greater than 0.50 g/cc. Formulation XXI had a tapped density of 0.80 g/cc. All formulations had a Hausner Ratio greater than or equal to 1.5. Formulations XXII, XXIII, XXIV, XXVI, XXVII, XXVIII, XXX, XXXI, and XXXIII each had a Hausner Ratios greater than 2.0. Formulation XXII had a Hausner Ratio of 3.07. Density measurements for Formulation XXIX was unavailable.

TABLE 17

| Density properties | | | | | | | |
|---|---|---|---|---|---|---|---|
| | Density | | | | | | |
| Formulation | Bulk g/cc | | | Tapped g/cc | | | Hausner Ratio |
| XX | 0.34 | ± | 0.01 | 0.52 | ± | 0.05 | 1.54 |
| XXI | 0.46 | ± | 0.1 | 0.80 | ± | 0.17 | 1.75 |
| XXII | 0.17 | ± | 0 | 0.52 | ± | 0.04 | 3.07 |
| XXIII | 0.18 | ± | 0.01 | 0.37 | ± | 0.06 | 2.09 |
| XXIV | 0.16 | ± | 0.02 | 0.37 | ± | 0.01 | 2.28 |
| XXV | 0.52 | ± | 0.01 | 0.77 | ± | 0.10 | 1.50 |
| XXVI | 0.23 | ± | 0.00 | 0.51 | ± | 0.04 | 2.21 |
| XXVII | 0.15 | ± | 0.02 | 0.42 | ± | 0.01 | 2.73 |
| XXVIII | 0.22 | ± | 0.07 | 0.53 | ± | 0.06 | 2.40 |
| XXX | 0.27 | ± | 0.02 | 0.70 | ± | 0.05 | 2.56 |
| XXXI | 0.31 | ± | 0.03 | 0.65 | ± | 0.05 | 2.09 |
| XXXII | 0.37 | ± | 0.02 | 0.67 | ± | 0.02 | 1.81 |
| XXXIII | 0.22 | ± | 0.01 | 0.49 | ± | 0.01 | 2.26 |

Table 18 shows that all formulations had geometric diameters (Dv50) of less than 3.0 um when emitted from a dry powder inhaler at a flowrate of 60 LPM. Formulations XX, XXI, XXII, XXIII, XXIV, XXIX, and XXXII had Dv50 of less than 2.0 um at 60 LPM. All formulations, except XXXI, had a Dv50 of less than 6.0 um at 15 LPM. Formulations XXI, XXII, XXV, XXVII, XXVIII, XXIX, XXX, XXXII, and XXXIII each had a Dv50 of less than 5.0 um at 15 LPM.

TABLE 18

| Geometric Diameters | | | | |
|---|---|---|---|---|
| | Dispersibility-Spraytec | | | |
| | @ 60 LPM | | @ 15 LPM | |
| Formulation | Dv50 (μm) | GSD | Dv50 (μm) | GSD |
| XX | 1.28 ± 0.08 | 5.59 ± 0.18 | 5.85 ± 0.18 | 4.04 ± 0.10 |
| XXI | 1.33 ± 0.18 | 5.15 ± 0.13 | 2.89 ± 0.06 | 2.78 ± 0.52 |
| XXII | 1.55 ± 0.07 | 5.02 ± 0.34 | 4.23 ± 0.10 | 3.20 ± 0.25 |

TABLE 18-continued

| Geometric Diameters | | | | |
|---|---|---|---|---|
| | Dispersibility-Spraytec | | | |
| | @ 60 LPM | | @ 15 LPM | |
| Formulation | Dv50 (μm) | GSD | Dv50 (μm) | GSD |
| XXIII | 1.70 ± 0.07 | 4.47 ± 0.25 | 5.09 ± 0.20 | 3.27 ± 0.11 |
| XXIV | 1.89 ± 0.15 | 5.51 ± 0.15 | 5.65 ± 0.08 | 2.97 ± 0.05 |
| XXV | 2.44 ± 0.14 | 4.87 ± 0.28 | 4.04 ± 0.55 | 3.36 ± 0.13 |
| XXVI | 2.08 ± 0.04 | 4.85 ± 0.22 | 5.38 ± 0.09 | 3.43 ± 0.08 |
| XXVII | 2.09 ± 0.15 | 4.51 ± 0.35 | 4.73 ± 0.13 | 3.16 ± 0.16 |
| XXVIII | 2.25 ± 0.12 | 5.17 ± 0.50 | 4.56 ± 0.16 | 3.00 ± 0.13 |
| XXIX | 1.72 ± 0.02 | 4.04 ± 0.29 | 3.55 ± 0.21 | 5.96 ± 0.46 |
| XXX | 2.77 ± 0.03 | 3.84 ± 0.24 | 4.32 ± 0.18 | 4.31 ± 0.11 |
| XXXI | 2.33 ± 0.05 | 4.45 ± 0.27 | 10.12 ± 0.52 | 5.53 ± 0.40 |
| XXXII | 0.99 ± 0.12 | 5.40 ± 0.17 | 2.80 ± 0.10 | 3.29 ± 0.13 |
| XXXIII | 2.52 ± 0.16 | 4.9 ± 0.4 | 4.85 ± 0.08 | 3.07 ± 0.09 |

Table 19 shows that all formulations had a capsule emitted particle mass (CEPM) of greater than 94% at 60 LPM, and all formulations except for XXV had a CEPM of greater than 96% at 60 LPM. All formulations except for XXI and XXX had a CEPM of greater than 80% at 15 LPM. Formulations XX, XXII, XXIII, XXIV, XXV, XXVII, XXVIII, XXXII, and XXXIII each had a CEPM of greater than 90% at 15 LPM.

TABLE 19

| Dispersibilty properties | | | | | | |
|---|---|---|---|---|---|---|
| | Dispersibility - CEPM | | | | | |
| Formulation | @ 60 LPM CEPM | | | @ 15 LPM CEPM | | |
| XX | 99.33% | ± | 0.40% | 96.92% | ± | 0.81% |
| XXI | 99.96% | ± | 0.00% | 79.46% | ± | 0.11% |
| XXII | 97.46% | ± | 0.14% | 95.94% | ± | 0.55% |
| XXIII | 99.47% | ± | 0.14% | 97.92% | ± | 0.41% |
| XXIV | 98.96% | ± | 0.06% | 91.28% | ± | 8.01% |
| XXV | 94.58% | ± | 0.66% | 94.12% | ± | 0.83% |
| XXVI | 97.79% | ± | 0.28% | 83.17% | ± | 9.74% |
| XXVII | 98.63% | ± | 0.61% | 95.15% | ± | 0.88% |
| XXVIII | 98.66% | ± | 0.25% | 95.23% | ± | 0.40% |
| XXIX | 96.46% | ± | 0.46% | 85.83% | ± | 5.73% |
| XXX | 96.07% | ± | 0.47% | 74.60% | ± | 11.85% |
| XXXI | 98.63% | ± | 0.19% | 62.70% | ± | 9.68% |
| XXXII | 98.21% | ± | 0.10% | 95.53% | ± | 0.62% |
| XXXIII | 100.07% | ± | 2.01% | 95.72% | ± | 0.99% |

Table 20 shows that all measured formulations except XXIX had a Dv50 of less than 3.0 μm when using the RODOS at a 1.0 bar setting; and all measured formulations except XXIV, XXVIII, XXIX, and XXX had a Dv50 of less than 2.0 μm. All measured formulations had a RODOS Ratio for 0.5 bar/4 bar of less than 1.4, and all measured formulations except for XXII had a RODOS Ratio for 0.5 bar/4 bar of less than 1.3. All measured formulations had a RODOS Ratio for 1 bar/4 bar of less than or equal to about 1.1.

TABLE 20

| Dispersibilty properties (Geometric diameter using RODOS) | | | | | | | | |
|---|---|---|---|---|---|---|---|---|
| | RODOS | | | | | | | |
| | 0.5 bar | | 1.0 bar | | 4.0 bar | | | |
| Form. | Dv50 (μm) | GSD | Dv50 (μm) | GSD | Dv50 (μm) | GSD | 0.5/4 bar | 1/4 bar |
| XVIII | 1.93 | 1.68 | 1.89 | 1.76 | 1.74 | 1.71 | 1.11 | 1.09 |
| XX | 1.66 | 2.16 | 1.46 | 2.06 | 1.36 | 1.92 | 1.22 | 1.07 |
| XXI | 1.91 | 2.13 | 1.83 | 2.24 | 1.99 | 2.19 | 0.96 | 1.08 |
| XXII | 1.87 | 1.95 | 1.48 | 1.78 | 1.37 | 1.78 | 1.36 | 1.08 |
| XXIII | 1.95 | 1.96 | 1.74 | 1.93 | 1.6 | 1.91 | 1.22 | 1.09 |
| XXIV | 2.33 | 2.28 | 2.10 | 2.19 | 1.91 | 2.12 | 1.22 | 1.10 |
| XXV | 1.90 | 2.10 | 1.64 | 1.99 | 1.68 | 2.22 | 1.13 | 0.98 |
| XXVI | 2.09 | 1.86 | 1.83 | 1.84 | 1.68 | 1.80 | 1.24 | 1.09 |
| XXVII | 2.15 | 1.84 | 1.97 | 1.83 | 1.78 | 1.76 | 1.21 | 1.11 |
| XXVIII | 2.56 | 2.35 | 2.25 | 2.30 | 2.18 | 2.26 | 1.17 | 1.03 |
| XXIX | 2.51 | 2.41 | 3.67 | 2.48 | 3.36 | 2.16 | 0.75 | 1.09 |
| XXX | 2.62 | 2.35 | 2.55 | 2.34 | 2.42 | 2.27 | 1.08 | 1.05 |
| XXXI | 1.96 | 2.24 | 1.82 | 2.18 | 1.78 | 2.20 | 1.10 | 1.02 |
| XXXII | 1.61 | 2.23 | 1.46 | 2.20 | 1.41 | 2.15 | 1.14 | 1.04 |
| XXXIII | 2.15 | 2.07 | 1.90 | 2.05 | 1.73 | 2.06 | 1.24 | 1.10 |

Figure 11:
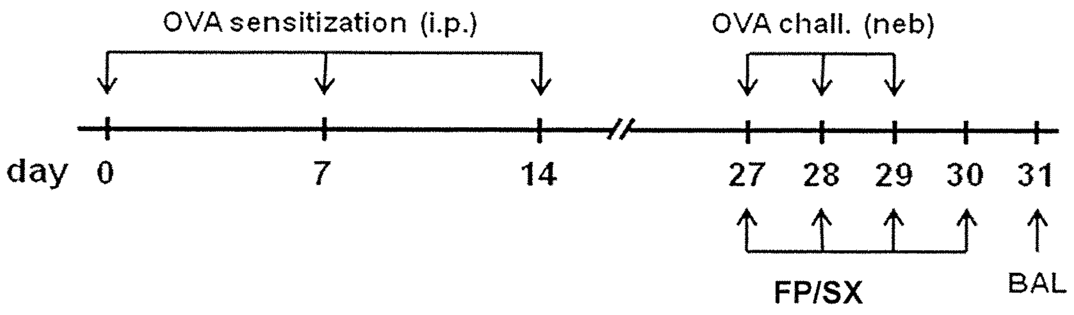
FIG. 11 is a schematic illustrating an ovalbumin (OVA) process of sensititzation, challenge, treatment and testing. The process is described in Example 6.

Example 6. Efficacy of Dry Powders in an Ovalbumin Mouse Model of Allergic Asthma Dry powder formulations comprised of leucine, sodium chloride, fluticasone propionate (FP) and salmeterol xinafoate (SX) were tested for activity in a mouse model of allergic asthma. A mouse model of allergic asthma was established using ovalbumin (OVA). In this model, mice are sensitized to OVA over a period of two weeks and subsequently challenged via aerosol with OVA, as shown in FIG. 11. This challenge induces airway inflammation and causes changes in pulmonary function. The principle change in inflammation is an increase in the number of eosinophils in the lungs. Similar changes in lung inflammation and pulmonary function are observed in humans with asthma.

Balb/c mice were sensitized and challenged to OVA on the days described above. Sensitizations were performed by intraperotineal injection of OVA plus Alum. Challenges were performed by whole body exposure to nebulized 1% OVA solution for 20 minutes. Mice were treated with the formulations listed in Table 9 1 hour before OVA challenge, on days 27 through 29 and once on day 30.

TABLE 21

| Dry powders tested in an OVA mouse model of allergic asthma. | | | |
|---|---|---|---|
| Formulation | Group | Dry Powder Composition (% w/w) | Capsules Delivered (quantity, fill weight, size) |
| Placebo-A | Control | 100% Leucine | 3, 30 mg, size 00 |
| XVIII | Control | 59.1% leucine, 40.9% sodium chloride | 1, 90 mg, size 00 |
| XIX | Active | 50.0% leucine, 34.5% sodium chloride, 13.5% FP, 2.0% SX | 1, 90 mg, size 00 |
| XIX | Active | 50.0% leucine, 34.5% sodium chloride, 13.5% FP, 2.0% SX | 3, 90 mg, size 00 |

Mice were sensitized and challenged with OVA as described and illustrated in FIG. 11, and treated once a day (QD) with a formulation comprised of leucine (50.0%), NaCl (34.5%), FP (13.5%) and SX (2.0%) (Formulation XIX; see Table 21). Treatments were made in a whole body exposure chamber using a capsule based dry powder inhaler system. Dose was varied by changing the number of capsules used for each exposure. Doses reported are the exposed dose each mouse inhaled as calculated based on the measured aerosol concentration sampled from the exposure chamber, the fraction of FP in the powder, the time of exposure, and the mouse's mass and minute volume. Mouse minute volume was calculated using a standard equation (Bide et al. (2000) "Allometric respiration/body mass data for animals to be used for estimates of inhalation toxicity to young adult humans", J. Appl. Toxicol. 20:273-290). On the final day of the study (day 31), mice were euthanized and bronchoalveolar lavages (BAL) were performed. The total number of cells per BAL was determined. In addition, the percentage and total number of macrophages, polymorphonuclear cells (neutrophils), lymphocytes, and eosinophils were determined by differential staining. Data depicted the mean±SEM of 5 mice per group and are representative of two independent experiments. Data were analyzed by one way ANOVA and Tukey's multiple comparison test, and asterisk presented in FIGS. 2A and 2B represent a p-value of $p<0.01$.

Figure 2A:
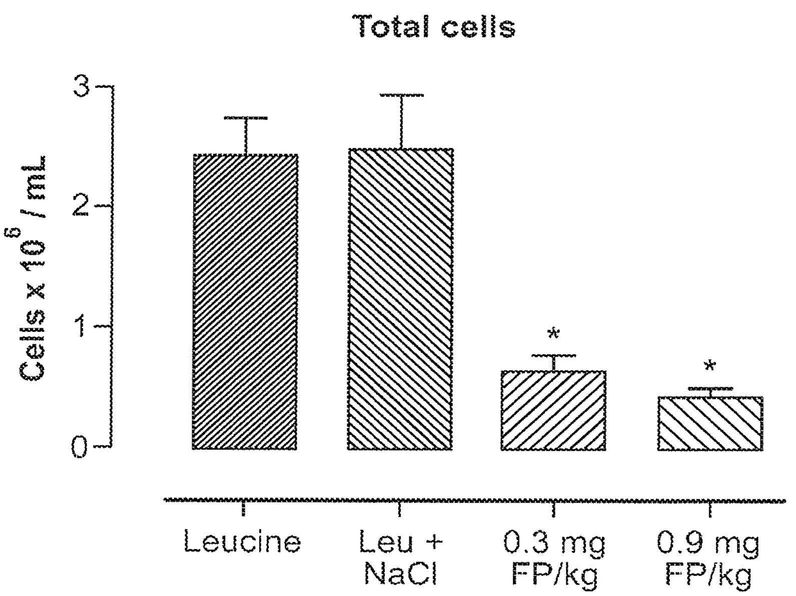
FIGS. 2A and 2B are graphs illustrating the efficacy of a monovalent cation-based dry powder formulation of FP/SX (fluticasone propionate/salmeterol xinafoate) in reducing total cell (FIG. 2B) and eosinophil cell (FIG. 2B) counts in a ovalbumin (OVA) mouse model of allergic asthma. The graphs indicate that the spray dried drug (FP/SX) remained effective in treating inflammation.
Figure 2B:
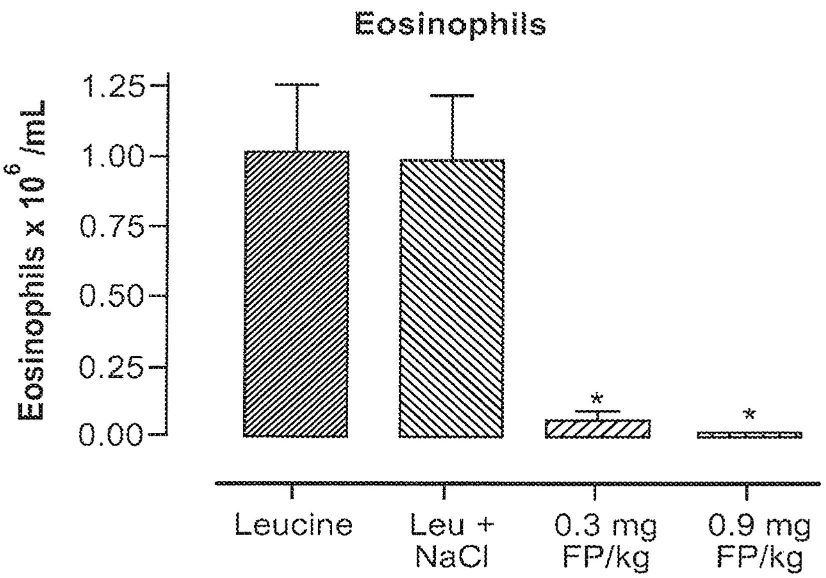

The data shown in FIGS. 2A and 2B demonstrated that mice treated with dry powder formulations comprised of FP and SX exhibited a significant reduction in total inflammatory cell counts (FIG. 2A) and in eosinophil counts (FIG. 2B) as compared to both the leucine control (Placebo-A) and a control powder comprised of leucine and sodium chloride (Formulation XVIII). Because FP is a steroid with known anti-inflammatory properties, the effect observed was attributed to the action of FP in the airway. It is for this reason that the dose in the figures on the x-axis was stated in terms of mg of FP/kg of body weight. The data suggested that dry powder formulations of FP and SX could be made that are small, dense and dispersible, and in which the activity of the active ingredient was not altered during the spray drying process.

Example 7. Effect of Dry Powders on Inflammation and Airway Hyperreactivity in an Ovalbumin Mouse Model of Allergic Asthma A mouse model of allergic asthma was established using ovalbumin (OVA). Balb/c mice were sensitized to ovalbumin (OVA) over a period of two weeks and subsequently challenged via aerosol with OVA as indicated in FIG. 12.

Figure 12:
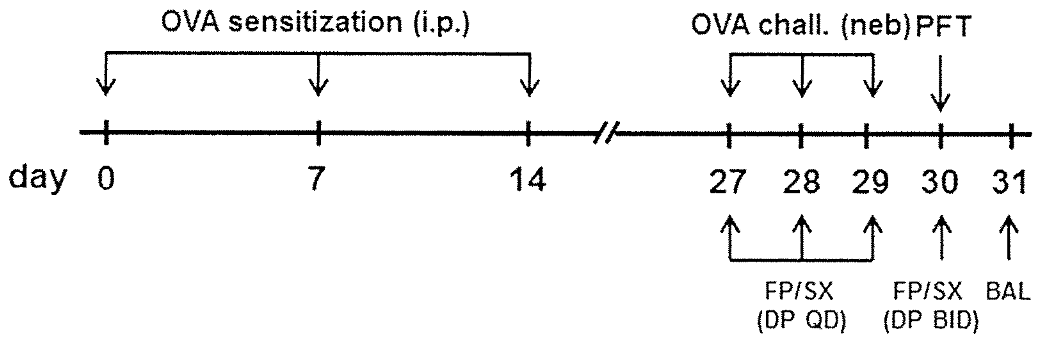
FIG. 12 is a schematic illustrating an ovalbumin (OVA) process of sensitization, sensitization, challenge, treatment, and testing. The process is described in Example 7.

Mice were sensitized to and challenged with OVA on the days depicted in FIG. 12. Sensitizations were performed by intraperotineal injection of OVA plus Alum. Challenges were performed by whole body exposure to nebulized 1% OVA solution for 20 minutes. Mice were treated with a dry powder comprised of 50.0% Leucine 34.5% sodium chloride, 13.5% FP and 2.0% SX (Formulation XVIII) or placebo dry powder (100% Leucine, i.e. Placebo-A) dry powders (DP) 1 hour before OVA challenge on days 27-29 and twice on day 30. Treatments were made in a whole body exposure chamber using a capsule based dry powder inhaler system. On the final day of the study (day 31), mice were euthanized and bronchoalveolar lavages (BAL) were performed. The total number of cells per BAL was determined. In addition, the percentage and total number of macrophages, polymorphonuclear cells (neutrophils), lymphocytes and eosinophils were determined by differential staining. Data depict the mean±SEM of 5 mice per group and are representative of two independent experiments. Data were analyzed by Student's t-test, and asterisk presented in FIGS. 3A and 3B represent a p-value of $p<0.05$.

Figure 3A:
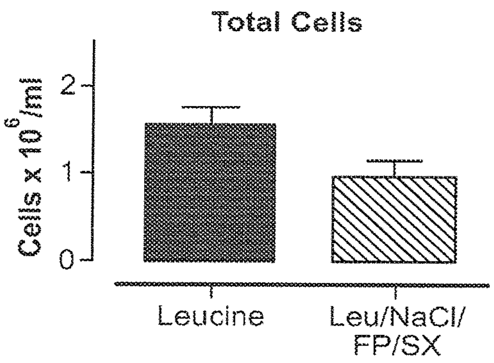
FIGS. 3A-3C are graphs illustrating the efficacy of a monovalent cation-based dry powder formulation of FP/SX in reducing total cell (FIG. 3A) and eosinophil cell (FIG. 3B) counts and airway hyperreactivity (FIG. 3C) in an ovalbumin mouse model of allergic asthma. The graphs indicate that the spray dried drug (FP/SX) remained effective in treating both inflammation and airway hyperreactivity.
Figure 3B:
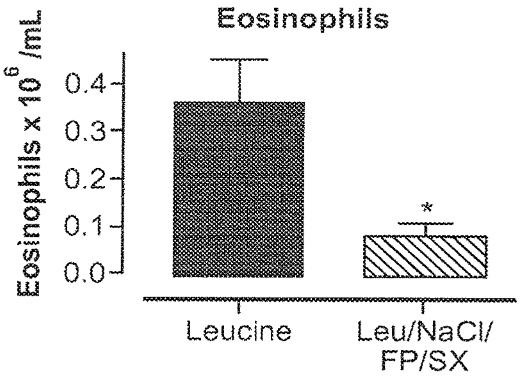

As seen previously (FIGS. 2A and 2B), mice treated with the FP/SX dry powder exhibited a decline in total inflammatory cell counts and a significant decrease in eosinophil counts compared to those mice treated with the leucine dry powder control (FIGS. 3A and 3B).

In addition to changes in inflammation, mice sensitized to and challenged with OVA exhibit increased airway hyperreactivity. It was known from the literature that salmeterol xinafoate (SX) enhances pulmonary function, resulting in lower sRaw values, for animals and human beings challenged with methacholine chloride (MCh) in 0.9% sodium chloride for inhalation. (Schutz, N. (2004), "Prevention of bronchoconstriction in sensitized guinea pigs: efficacy of common prophylactic drugs", Respir Physiol Neurobiol 141(2): 167-178).

Therefore, specific airway resistance (sRaw) was measured in the mice. These measurements were performed on day 30. Baseline sRaw measurements were taken for 5 minutes before treatment, after which the animals received the appropriate DP treatment. Immediately following DP treatments, the animals were returned to the plethysmograph and post-treatment sRaw measurements were then taken. The mice subsequently underwent methacholine (MCh) challenge with escalating concentrations of MCh delivered via nebulization in a head chamber. Data is presented as the average sRaw over the 5 minutes following MCh administration. Naïve mice which were not sensitized to and challenged by OVA also underwent PFT and MCh challenge for the sake of comparison.

Figure 3C:
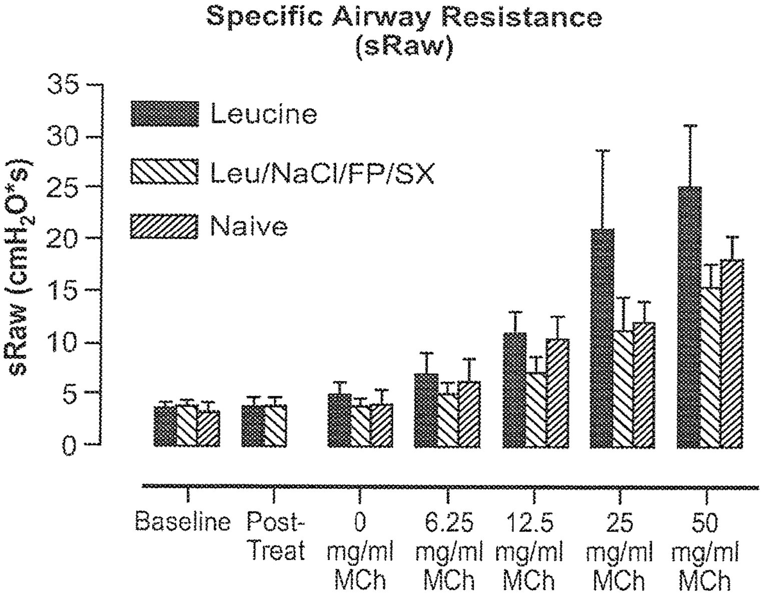

As shown in FIG. 3C, the FP/SX dry powder reduced sRaw values to near those measured in naïve mice after each concentration of MCh challenge. This observation was due to the combined influence of both the reduced airway hyperreactivity as a result of airway inflammation and the influence of the long-acting bronchodilator, SX. The data indicated that not only can dry powder formulations be made that are small, dense and dispersible, but also that the activity of the spray dried active ingredients was maintained.

Example 8. Effect of a Monovalent Cation-Based Dry Powder of FP/SX (Formulation X) on Inflammation and Airway Hyperreactivity in an Ovalbumin Mouse Model of Allergic Asthma A. Inflammation Formulation X (30% leucine, 65.4% NaCl, 4.0% fluticasone propionate and 0.58% salmeterol xinafoate, w/w on a dry basis) was evaluated in a mouse model of allergic asthma using ovalbumin (OVA) as an allergen. The model has been described and shown schematically in Examples 6 and 7 and FIGS. 11 AND 12.

In this model, mice were sensitized to OVA over a period of two weeks and subsequently challenged, via a liquid aerosol, with OVA (Example 6). This challenge induced lung inflammation and increased airway hyperreactivity in response to an airway challenge. The principle change in inflammation was an increase in the number of eosinophils in the lungs. Similar changes in lung inflammation and pulmonary function have been observed in humans with asthma.

Balb/c mice were sensitized and challenged to OVA, as per the sensitization protocol described in Example 6. Mice were treated with Placebo-B dry powder (98% leucine, 2% NaCl, w/w on a dry basis) and Formulation X. Treatments were made in a whole body exposure chamber using a capsule based dry powder inhaler system. As in Example 7, on the final day of the study (day 31), mice were euthanized and bronchoalveolar lavages (BAL) were performed. The total number of cells per BAL was determined. In addition, the percentage and total number of eosinophils was determined by differential staining.

The effect of Formulation X on inflammation was assessed. Fluticasone propionate (FP) is known to reduce eosinophilic cells and total cellularity in the mouse OVA model. (Riesenfeld, E. P. (2010), "Inhaled salmeterol and/or fluticasone alters structure/function in a murine model of allergic airways disease", Respiratory Research, 11:22). However, the effect of co-formulating FP with a sodium salt into a dry powder were unknown in the art. Therefore, Formulation X was tested. The results for Formulation X are presented in Table 22. These data show that Formulation X significantly reduced eosinophilic cells and total cellularity in comparison to Placebo-B ($p<0.01$ for both eosinophils and total cells).

TABLE 22

Formulation X reduces eosinophilic and total cellular inflammation in a murine model of allergic asthma

| | Placebo-B | | Formulation X | |
|---|---|---|---|---|
| | cells*$10^6$/ml | Std Dev | cells*$10^6$/ml | Std Dev |
| Eosinophils | 0.55 | 0.27 | 0.11 | 0.10 |
| Total cells (Cellularity) | 1.38 | .50 | 0.49 | 0.20 |

B. Airway Hyperreactivity

The sensitization of mice with OVA and subsequent challenging of mice with OVA was achieved, as described and shown schematically in Examples 6 and 7 and FIGS. 11 and 12. In addition to changes in inflammation, mice sensitized to and challenged with OVA exhibit increased airway hyperreactivity, as mentioned in Example 7, which can be measured as change in airway resistance following bronchoprovocation. Pulmonary function testing was conducted one hour following treatment on day 30. This involved measuring the specific airway resistance (sRaw) in the mice. sRaw was a means for assessing pulmonary function. Baseline sRaw measurements were taken for 5 minutes. The mice subsequently underwent a methacholine (MCh) challenge for assessing pulmonary function with escalating concentrations of MCh delivered via nebulization in a head chamber using doses of MCh of 0 mg/ml, 50 mg/ml or 100 mg/ml.

Figure 4:
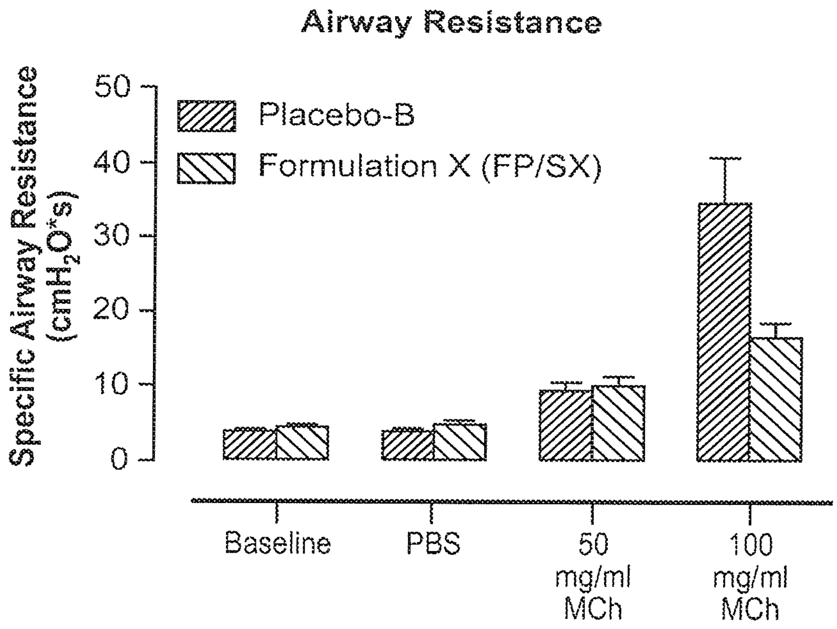
FIG. 4 is a graph illustrating the efficacy of a monovalent cation-based dry powder formulation of FP/SX in reducing airway hyperreactivity in an ovalbumin mouse model of allergic asthma. The graph indicates that the spray dried drug (FP/SX) remained effective in treating airway hyperreactivity.

The mice were challenged to test their pulmonary function according to the methods and schematic described in Example 7 and FIG. 12. It was known from the literature that salmeterol xinafoate (SX) enhances pulmonary function, resulting in lower sRaw values, for animals and human beings challenged with methacholine chloride (MCh) in 0.9% sodium chloride for inhalation. (Schutz, N. (2004), "Prevention of bronchoconstriction in sensitized guinea pigs: efficacy of common prophylactic drugs", Respir Physiol Neurobiol 141(2): 167-178), While the effects of SX on sRaw were known from the literature, the effect of co-formulating SX formulations with a sodium salt were unknown. Formulation X (30% leucine, 65.4% NaCl, 4.0% fluticasone propionate and 0.58% salmeterol xinafoate, w/w on a dry basis) was tested, and compared to Placebo-B dry powder (98% leucine, 2% NaCl, w/w on a dry basis). Results from pulmonary function testing are shown in FIG. 4. These data show that Formulation X significantly reduced sRaw during MCh challenge compared to Placebo-B ($p<0.05$).

Example 9. Effect of a Monovalent Cation-Based Dry Powder of Tiotropium Bromide (Formulation XX) on Airway Hyperreactivity in an Ovalbumin Mouse Model of Allergic Asthma A similar ovalbumin mouse model of allergic asthma as was used in Examples 6 to 8. The protocol of Examples 6 and 7 of sensitization and subsequent challenging with OVA was followed. Pulmonary function testing was conducted as per Example 8.

It was known from the literature that tiotropium bromide (TioB) enhances pulmonary function, resulting in lower sRaw values, for animals and human beings challenged with methacholine chloride (MCh) in 0.9% sodium chloride for inhalation. (Ohta, S. et al. (2010), "Effect of tiotropium bromide on airway inflammation and remodeling in a mouse model of asthma", Clinical and Experimental Allergy 40:1266-1275).

Figure 5:
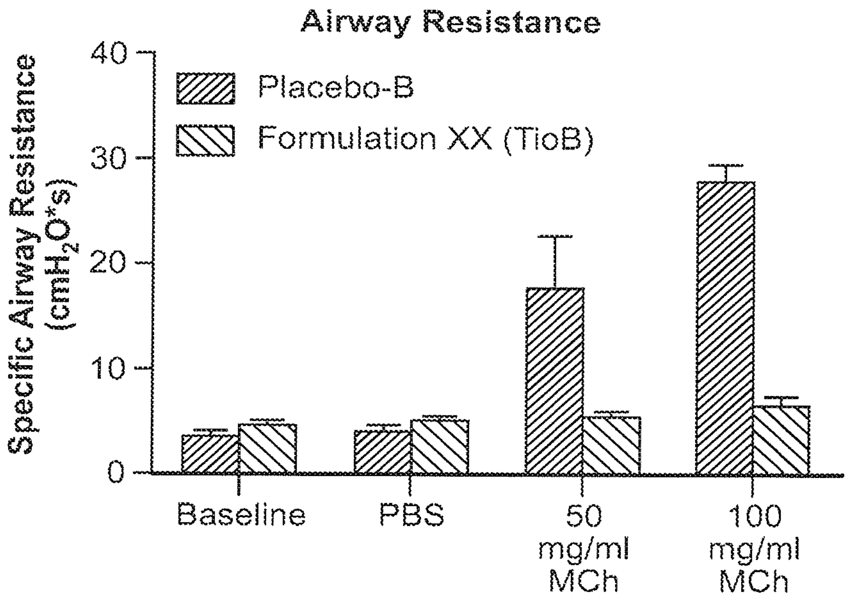
FIG. 5 is a graph illustrating the efficacy of a monovalent cation-based dry powder formulation of tiotroprium bromide (TioB) in reducing airway hyperreactivity in an ovalbumin mouse model of allergic asthma. The graph indicates that the spray dried drug (TioB) remained effective in treating airway hyperreactivity.

While the effects of TioB on sRaw were known from the literature, the effect of co-formulating the TioB formulation with a sodium salt was unknown. Formulations XX (34.47% leucine, 65.42% NaCl and 0.113% tiotropium bromide, w/w on a dry basis) was tested, and compared to Placebo-B dry powder (98% leucine, 2% NaCl, w/w on a dry basis). Results from pulmonary function testing are shown in FIG. 5. These data show that Formulation XX significantly reduced sRaw during MCh challenge compared to Placebo-B ($p<0.00001$).

Figure 13:
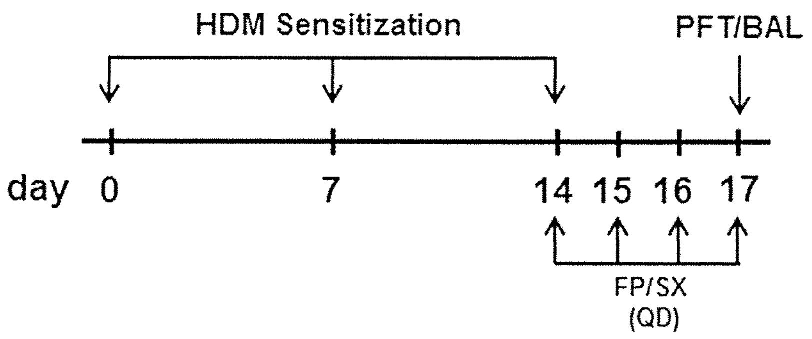
FIG. 13 is a schematic illustrating a house dust mite (HDM) process of sensitization, challenge, treatment, and testing.

Example 10. Efficacy of Monovalent Cation-Based Dry Powders Containing FP/SX in a Mouse House Dust Mite Model of Allergic Asthma Dry powder (DP) formulations comprised of leucine, sodium chloride, fluticasone propionate (FP) and salmeterol xinafoate (SX) were further tested for an ability to reduce inflammation and airway hyperreactivity in a mouse house dust mite (HDM) model of allergic asthma. A mouse model of allergic asthma was established by intranasal administration of 25 μg of freeze-dried *Dermatophagoides pteronyssinus* HDM on days 0, 7 and 14 over a two week period as shown in FIG. 13. Exposure of HDM to mice has been shown to cause an increase in total inflammatory cells, primarily eosinophils, in their lungs and, with chronic exposure, airway hyperreactivity. These similar changes in lung inflammation and pulmonary function have been observed in human asthma.

Balb/c mice were treated with a dry powder comprised of 50.0% Leucine, 34.5% sodium chloride, 13.5% FP and 2.0% SX (Formulation XIX) or a placebo dry powder of 100% Leucine, on a dry basis (Placebo-A) once per day (QD), starting with the final day of HDM sensitization (day 14) until day 17. Treatments were made in a whole body exposure chamber using a capsule-based dry powder inhaler system. Immediately following treatment on day 17, the animals underwent pulmonary function testing (PFT) by dual chamber plethysmography. Specific airway resistance (sRaw) measurements were taken at baseline and following methacholine (MCh) challenge. Immediately following dry powder treatment, 5 minutes of baseline sRaw measurements were taken. sRaw measurements were then taken following escalating doses of MCh delivered via nebulization to the head chamber. Data is presented as the average sRaw over the 5 minutes following MCh administration.

Mice were then euthanized and bronchoalveolar lavages (BAL) were performed. The total number of cells per BAL was determined, and the percentage and total number of macrophages, polymorphonuclear cells (neutrophils), lymphocytes, and eosinophils were determined by differential staining. A group of naïve, non-sensitized, untreated mice also underwent PFT and BAL for comparison. Data depict the mean±SEM and were analyzed by one way ANOVA and Tukey's multiple comparison test (*p<0.5) (**p<0.01).

Figure 6A:
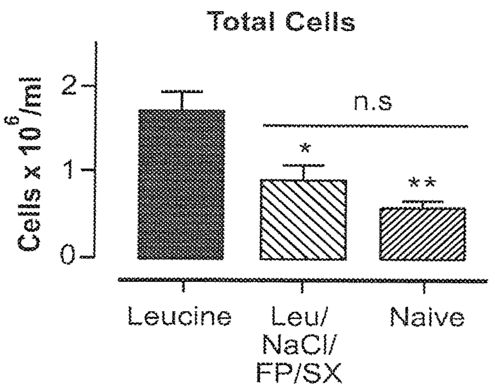
FIGS. 6A-6C are graphs illustrating the efficacy of a monovalent cation-based dry powder formulation of FP/SX in reducing total cell (FIG. 6A) and eosinophil cell (FIG. 6B) counts and airway hyperreactivity (FIG. 6C) in a house dust mite (HDM) mouse model of allergic asthma. The graphs indicate that the spray dried drug (FP/SX) remained effective in treating both inflammation and airway hyperreactivity.
Figure 6B:
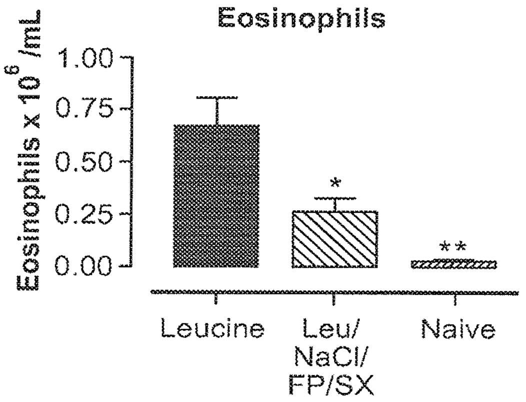

The FP/SX dry powder significantly reduced total inflammatory cell counts to near that of naïve mice in comparison to leucine placebo treatment (FIG. 6A). In addition, eosinophil counts were significantly reduced by nearly 60% (FIG. 6B). The reduction in inflammatory and eosinophil counts indicated that the anti-inflammatory properties of the FP steroid were maintained in the dry powder.

Figure 6C:
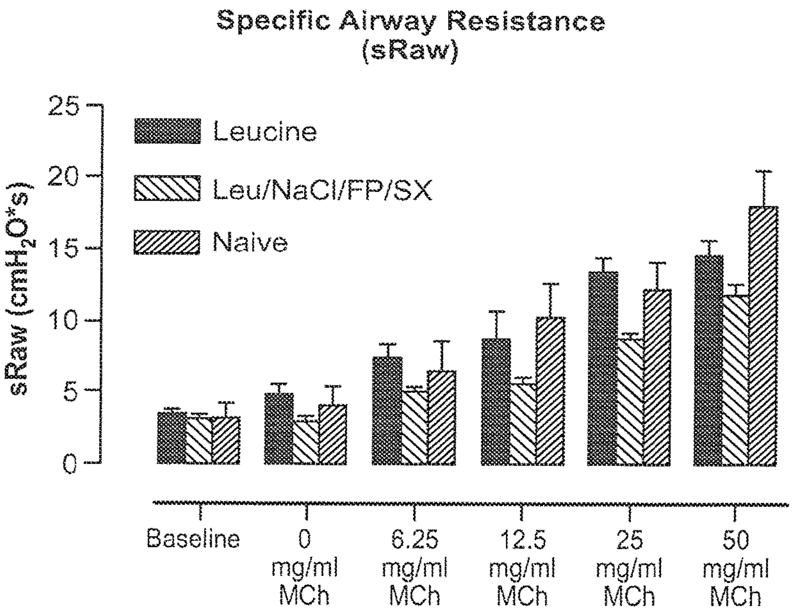

Furthermore, the FP/SX dry powder reduced sRaw values below those measured in both HDM sensitized mice that received placebo dry powder treatment (FIG. 6C). The fact that mice treated with the FP/SX dry powder demonstrated less of a bronchoconstrictive response to MCh than naïve mice, while exhibiting increased eosinophilia suggested that the reduced hyperreactivity in mice treated with the FP/SX dry powder was due primarily to the influence of the long-acting bronchodilator SX. Thus, the data indicated that activity of each active ingredient in a small, dense and dispersible dry powder formulation described herein was retained.

Example 11. Efficacy of Monovalent Cation-Based Dry Powders Containing FP/SX in an LPS Mouse Model of Acute Lung Injury In this study, a mouse model of acute lung injury was used to study the effects of FP/SX co-formulated with a sodium salt on pulmonary inflammation. Mice were exposed to aerosolized lipopolysaccharide (LPS) isolated from *Pseudomonas aeruginosa*. This challenge resulted in lung inflammation and caused changes in pulmonary function. The principle change in inflammation was an increase in the number of neutrophils in the lungs. Similar changes in lung inflammation and pulmonary function have been observed in humans suffering from acute lung injury.

Mice were exposed to whole body exposure with nebulized LPS, 1.12 mg/ml, for 30 minutes. Treatment with dry powder Formulation X (30% leucine, 65.4% NaCl, 4.0% fluticasone propionate and 0.58% salmeterol xinafoate, w/w on a dry basis) was performed 1 hour following LPS exposure using a whole body exposure chamber using a capsule based dry powder inhaler system. Animals were treated with two, 90 mg capsules. A separate group of animals was treated with two, 30 mg capsules of Placebo-B dry powder (98% leucine, 2% NaCl, w/w on a dry basis). Three hours following dry powder treatment, all mice were euthanized and underwent whole lung lavage for determination of total and differential cell counts.

As shown in Table 23, treatment of mice with Formulation X significantly reduced total cell counts (p<0.01) and neutrophils (p<0.01) in the BAL fluid when compared with animals exposed to Placebo-B. Thus, treatment of mice with Formulation X significantly reduced lung inflammation in an LPS model of acute lung injury.

TABLE 23

Formulation X reduces inflammation in a rodent model of acute lung injury.

| | Placebo-B | | Formulation X | |
|---|---|---|---|---|
| | cells*$10^6$/ml | Std Dev | cells*$10^6$/ml | Std Dev |
| Neutrophils | 0.81 | 0.23 | 0.36 | 0.12 |
| Total cells (Cellularity) | 0.98 | 0.19 | 0.55 | 0.15 |

Example 12. Efficacy of Monovalent Cation-Based Dry Powder Containing Ciprofloxacin in a Mouse Model of Bacterial Pneumonia A neutropenic mouse model of *Pseudomonas aeruginosa* was used to evaluate the efficacy of Formulation IV (10.0% mannitol, 40% sodium chloride, 50% ciprofloxacin hydrochloride, w/w on a dry basis). Mice (C57BL6; ~20 g) were given two doses of cyclophosphamide monohydrate (Sigma Aldrich; St Louis, Mo.) dissolved in sterile water for injection on day −4 (200 mg/kg) and day −1 (100 mg/kg) relative to the day of infection (day 0). Cyclophosphamide was given by intraperotineal injection and acts to deplete neutrophils. *P. aeruginosa* (PAO1) was prepared by growing a culture in 2.0 mL of Luria Bertani (LB) broth overnight at 37° C. with shaker speed of 430 rpm. Cultures were diluted 1:100 the following day and grown to an $OD_{600}$~0.3. Once the $OD_{600}$ reached ~0.3, three washes were performed in sterile PBS and the resulting suspension was subsequently diluted 1:2000 in sterile PBS [~$1.3\times10^5$ Colony forming units (CFU)/mL]. Mice were infected with 50 μL of bacterial suspension (~$6\times10^3$ CFU/mouse) by intranasal instillation while under injectable anesthesia.

Figure 7:
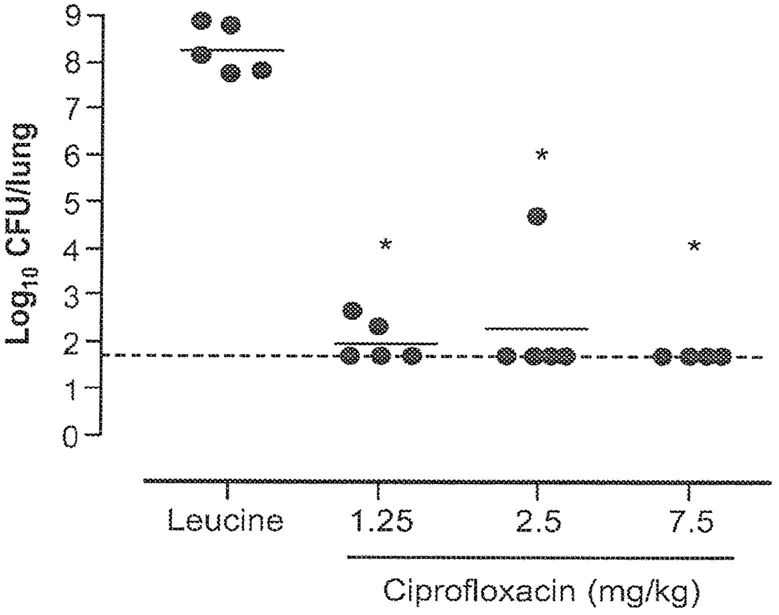
FIG. 7 is a graph illustrating the efficacy of a monovalent cation-based dry powder formulation of ciprofloxacin (Formulation IV) in treating bacterial pneumonia in vivo in a mouse model. The graph indicates that spray dried ciproflaxacin was active against *P. aeruginosa.*

Mice were exposed to Formulation IV or a control powder comprised of 100% leucine on a dry basis (Placebo-A) as a control in a whole-body exposure system using a capsule based system and a flow control unit connected to a pie chamber cage that individually holds up to 11 animals. Treatments were performed 4 hours after infection with *P. aeruginosa*. Exposure times were dependent on the number of capsules to be emitted. Doses reported are the exposed dose each mouse inhaled as calculated based on the measured aerosol concentration sampled from the exposure chamber, the fraction of ciprofloxacin in the powder, the time of exposure, and the mouse's mass and minute volume. Mouse minute volume was calculated using a standard equation (Bide et al. (2000) "Allometric respiration/body mass data for animals to be used for estimates of inhalation toxicity to young adult humans", J. Appl. Toxicol. 20:273-290). Twenty-four hours after infection, mice were euthanized by pentobarbital injection and lungs were collected and homogenized in sterile PBS. Lung homogenate samples were serially diluted in sterile PBS and plated on TSA blood agar plates. CFU were enumerated on the following day. As shown in FIG. 7, compared to control animals exposed to Placebo-A, Formulation IV-treated animals exhibited greatly reduced bacterial titers 24 hours after infection. This data suggested that spray-dried ciprofloxacin was active against *P. aeruginosa* at doses of less than 7.5 mg/kg and that spray-dried DP formulations of ciprofloxacin could be made small, dense and dispersible.

Example 13. Efficacy of Monovalent Cation-Based Dry Powder Containing Levofloxacin in a Mouse Model of Bacterial Pneumonia A mouse model of bacterial infection was used to evaluate the efficacy of Formulation XXI in vivo. Neutropenia was induced by injection of cyclophosphamide (100 mg/kg) on days −4 and −1. Bacteria (*Pseudomonas aeruginosa*) were grown overnight in 2 ml of Luria Bertani broth at 37° C. and approximately $5\times10^3$ CFU were delivered per mouse via intranasal administration in 50 μl of PBS. Four hours following infection the animals were treated with Formulation XXI (27% leucine, 53% NaCl and 20% levofloxacin, w/w on a dry basis) and with Placebo-B dry powder (98% leucine, 2% NaCl) using a whole body exposure chamber and a capsule based dry powder inhaler system. The next day, animals were euthanized and the lungs and the spleen were harvested and homogenized to determine lung bacterial load and systemic bacterial load, respectively. Homogenates were serially diluted on tryptin-soyagar plates and allowed to incubate overnight at 37° C. The following day, colony forming units (CFU) were counted and CFU/ml for each the lung and the spleen was calculated.

Levofloxacin, being a potent antibiotic would be expected to significantly reduce CFU count in the spleen when administered through the gastro-intestinal tract. What was unknown were the following: (i) would co-formulating levofloxacin with a sodium salt have any effect on the efficacy of levofloxacin when administered to the lungs, and (ii) would these co-formulation of levofloxacin, when administered to the lungs, cause a reduction of CFU count in the spleen. The results are shown in Table 24. It was seen that Formulation XXI significantly reduced bacterial burden in the lung by more than 4 $\log_{10}$ CFU and in the spleen by almost 100-fold compared to Placebo-B treated animals. Thus, treatment of mice with Formulation XXI significantly reduced lung and systemic bacterial burden (CFU count) during *Pseudomonas aeruginosa* infection, proving that levofloxacin could be (i) co-formulated with a sodium salt and still have efficacy when administered to the lungs, and (ii) administered to the lungs as a co-formulation to reduce CFU count in the spleen.

It was observed from these data that the presence of sodium in levofloxacin dry powder formulations did not have a deleterious effect on the efficacy of levofloxacin. This is a surprising result given the literature which says that various salt formulations deleteriously affect the bioavailability of levofloxacin taken through the gastrointestinal tract. (Flor, S. et al. (1990), "Effects of Magnesium-Aluminum Hydroxide and Calcium Carbonate Antacids on Bioavailability of Ofloxacin", Antimicrobial Agents and Chemotherapy 34(12): 2436-2438), and (Pai, M P. et al. (2006), "Altered steady state pharmacokinetics of levofloxacin in adult cystic fibrosis patients receiving calcium carbonate", J. Cyst. Fibros., August; 5(3):153-7). (Ofloxacin is a racemic mixture, which consists of 50% levofloxacin, which is known to be biologically active, and 50% of its enantiomer.)

TABLE 24

Formulation XXI reduces bacterial burden during *Pseudomonas aeruginosa* infection

| | Placebo-B | | Formulation XXI | |
|---|---|---|---|---|
| | CFU/ml | Std Dev | CFU/ml | Std Dev |
| Lung | $2.85 \times 10^8$ | $2.88 \times 10^8$ | $2.08 \times 10^4$ | $3.87 \times 10^4$ |
| Spleen | $1.57 \times 10^5$ | $1.78 \times 10^5$ | $2.16 \times 10^3$ | $6.81 \times 10^2$ |

Example 14. Efficacy of Monovalent Cation-Based Dry Powders Containing Insulin in Reducing Blood Glucose Levels in a Mouse Model In this study, Formulations XXIV and XXVIII (Table 25) containing recombinant human insulin (Sigma-Aldrich, St. Louis, Mo., approx. 27.5 U/mg, dry powder) were used to determine if monovalent cation-based dry powder formulations could be used to deliver proteins to the lung and if this dry powder could be used to deliver proteins systemically.

TABLE 25

Insulin containing dry powder formulations

| Form. | Salt | % Salt load (w/w) | Excipient | % Excipient load (w/w) | Drug | % Drug load (w/w) | % HCl load (w/w) |
|---|---|---|---|---|---|---|---|
| XXIV | Sodium sulfate | 49.0 | Mannitol | 39.0 | Insulin | 8.0 | 4.0 |
| XXVIII | Sodium sulfate | 54.0 | Mannitol | 39.0 | Insulin | 5.0 | 2.0 |

The sodium sulfate/mannitol solution was adjusted with hydrochloric acid (HCl) to obtain a low pH solution in which the insulin was soluble. The resulting DP contained 8% insulin (Formulation XXIV) and 5% insulin (Formulation XXVIII).

In this study, mice (n=5) were treated with 6 capsules of either Formulation XXIV or XXVIII, with another group of animals that were treated with 6 capsules of Placebo-B control powder (98% leucine, 2% NaCl), using a whole body exposure chamber with a capsule based dry powder inhaler system. Whole blood was drawn from the mice by tail snip. Blood glucose levels were measured at 0 minutes (immediately before DP treatment), 30 minutes, 1 hour and 2 hours following DP treatment using a LIFESCAN One-Touch Ultra 2 blood glucose monitoring system (Johnson & Johnson, New Brunswick, N.J.).

Figure 8:
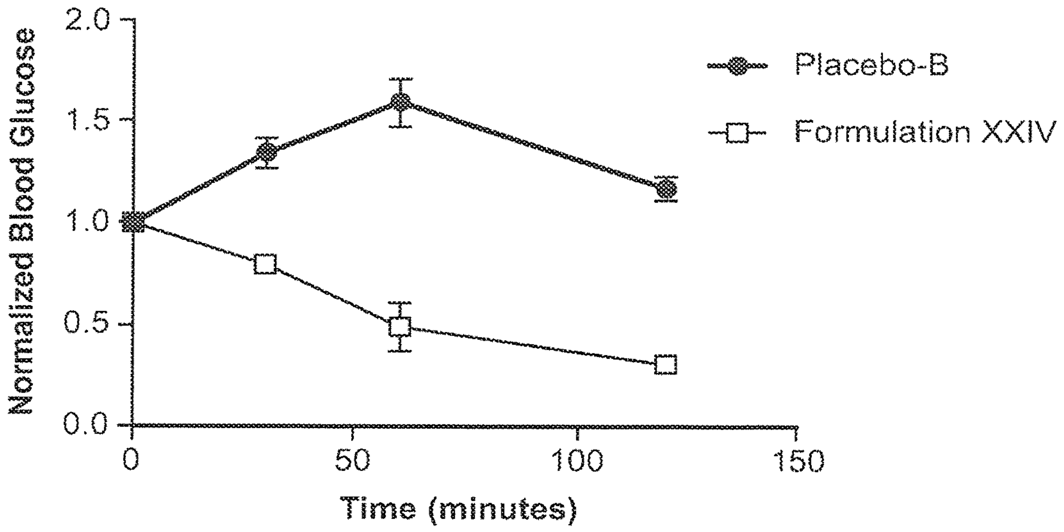
FIGS. 8 and 9 are graphs illustrating the efficacy of monovalent cation-based dry powder formulations of insulin at a loading of 8% and 5%, respectively, at reducing the blood glucose levels in mice.
Figure 9:
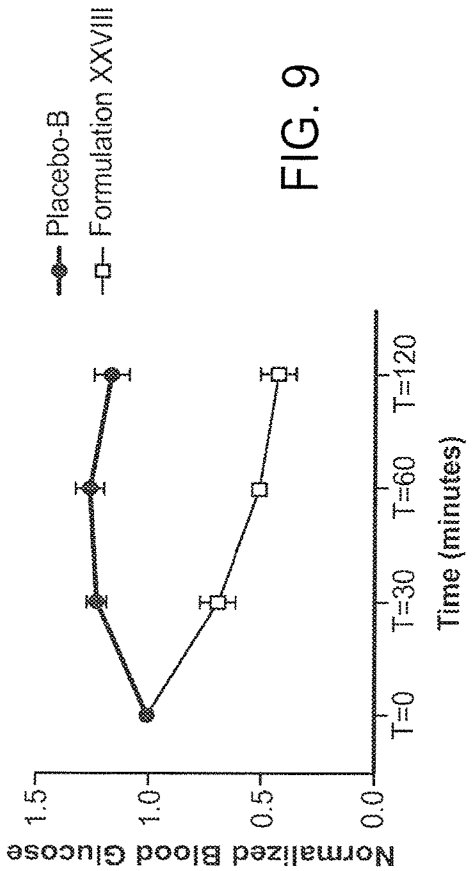

The results are shown in FIG. 8 (Formulation XXIV, 8% insulin) and FIG. 9 (Formulation XXVIII, 5% insulin). The placebo treated animals, Placebo-B, showed a small increase in glucose levels, likely as a stress ("fight or flight") response to the powder administration and/or tail snip for the blood measurement. Glucose levels rapidly and significantly dropped in insulin-treated animals with levels reaching the lower detection limit of the glucose sensor (20 mg/dL) at 2 hours after DP treatment. This demonstrated that monovalent cation-containing dry powders can be utilized to deliver proteins. Hormones, such as insulin, delivered in an animal model by DP can have fast-acting, systemic physiological, pharmacological effects in vivo.

Example 15. Sodium Formulation of an Immunoglobulin Protein Provides for Delivery of the Protein Both Locally in the Lungs and Systemically In this study, Formulation XXV (50.0% sodium sulfate, 47.5% mannitol, 2.5% bovine immunoglobulin G (IgG), w/w on a dry basis) was used to determine if monovalent cation salt-based dry powder formulations could be used to deliver proteins to the lungs and/or systemically by way of the lungs.

In this study, mice were treated with Formulation XXV using a whole body exposure chamber using a capsule-based dry powder inhaler system. Animals were then treated with 3 or 6 capsules of Formulation XXV with another group of animals that were treated with 6 capsules of placebo control powder (98% leucine, 2% NaCl; Placebo-B). The placebo controls were run to ensure that there was no cross reactivity with the bovine IgG assay and native mouse proteins in either the serum or the broncho-alveolar lavage (BAL).

Immediately following DP treatment the animals were euthanized, underwent BAL and serum was collected. Lavage fluid and serum were then assayed for bovine IgG using a commercially available ELISA kit.

Figure 10A:
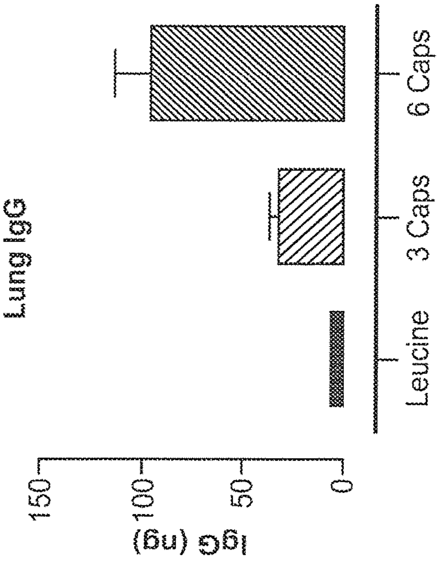
FIGS. 10A and 10B are graphs illustrating the ability of a monovalent cation-powder formulation of immunoglobulin G (IgG) to deliver IgG to both the lungs and serum of mice. These graphs indicate that delivery of a large protein to the lungs with a spray dried formulation of the protein and a monovalent cation salt is feasible.
Figure 10B:
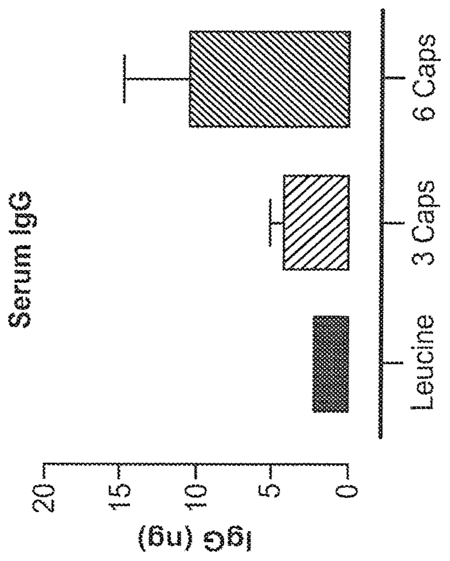

The data for lung detection of the IgG are shown in FIG. 10-A and for serum detection of the IgG are shown in FIG. 10-B. Placebo-B (n=3 animals) was below the detectable range of the assay, which was indicative that there was no cross reactivity between the bovine IgG and the native mouse protein in either the serum or the BAL. It could be seen that detectable IgG delivered to the lung, and systemically by way of the lungs, increased stepwise with increasing number of capsules delivered to the animals. This demonstrated that monovalent cation-containing dry powders can be utilized to deliver proteins. Even large proteins such as immunoglobulins, such as IgG, and antibodies delivered in an animal model by DP could have fast acting, systemic physiological, pharmacological effects in vivo.

Example 16. Optimization of a Dry Powder Sodium-Based Formulation of Fluticasone Propionate and Salmeterol Xinafoate Two sodium salt-based fluticasone propionate/salmeterol xinafoate (FP/SX) formulations were processed, Formulations I and XXXIII. (See Table 26) Formulation I dry powder was produced by spray drying on the Büchi B-290 Mini Spray Dryer (BÜCHI Labortechnik AG, Flawil, Switzerland) with powder collection in a 60 mL glass vessel from a High Performance cyclone. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm and the aspirator rate to 90% (35 $m^3$/h). Room air was used as the drying gas. Inlet temperature of the process gas was 180° C. and outlet temperature from 86° C. to 87° C. with a liquid feedstock flow rate of 8 mL/min to 9 mL/min. The solids concentration was 10 g/L in 60% ethanol and 40% water.

Formulation XXXIII shared the same chemical components and composition as Formulation I, as listed in Table 26. The solution preparation was the same as for Formulation I, namely that the solids concentration was 10 g/L in 60% ethanol and 40% water. The spray drying process conditions of Formulation XXXIII were the same as for Formulation I, except that for Formulation XXXIII, the inlet temperature was decreased from 180° C. to 100° C., the aspirator rate was changed from 90% to 80% (35 cubic meters per hour to 32 cubic meters per hour), and the feed rate was increased from 8.6 to 10.2 mL/min.

TABLE 26

Sodium chloride-based formulations of FP/SX

| Formulation | Salt | % Salt load (w/w) | Excipient | % Excipient load (w/w) | Drug | % Drug load (w/w) |
|---|---|---|---|---|---|---|
| I | Sodium chloride | 65.4 | Leucine | 30.0 | FP/SX | 4.0/0.58 |
| XXXIII | Sodium chloride | 65.4 | Leucine | 30.0 | FP/SX | 4.0/0.58 |

The modified processing conditions used to generate Formulation XXXIII were determined through process optimization. Formulation XXXIII had a significantly higher capsule emitted powder mass (CEPM), both at a higher flow rate of 60 LPM and at a lower flow rate of 15 LPM that Formulation I had at 60 LPM and 30 LPM. It should be noted that Formulation I was only run at a lower flow rate of 30 LPM, which provides more dispersion energy than at 15 LPM, yet Formulation XXXIII had a significantly higher CEPM than Formulation I at the lower flow rates. CEPM is relevant when it comes to determining the dose of the formulation and therefore the active agent a patient would receive from the inhaler. Formulation XXXIII also has an improved ratio of CEPM high flow rate/CEPM low flow rate that Formulation I. Results from the CEPM characterization can be seen in Table 27.

This example showed how a monovalent salt formulation which contained an active agent could be optimized to produce particles and powders with improved properties.

TABLE 27

CEPM Dispersibilty Properties

| Formulation | Dispersibility-CEPM @ 60 LPM | Formulation I @ 30 LPM Formulation II @ 15 LPM |
|---|---|---|
| I | 62% ± n/a | 44% ± n/a |
| XXXIII | 100.1% ± 2.0% | 95.7% ± 1.0% |

n/a = not available

Example 17 A Monovalent Metal Cation DP Containing Tiotropium Bromide is Effective to Enhance Pulmonary Function in Mice Challenged with Methacholine Chloride (MCh) in a Mouse Model of Rhinovirus Infection A mouse model of Rhinovirus infection with Rhinovirus minor 1B strain was used (REF). Female inbred Balb/c mice (body weights on initial day of use: 16.8-24.3 g) were obtained from Charles River Laboratories. Mice (n=4) were infected intranasally with $5\times10^6$ TCID50 of Rhinovirus-1B. Mice were exposed to dry powder Formulation XXXII using a custom designed whole body exposure system 18 hours after virus infection. Pulmonary function testing was conducted at approximately 1 hour following dry powder treatment. Baseline specific airway resistance (sRaw) measurements were taken for 5 minutes before treatment and the mice subsequently underwent methacholine (MCh) challenge with escalating concentrations of MCh (0-100 mg/ml) delivered via nebulization into the head chamber. Data in Table 28 is presented as the average sRaw over the 5 minutes following MCh administration.

TABLE 28

| MCh Concentration (mg/ml) | Placebo-B sRaw ($cmH_2O$*s) | Placebo-B Std Dev | Formulation XXXII sRaw ($cmH_2O$*s) | Formulation XXXII Std Dev |
|---|---|---|---|---|
| 0 | 3.30 | 0.22 | 2.71 (n.s.) | 0.96 |
| 50 | 8.55 | 3.92 | 2.68 ($p < 0.05$) | 1.04 |
| 100 | 15.26 | 4.81 | 3.47 ($p < 0.01$) | 0.50 |

The data show that Formulation XXXII significantly reduced sRaw during MCh challenge compared to Placebo ($p<0.05$) at 50 and 100 mg/ml MCh.

The content of each of the patents, patent applications, patent publications and published articles cited in this specification are herein incorporated by reference in their entirety.

What is claimed is:

1. A respirable dry powder comprising respirable dry particles that comprise sodium sulfate, leucine, an active agent, wherein said active agent is an anti-fungal, and an optional excipient; wherein the respirable dry powder comprising respirable dry particles is characterized by a volume median geometric diameter (VMGD) at 1 bar as measured using a HELOS/RODOS system between 0.5 microns and 5 microns, a tap density of greater than 0.4 g/cc to about 1.2 g/cc, and a dispersibility ratio of 1 bar/4 bar of about 1.5 or less.

2. The respirable dry powder of claim 1, wherein the sodium sulfate is present in an amount between about 20% and about 60%, wherein the weight percentages are on a dry basis of the respirable dry particles.

3. The respirable dry powder of claim 1, wherein the leucine is present in an amount of about 50% or less, wherein the weight percentage is on a dry basis of the respirable dry particles.

4. The respirable dry powder of claim 1, wherein the anti-fungal agent is present in an amount between about 10% and about 50%, wherein the weight percentages are on a dry basis of the respirable dry particles.

5. The respirable dry powder of claim 1, wherein the active agent is present in an amount between about 50% and about 99.9%, wherein the weight percentages are on a dry basis of the respirable dry particles.

6. A method of treating a pulmonary disease comprising administering to the respiratory tract of a patient in need thereof an effective amount of the respirable dry powder of claim 1.

7. The method of claim 6, wherein the pulmonary disease is asthma, airway hyperresponsiveness, seasonal allergic allergy, bronchiectasis, chronic bronchitis, emphysema, chronic obstructive pulmonary disease, cystic fibrosis, or idiopathic pulmonary fibrosis.

* * * * *